US005942496A

United States Patent [19]
Bonadio et al.

[11] Patent Number: 5,942,496
[45] Date of Patent: Aug. 24, 1999

[54] METHODS AND COMPOSITIONS FOR MULTIPLE GENE TRANSFER INTO BONE CELLS

[75] Inventors: Jeffrey Bonadio; Steven A. Goldstein, both of Ann Harbor, Mich.

[73] Assignee: The Regent of The University of Michigan, Ann Arbor, Mich.

[21] Appl. No.: 08/316,650

[22] Filed: Sep. 30, 1994

Related U.S. Application Data

[63] Continuation-in-part of application No. 08/199,780, Feb. 18, 1994, Pat. No. 5,763,416.

[51] Int. Cl.⁶ .................................................. A01N 43/04
[52] U.S. Cl. .................. 514/44; 435/69.1; 435/320.1; 435/325; 435/455; 435/458; 424/93.21
[58] Field of Search .......................... 514/44; 435/172.3, 435/69.1, 320.1, 240.2, 240.1, 240.25, 455, 458, 325; 424/93.21; 800/2

[56] References Cited

U.S. PATENT DOCUMENTS

| | | |
|---|---|---|
| 3,277,033 | 10/1966 | Ugi ............................................ 260/18 |
| 3,839,297 | 10/1974 | Wasserman et al. .............. 260/78.3 R |
| 4,137,921 | 2/1979 | Okuzumi et al. ..................... 128/335.5 |
| 4,166,800 | 9/1979 | Fong ........................................ 252/316 |
| 4,181,983 | 1/1980 | Kulkarni .......................................... 3/1 |
| 4,243,775 | 1/1981 | Rosensaft et al. ....................... 525/415 |
| 4,279,249 | 7/1981 | Vert et al. .............................. 128/92 D |
| 4,300,565 | 11/1981 | Rosensaft et al. ................... 128/335.5 |
| 4,347,234 | 8/1982 | Wahlig et al. ............................ 424/15 |
| 4,384,975 | 5/1983 | Fong .................................. 427/213.36 |
| 4,390,519 | 6/1983 | Sawyer ...................................... 424/28 |
| 4,409,332 | 10/1983 | Jefferies et al. ......................... 435/188 |
| 4,455,256 | 6/1984 | Urist .................................... 260/112 R |
| 4,472,840 | 9/1984 | Jefferies ..................................... 3/1.9 |
| 4,497,796 | 2/1985 | Salser et al. .......................... 424/93.21 |
| 4,530,449 | 7/1985 | Tune ......................................... 623/16 |
| 4,534,958 | 8/1985 | Adams et al. ............................. 424/45 |
| 4,538,603 | 9/1985 | Pawelchak et al. .................... 128/156 |
| 4,539,981 | 9/1985 | Tune ..................................... 128/92 B |
| 4,563,350 | 1/1986 | Nathan et al. ............................ 424/95 |
| 4,563,489 | 1/1986 | Urist ........................................ 524/21 |
| 4,568,559 | 2/1986 | Nuwayser et al. .......................... 427/3 |
| 4,578,384 | 3/1986 | Hollinger ................................... 514/8 |
| 4,585,797 | 4/1986 | Cioca ...................................... 514/773 |
| 4,591,501 | 5/1986 | Cioca ...................................... 424/28 |
| 4,596,574 | 6/1986 | Urist ......................................... 623/16 |
| 4,619,989 | 10/1986 | Urist ....................................... 530/417 |
| 4,623,588 | 11/1986 | Nuwayser et al. ................. 428/402.24 |
| 4,670,393 | 6/1987 | Seeburg .................................. 435/240 |
| 4,703,108 | 10/1987 | Silver et al. ........................... 530/356 |
| 4,711,783 | 12/1987 | Huc et al. ............................... 424/460 |
| 4,741,337 | 5/1988 | Smith et al. ........................ 128/334 R |
| 4,743,679 | 5/1988 | Cohen et al. ............................ 530/350 |
| 4,744,365 | 5/1988 | Kaplan et al. ....................... 128/335.5 |
| 4,761,471 | 8/1988 | Urist ........................................ 530/350 |
| 4,776,890 | 10/1988 | Chu ......................................... 106/161 |
| 4,789,663 | 12/1988 | Wallace et al. ........................... 514/21 |
| 4,789,732 | 12/1988 | Urist ........................................ 530/350 |
| 4,795,804 | 1/1989 | Urist ........................................ 530/350 |
| 4,798,786 | 1/1989 | Tice et al. ............................... 435/177 |
| 4,806,523 | 2/1989 | Bentz et al. ............................... 514/2 |
| 4,818,542 | 4/1989 | DeLuca et al. ......................... 424/491 |
| 4,833,125 | 5/1989 | Neer et al. ................................ 514/12 |

(List continued on next page.)

FOREIGN PATENT DOCUMENTS

| | | |
|---|---|---|
| 0 614 974 A2 | 9/1994 | European Pat. Off. . |
| 0372031B1 | 9/1996 | European Pat. Off. . |
| 42 19 626 A1 | 12/1993 | Germany . |
| 9011092 | 4/1990 | WIPO . |
| WO 90/03733 | 4/1990 | WIPO . |
| WO 90/11092 | 10/1990 | WIPO . |
| WO 90/14074 | 11/1990 | WIPO . |
| WO 91/17424 | 11/1991 | WIPO . |
| WO91/18558 | 12/1991 | WIPO . |
| WO 92/05199 | 4/1992 | WIPO . |

(List continued on next page.)

OTHER PUBLICATIONS

Geber Garmet Technology v. Lectra Systems, 16 USPQ 2d 1436, Oct. 10, 1990.
Marshal, Science 269:1050–1055, 1995.
Miller et al., FASEB J. 9:190–199, 1995.
Calver et al., Trends Genetics 10(5):174–178, 1994.
Hodgson, Exp. Opin. Ther. Pat. 5(5):459–468, 1995.
Wilson et al., Endocrinology 130(5): 2947, 1992.
Chen et al., J. Bone and Min. Res. 6(12):1387, 1991.
Toriumi et al., Arch Otolaryngol Head Neck Surg., 117:1101–1112, 1991.
Zhu et al., 40th Ann. Meet Orthopaedic Res. Society, Feb. 21, 1994, 14–3.
Australian Examiners's First Report dated Oct. 28, 1997.
International Search Report dated Sep. 12, 1997 (PCT/US97/10079).
Di Silvo, Courteney, and Downes, "The Use of Gelatin as a Vehicle for Drug and Peptide Delivery," Chapman & Hall, 819–823, 1994.
Ando, et al., "Localization of Transforming Growth Factor–β and Latent Transforming Growth Factor–β Binding Protein in Rat Kidney," *Kidney International* 47:733–739, 1995.
Chaudhry, et al., "Expression of Tranforming Growth Factors Beta 1, Beta 2, Beta 3 in Neuroendocrine Tumors of the Digestive System," *Anticancer Res* 14(5B):2085–91, 1994 (Abstract).

(List continued on next page.)

*Primary Examiner*—Bruce R. Campell
*Assistant Examiner*—Dave Trong Nguyen
*Attorney, Agent, or Firm*—Arnold White & Durkee

[57] ABSTRACT

Disclosed are methods, compositions, kits and devices for use in transferring nucleic acids into bone cells in situ and/or for stimulating bone progenitor cells. Type II collagen and, particularly, osteotropic genes, are shown to stimulate bone progenitor cells and to promote bone growth, repair and regeneration in vivo. Gene transfer protocols are disclosed for use in transferring various nucleic acid materials into bone, as may be used in treating various bone-related diseases and defects including fractures, osteoporosis, osteogenesis imperfecta and in connection with bone implants.

130 Claims, 14 Drawing Sheets

U.S. PATENT DOCUMENTS

| | | | |
|---|---|---|---|
| 4,837,285 | 6/1989 | Berg et al. | 530/356 |
| 4,839,130 | 6/1989 | Kaplan et al. | 264/235 |
| 4,844,854 | 7/1989 | Kaplan et al. | 264/235 |
| 4,865,846 | 9/1989 | Kaufman | 424/428 |
| 4,877,864 | 10/1989 | Wang et al. | 530/324 |
| 4,882,150 | 11/1989 | Kaufman | 424/428 |
| 4,889,119 | 12/1989 | Jamiolkowski et al. | 606/220 |
| 4,898,186 | 2/1990 | Ikada et al. | 606/62 |
| 4,898,734 | 2/1990 | Mathiowitz et al. | 424/426 |
| 4,902,508 | 2/1990 | Badylak et al. | 424/95 |
| 4,916,793 | 4/1990 | Tang et al. | 525/413 |
| 4,938,763 | 7/1990 | Dunn et al. | 604/891.1 |
| 4,946,450 | 8/1990 | Erwin | 604/294 |
| 4,952,402 | 8/1990 | Sparks et al. | 424/419 |
| 4,956,178 | 9/1990 | Badylak et al. | 424/551 |
| 4,957,902 | 9/1990 | Grinnell | 514/17 |
| 4,961,707 | 10/1990 | Magnusson et al. | 433/215 |
| 4,968,590 | 11/1990 | Kuberasampath et al. | 530/326 |
| 4,975,526 | 12/1990 | Kuberasampath et al. | 530/350 |
| 4,975,527 | 12/1990 | Koezuka et al. | 530/356 |
| 4,988,358 | 1/1991 | Eppley et al. | 623/16 |
| 5,001,169 | 3/1991 | Nathan et al. | 523/113 |
| 5,004,602 | 4/1991 | Hutchinson | 424/78 |
| 5,007,939 | 4/1991 | Delcommune et al. | 623/66 |
| 5,011,691 | 4/1991 | Oppermann et al. | 424/423 |
| 5,011,692 | 4/1991 | Fujioka et al. | 424/426 |
| 5,013,649 | 5/1991 | Wang et al. | 435/69.1 |
| 5,035,893 | 7/1991 | Shioya et al. | 424/447 |
| 5,037,749 | 8/1991 | Findlay | 435/176 |
| 5,039,660 | 8/1991 | Leonard et al. | 514/8 |
| 5,051,272 | 9/1991 | Hermes et al. | 427/2 |
| 5,059,123 | 10/1991 | Jernberg | 433/215 |
| 5,077,049 | 12/1991 | Dunn et al. | 424/426 |
| 5,080,665 | 1/1992 | Jarrett et al. | 606/219 |
| 5,081,106 | 1/1992 | Bentley et al. | 514/5 |
| 5,084,051 | 1/1992 | Tömälä et al. | 606/77 |
| 5,103,840 | 4/1992 | Kavoussi | 128/899 |
| 5,106,626 | 4/1992 | Parsons et al. | 424/423 |
| 5,106,748 | 4/1992 | Wozney et al. | 435/252.3 |
| 5,108,753 | 4/1992 | Kuberasampath et al. | 424/422 |
| 5,108,755 | 4/1992 | Daniels et al. | 424/426 |
| 5,108,922 | 4/1992 | Wang et al. | 435/240.2 |
| 5,110,604 | 5/1992 | Chu et al. | 424/484 |
| 5,116,738 | 5/1992 | Wang et al. | 435/69.1 |
| 5,118,667 | 6/1992 | Adams et al. | 514/12 |
| 5,120,322 | 6/1992 | Davis et al. | 604/265 |
| 5,124,155 | 6/1992 | Reich | 424/428 |
| 5,128,136 | 7/1992 | Bentley et al. | 424/443 |
| 5,128,326 | 7/1992 | Balazs et al. | 514/54 |
| 5,133,755 | 7/1992 | Brekke | 623/16 |
| 5,137,669 | 8/1992 | Leonard et al. | 264/120 |
| 5,141,905 | 8/1992 | Rosen et al. | 435/69.1 |
| 5,143,730 | 9/1992 | Fues et al. | 424/426 |
| 5,149,691 | 9/1992 | Rutherford | 514/12 |
| 5,162,114 | 11/1992 | Kuberasampath et al. | 424/423 |
| 5,162,430 | 11/1992 | Rhee et al. | 525/54.1 |
| 5,164,368 | 11/1992 | Recker | 514/12 |
| 5,166,058 | 11/1992 | Wang et al. | 435/69.1 |
| 5,168,050 | 12/1992 | Hammond, Jr. et al. | 435/69.1 |
| 5,171,217 | 12/1992 | March et al. | 604/53 |
| 5,171,574 | 12/1992 | Kuberasampath et al. | 424/423 |
| 5,171,579 | 12/1992 | Ron et al. | 424/486 |
| 5,171,670 | 12/1992 | Kronenberg et al. | 435/68.1 |
| 5,182,365 | 1/1993 | Opperman et al. | 530/326 |
| 5,185,152 | 2/1993 | Peyman | 424/427 |
| 5,187,076 | 2/1993 | Wozney et al. | 435/69.1 |
| 5,192,741 | 3/1993 | Orsolini et al. | 514/4 |
| 5,196,185 | 3/1993 | Silver et al. | 424/45 |
| 5,197,977 | 3/1993 | Hoffman, Jr. et al. | 623/1 |
| 5,206,028 | 4/1993 | Li | 424/484 |
| 5,208,041 | 5/1993 | Sindrey | 424/562 |
| 5,208,219 | 5/1993 | Ogawa et al. | 514/12 |
| 5,223,263 | 6/1993 | Hostetler et al. | 424/450 |
| 5,227,157 | 7/1993 | McGinity et al. | 424/78.02 |
| 5,250,302 | 10/1993 | Oppermann et al. | 424/422 |
| 5,250,584 | 10/1993 | Ikada et al. | 523/114 |
| 5,258,494 | 11/1993 | Opperman et al. | 530/326 |
| 5,263,985 | 11/1993 | Bao et al. | 623/16 |
| 5,264,618 | 11/1993 | Felgner et al. | 560/224 |
| 5,266,683 | 11/1993 | Oppermann et al. | 530/326 |
| 5,268,178 | 12/1993 | Calhoun et al. | 424/426 |
| 5,270,300 | 12/1993 | Hunziker | 514/12 |
| 5,271,961 | 12/1993 | Mathiowitz et al. | 427/213.31 |
| 5,273,964 | 12/1993 | Lemons | 514/2 |
| 5,275,826 | 1/1994 | Badylak et al. | 424/551 |
| 5,278,201 | 1/1994 | Dunn et al. | 523/113 |
| 5,278,202 | 1/1994 | Dunn et al. | 523/113 |
| 5,281,419 | 1/1994 | Tuan et al. | 424/426 |
| 5,281,422 | 1/1994 | Badylak et al. | 424/551 |
| 5,286,634 | 2/1994 | Stadler et al. | 435/172.3 |
| 5,288,496 | 2/1994 | Lewis | 424/426 |
| 5,292,802 | 3/1994 | Rhee et al. | 525/54.1 |
| 5,304,121 | 4/1994 | Sahatjian | |
| 5,306,303 | 4/1994 | Lynch | 623/16 |
| 5,308,623 | 5/1994 | Fues et al. | 424/426 |
| 5,308,889 | 5/1994 | Rhee et al. | 523/113 |
| 5,317,010 | 5/1994 | Pang et al. | 514/12 |
| 5,320,624 | 6/1994 | Kaplan et al. | 606/77 |
| 5,324,307 | 6/1994 | Jarrett et al. | 606/219 |
| 5,324,519 | 6/1994 | Dunn et al. | 424/426 |
| 5,324,520 | 6/1994 | Dunn et al. | 424/435 |
| 5,324,775 | 6/1994 | Rhee et al. | 525/54.2 |
| 5,324,819 | 6/1994 | Oppermann et al. | 530/350 |
| 5,326,350 | 7/1994 | Li | 623/11 |
| 5,326,357 | 7/1994 | Kandel | 623/16 |
| 5,328,955 | 7/1994 | Rhee et al. | 525/54.1 |
| 5,344,654 | 9/1994 | Rueger et al. | 424/423 |
| 5,350,580 | 9/1994 | Muchow et al. | 424/437 |
| 5,352,463 | 10/1994 | Badylak et al. | 424/551 |
| 5,354,557 | 10/1994 | Oppermann et al. | 424/423 |
| 5,360,610 | 11/1994 | Tice et al. | 424/426 |
| 5,366,508 | 11/1994 | Brekke | 623/16 |
| 5,366,733 | 11/1994 | Brizzolara et al. | 424/426 |
| 5,366,734 | 11/1994 | Hutchinson | 424/426 |
| 5,366,875 | 11/1994 | Wozney et al. | 435/69.1 |
| 5,372,821 | 12/1994 | Badylak et al. | 424/551 |
| 5,374,431 | 12/1994 | Pang et al. | 424/486 |
| 5,376,636 | 12/1994 | Rutherford et al. | 514/12 |
| 5,378,451 | 1/1995 | Gorman et al. | 424/47 |
| 5,378,540 | 1/1995 | Olson | 428/394 |
| 5,399,677 | 3/1995 | Wolfman et al. | 536/23.5 |
| 5,445,833 | 8/1995 | Badylak et al. | 424/551 |
| 5,459,047 | 10/1995 | Wozney et al. | 435/69.1 |
| 5,460,831 | 10/1995 | Kossovsky | |
| 5,464,650 | 11/1995 | Berg et al. | |
| 5,470,829 | 11/1995 | Prisell et al. | 514/12 |
| 5,474,797 | 12/1995 | Sioshansi et al. | 427/2.24 |
| 5,494,806 | 2/1996 | Segre et al. | 435/69.1 |
| 5,496,552 | 3/1996 | Kuberasampath | 424/420 |
| 5,543,394 | 8/1996 | Wozney et al. | 514/12 |
| 5,589,466 | 12/1996 | Felgner et al. | 514/44 |
| 5,618,924 | 4/1997 | Wang et al. | 530/399 |
| 5,631,142 | 5/1997 | Wang et al. | 435/69.1 |
| 5,635,372 | 6/1997 | Celeste et al. | 435/69.1 |
| 5,635,373 | 6/1997 | Wozney et al. | 435/69.1 |
| 5,637,480 | 6/1997 | Celeste et al. | 435/69.4 |
| 5,639,638 | 6/1997 | Wozney et al. | 435/69.4 |
| 5,652,118 | 7/1997 | Ozkaynak et al. | 435/69.1 |
| 5,652,337 | 7/1997 | Oppermann et al. | 530/350 |
| 5,656,593 | 8/1997 | Kuberasampath et al. | 514/12 |
| 5,658,882 | 8/1997 | Celeste et al. | 514/12 |
| 5,661,007 | 8/1997 | Wozney et al. | 435/69.4 |

| | | |
|---|---|---|
| 5,670,336 | 9/1997 | Oppermann et al. ............... 435/69.1 |
| 5,674,703 | 10/1997 | Woo et al. . |
| 5,674,844 | 10/1997 | Kuberasampath et al. ............ 514/12 |
| 5,688,678 | 11/1997 | Hewick et al. .................. 435/240.2 |
| 5,700,774 | 12/1997 | Hattersley et al. ..................... 514/2 |
| 5,700,911 | 12/1997 | Wozney et al. ..................... 530/350 |
| 5,703,043 | 12/1997 | Celeste et al. ........................ 514/12 |
| 5,707,969 | 1/1998 | Nabel et al. . |
| 5,770,580 | 6/1998 | Ledley et al. . |

FOREIGN PATENT DOCUMENTS

| | | |
|---|---|---|
| WO92/07004 | 4/1992 | WIPO . |
| WO 92/07573 | 5/1992 | WIPO . |
| 9215676 | 9/1992 | WIPO . |
| WO92/15323 | 9/1992 | WIPO . |
| WO92/15676 | 9/1992 | WIPO . |
| WO 92/17165 | 10/1992 | WIPO . |
| WO 93/05751 | 1/1993 | WIPO . |
| WO 93/09229 | 5/1993 | WIPO . |
| WO 93/14778 | 8/1993 | WIPO . |
| WO 93/15109 | 8/1993 | WIPO . |
| WO 93/16739 | 9/1993 | WIPO . |
| 9319660 | 10/1993 | WIPO . |
| WO 93/21969 | 11/1993 | WIPO . |
| 9401557 | 1/1994 | WIPO . |
| WO 94/01139 | 1/1994 | WIPO . |
| WO94/03600 | 2/1994 | WIPO . |
| WO94/06399 | 3/1994 | WIPO . |
| WO94/06447 | 3/1994 | WIPO . |
| WO94/06449 | 3/1994 | WIPO . |
| WO94/10203 | 5/1994 | WIPO . |
| WO 94/20615 | 9/1994 | WIPO . |
| WO 94/23738 | 10/1994 | WIPO . |
| WO 95/18856 | 7/1995 | WIPO . |
| WO95/30003 | 11/1995 | WIPO . |
| WO95/33502 | 12/1995 | WIPO . |
| WO 96/07924 | 6/1996 | WIPO . |
| WO 96/16668 | 6/1996 | WIPO . |
| WO 97/11095 | 3/1997 | WIPO . |

OTHER PUBLICATIONS

Colosetti, et al., "Axotomy of Rat Facial Nerve Induces TGF–$\beta$ and Latent TGF–$\beta$ Binding Protein," *Brain Research Bulletin* 37(6):561–67, 1995.

Dallas, et al., "Characterization and Autoregulation of Latent Transforming Growth Factor $\beta$(TGF$\beta$) Complexes in Osteoblast–like Cell Lines," *The Journal of Biological Chemistry*, 269(9):6815–22, 1994.

Eklöv, et al., "Lack of the Latent Transforming Growth Factor $\beta$ Binding Protein in Malignant, but not Benigh Prostatic Tissue," *Cancer Research*, 53:3193–97, 1993.

Flaumenhaft, "Extracellular Regulation of Basic Fibroblast Growth Factor and Transforming Growth Factor–Beta Activity," *Dissertation Abstracts International*, 53(3):1340B, 1992. (abstract).

Kogawa et al., "[TGF–beta and Platelet]", *Rinsho Ketsueki*, 35(4):370–5, 1994 (abstract).

Koli, "Growth–Inhibitory Effects of Transforming Growth Factor–beta and 1,25–dihydroxyvitamin D(3) on Cultured Epithelial Cells: Relationships to Plasminogen Activation," *Diss. Abstr. Int*, 56(3):629, 1995.

Li, et al., "Mapping of Human and Murine Genes for Latent TGF–$\beta$ Binding Protein–2 (LTBP2)," *Mammalian Genome* 6:42–45, 1995.

Maeda, et al., "Local Production and Localization of Transforming Growth Factor–beta in Tuberculous Pleurisy," *Clin. Exp. Immunol.*, 92:32–38, 1993.

Miyazono, et al., "Structure and Function of Latent Forms of Tranforming Growth Factor–beta (Meeting abstract)," *Seventh International Conference of the International Society of Differentiation, Cellular Programmes for Growth Differentiation and Neoplasia*, (1992):58, 1992.

Mizoi, et al. "Immunohistochemical Identification of Transforming Growth Factor–beta and Its Binding Protein in Human Gastrointestinal Carcinoma," *Tojoku J. Exp. Med.*, 168(2):271–3, 1992. (abstract).

Mizoi, et al., "Immunoelectron Microscopic Localization of Transforming Growth Factor$_1$ and Latent Transforming Growth Factor $\beta_1$ Binding Protein in Human Gastrointestinal Carcinomas: Qualitative Difference Between Cancer Cells and Stromal Cells," *Cancer Research*, 53:183–190, 1993.

Rifkin, "TGF–$\beta$ Formation; Mechanisms and Consequences," *J. Cellular Biochem.* Suppl. 19B, 3, 1995.

Taipale, et al., "Control of TGF–beta 1, Its Latent Form Binding Protein (LTBP) and Typ0e II Receptor Expression During Differentiation of Human Myeloid Leukemia Cells Lines (Meeting Abstract)," *EACR–12: 12th Biennial Meeting of the European Association for Cancer Research*, 1993.

Tamaki et al., "TGF–$\beta$1 in Glomerulosclerosis and Interstitial Fibrosis of Adriamycin Nephropathy," *Kidney International*, 45:525–36, 1994.

Van Laethem, et al., "Localization of Transforming Growth Factor $\beta$1 and Its Latent Binding Protein in Human Chronic Pancreatitis," *Gastroenterology* 108:1873–81, 1995.

Vilafranca, et al., "Muscle Fibre Expression of Transforming Growth Factor–beta 1 and Latent Transforming Growth Factor–beta Binding Protein in Canine Masticatory Muscle Myositis," *J. Comp. Pathol.* 112(3):299–306, 1995.

Waltenberger, et al., "Involvement of Transforming Growth Factor–$\beta$ in the Formation of Fibrotic Lesions in Carcinoid Heart Disease," *American Journal of Pathology*, 142(1):71–8, 1993.

Waltenberger, et al., "Induction of Transforming Growth Factor–$\beta$ during Cardiac Allograft Rejection," *The Journal of Immunology*, 151(2):1147–57, 1993.

Badylak et al., "Directed Connective Tissue Remodeling Upon a Biologic Collagen Substrate," *J. Cell Biochem. Supplement 16F*, p. 124, Apr. 3–16, 1992.

Benevisty and Reshef, "Direct introduction of genes into rats and expression of the genes," *Proc. Natl. Acad. Sci. USA*, 83:9551–9555, Dec. 1986.

Bonadio and Goldstein, "Direct Gene Transfer into Skeletal Tissues In Vivo," *Gene Therapy Meeting; Cold Spring Harbor*, Conference Abstract, Sep. 21–25, 1994.

Edelman et al., "c–myc in Vasculoproliferative Disease, "*Circulation Research*, 76(2):1.2–1.8, Feb., 1995.

Evans and Robbins, "Possible Orthopaedic Applications of Gene Therapy," *The Journal of Bone and Joint Surgery*, 77–A(7):1103–1114, Jul., 1995.

Indolfi et al., "Inhibition of cellular ras prevents smooth muscle cell proliferation after vascular injury in vivo," *Nature Medicine*, 1(6):541–545, Jun., 1995.

Invention Disclosure entitled "Small Intestinal Submucosa as Biomaterial to Promote Gene Transfer," Stephen G. Badylak, Jeffrey Bonadio and Sherry L. Voytik, Sep. 4, 1992.

Kaneda et al., "Increased Expression of DNA Cointroduced with Nuclear Protein in Adult Rat Liver," *Science*, 243:375–378, Jan., 1989.

Mannino and Gould–Fogerite, "Liposome Mediated Gene Transfer," *BioTechniques*, 6(7):682–690, 1988.

Mumper et al., "Interactive Polymeric Gene Delivery Systems for Enhanced Muscle Expression," *Abstract*, American Assoc. of Pharmaceutical Science, Miami Beach, FL, Nov. 6–9, 1995.

Nicolau et al., "In vivo expression of rat insulin after intravenous administration of the liposome–entrapped gene for rat insulin I," *Proc. Natl. Acad. Sci. USA*, 80:1068–1072, Feb., 1983.

Simons et al., "Antisense c–myb oligonucleotides inhibit intimal arterial smooth muscle cell accumulation in vivo," *Nature*, 359:67–70, Sep., 1992.

Sumner et al., "Enhancement of Bone Ingrowth by Transforming Growth Factor–β, " *The Journal of Bone and Joint Surgery*, 77–A(8):1135–1147, Aug., 1995.

Wolff et al., "Conditions Affecting Direct Gene Transfer into Rodent Muscle In Vivo," *BioTechniques*, 11(4): 474–485, 1991.

Wolff et al., "Expression of naked plasmids by cultured myotubes and entry of plasmids into T tubules and caveolae of mammalian skeletal muscle," *Journal of Cell Science*, 103:1249–1259, 1992.

Wu and Wu, "Receptor–mediated Gene Delivery and Expression in Vivo," *The Journal of Biological Chemistry*, 263(29):14621–14624, 1988.

Yin et al., "Molecular Cloning of a Novel Fibrillin–Like cDNA: Expression in Callus Tissue as Alternatively Spliced Transcripts," *40th Annual Meeting, Orthopaedic Research Society*, Conference Abstract, Feb. 21–24, 1994.

Zhu et al., "Direct Gene Transfer into Regenerating Achilles' Tendon," *40th Annual Meeting, Orthopaedic Research Society*, Conference Abstract, Feb. 21–24, 1994.

U.S. Patent Application Serial No. 08/176,565; filed Jan. 3, 1994; entitled "Fluidized Intestinal Submucosa and its Use as an Injectable Tissue Graft".

U.S. Patent Application Serial No. 08/343,204; filed Nov. 22, 1994; entitled "Fluidized Intestinal Submucosa and its Use as an Injectable Tissue Graft".

U.S. Patent Application Serial No. 08/390,700; filed Feb. 17, 1995; entitled "Compositions and Method for Production of Transformed Cells".

U.S. Patent Application Serial No. 08/386,432; filed Feb. 10, 1995; entitled "Bone Graft Composition".

U.S. Patent Application Serial No. 08/386,452; filed Feb. 10, 1995; entitled "Submucosa as a Growth Substrate for Cells".

Rosen and Thies, "The BMP proteins in bone formation and repair," *Trends in Genetics*, 8(3) :97–102, Mar., 1992.

International Search Report dated Sep. 15, 1995.

Alper, "Boning Up: Newly Isolated Proteins Heal Bad Breaks", *Science*, 263:324–325, 1994.

Bandara, G., et al., "Gene Transfer to Synoviocytes: Prospects for Gene Treatment of Arthritis", *DNA and Cell Biology*, 11(3) :227–231, 1992.

Beck, L. Steven, et al., "Rapid Publication TGF–$\beta_1$ Induces Bone Closure of Skull Defects", *J. Bone Miner. Res.*, 6(11) :1257–1265, 1991.

Boden, S.D., et al., "Estrogen Receptor mRNA Expression in Callus During Fracture Healing in the Rat", *Calcif Tissue Int*, 45:324–325, 1989.

Bonnarens and Einhorn, "Production of a Standard Closed Fracture in Laboratory Animal Bone", *J. Orthrop. Res.*, 2:97–101, 1984.

Carrinton, Jill L., et al., "Accumulation, Localization, and Compartmentation of Transforming Growth Factor β During Endochondral Bone Development", *J. Cell Biol.*, 107:1969–1975, 1988.

Centrella, Michael et al., "Skeletal Tissue and Transforming Growth Factor β", *FASEB J.*, 2:3066–3073, 1988.

Chen, Theresa L., et al., "Bone Morphogenetic Protein–2b Stimulation of Growth and Osteogenic Phenotypes in Rat Osteoblast–like Cells: Comparison with TGF–$\beta_1$", *J. Bone Miner. Res.*, 6(12) :1387–1393, 1991.

Cunningham, Noreen S., et al., "Osteogenin and Recombinant Bone Morphogenetic Protein 2B are Chemotactic for Human Monocytes and Stimulate Transforming Growth Factor $\beta_1$ mRNA Expression", *Proc. Natl. Acad. Sci. USA*, 89:11740–11744, 1992.

Gunasekaran, S, et al., "Mineralized Collagen as a Substitute for Autograft Bone that Can Deliver Bone Morphogenic Protein", *The 19th Annual Meeting of the Society for Biomaterials*, p. 253, 1993.

Gunasekaran, S., et al., "Role of Mineralized Collagen as an Osteoconductive Biomaterial", *the 19th Annual Meeting of the Society for Biomaterials*, p. 161, 1993.

Gunasekaran, S., et al., "Mineralization of Collagen Without Nucleating Proteins", 11:30 A.M. V7.5, p. 426.

Horowitz, Mark C., et al., "Functional and Molecular Changes in Colony Stimulating Factor Secretion by Osteoblasts", *Connective Tissue Research*, 20:159–168, 1989.

Huggins, C.B., et al., "Experiments on the Theory of Osteogenesis", *Arch. Surg.*, 32(6):915–931, 1936.

Izumi, Toshihiro, et al., "Transforming Growth Factor $\beta_1$ Stimulates Type II Collagen Expression in Cultured Periosteum–Derived Cells", *J. Bone Miner. Res.*, 7(1):115–121, 1992.

Jingushi, Seiya, et al., "Genetic Expression of Extracellular Matrix Proteins Correlates with Histologic Changes During Fracture Repair", *J. Bone Miner. Res.*, 7(9):1045–1055, 1992.

Jingushi, S., et al., "Acidic Fibroblast Growth Factor (aFGF) Injection Stimulates Cartilage Enlargement and Inhibits Cartilage Gene Expression in Rat Fracture Healing", *J. Orthop. Res.*, 8:364–371, 1990.

Joyce, Michael E., et al., "Role of Growth Factors in Fracture Healing", *Clinical and Experimental Approaches to Dermal and Epidermal Repair: Normal and Chronic Wounds*, 391–416, 1991.

Joyce, Michael E., et al., "Transforming Growth Factor–β and the Initiation of Chondrogenesis and Osteogenesis in the Rat Femur", *The J. Cell Biol.*, 110:2195–2207, 1990.

Luyten, Frank P., et al., "Purification and Partial amnio Acid Sequence of Osteogenin, a Protein Initiating Bone Differentiation", *J. Biol. Chem.*, 264(23):13377–13380, 1989.

O'Malley, Jr. and Ledley "Somatic Gene Therapy in Otolaryngology–Head and Neck Surgery", *Arch Otolaryngol Head Neck Surg*, 119:1191–1197, 1993.

Ozkaynak, Engin, et al., "OP–1 cDNA Encodes an Osteogenic Protein in the TGF–β Family", *EMBO J.*, 9 (7):2085–2093, 1990.

Paralkar, Vishwas M., et al., "Identification and Characterization of Cellular Binding Proteins (Receptors) for Recombinant Human Bone Morphogenetic Protein 2B, an Initiator of Bone Differentiation Cascade", *Proc. Natl. Acad. Sci. USA*, 88:3397–3401, 1991.

Roessier, Blake J., et al., "Adenoviral–mediated Gene Transfer to Rabbit Synovium In Vivo", *J. Clin. Invest.*, 92:1085–1092, 1993.

Rosen, Vicki, et al., "Purification and Molecular Cloning of a Novel Group of BMPS and Localization of BMP mRNA in Developing Bone", *Connect. Tissue Res.*, 20:313–319, 1989.

Sampath, T.K., et al., "In Vitro Transformation of Mesenchymal Cells Derived From Embryonic Muscle into Cartilage in Response to Extracellular Matrix Components of Bone", *Proc. Natl. Acad. Sci. USA*, 81:3419–3423, 1984.

Sampath and Reddi, "Dissociative Extraction and Reconstitution of Extracellular Matrix Components Involved in Local Bone Differentiation", *Proc. Natl. Acad. Sci. USA*, 78 (12):7599–7603, 1981.

Sandusky, G.E., Jr. et al., "Histologic Findings After In Vivo Placement of Small Intestine Submucosal Vascular Grafts and Saphenous Vein Grafts in the Carotid Artery in Dogs", *American Journal of Pathology*, 140 (2):317–324, 1992.

Shimell, Mary Jane, et al., "The Drosophila Dorsal–Ventral Patterning Gene tolloid is Related to Human Bone Morphogenetic Protein 1", *Cell*, 67:469–481, 1991.

Srivastave, Carolyn H., et al., "Construction of a Recombinant Human Parvovirus B19: Adenoasociated Virus 2 (AAV) DNA Inverted Terminal Repeats are Functional in an AAV–B19 Hybrid Virus", *Proc. Natl. Acad. Sci. USA*, 86:8078–8082, 1989.

Toriumi, Dean M., et al., "Mandibular Reconstruction With a Recombinant Bone–Inducing Factor", *Arch Otolaryngol Head Neck Surg*, 117:1101–1112, 1991.

Ulmer, Jeffrey B. et al., "Heterologous Protection Against Influenza by Injection of DNA Encoding a Viral Protein", *Science*, 259:1745–1749, 1993.

Urist, Marshall R., et al., "Bone Cell Differentiation Growth Factors", *Science*, 220:680–220, 1983.

Urist, Marshall R., "Bone: Formation by Autoinduction", *Science*, 150:893–899, 1965.

Wang, Elizabeth A., et al., "Recombinant Human Bone Morphogenetic Protein Induces Bone Formation", *Proc. Natl. Acad. Sci. USA*, 87:2220–2224, 1990.

Wilson, James M., et al., "Somatic Gene Transfer in the Development of an Animal Model for Primary Hyperparathyroidism", *Endocrinology*, 130(5):2947–2954, 1992.

Wolff, Jon A., et al., "Direct Gene Transfer into Mouse Muscle In Vivo", *Science*, 247:1465–1468, 1990.

Wozney, John M., et al., "Novel Regulators of Bone Formation: Molecular Clones and Activities", *Science*, 242:1528–1534, 1988.

Yasko, Alan W., et al., "The Healing of Segmental Bone Defects, Induced by Recombinant Human Bone Morphogenetic Protein (rhBMP–2)", *The Journal of Bone and Joint Surgery*, 74–A(5):659–670, 1992.

Agarwala, Neena, et al., "Specific Binding of Parathyroid Hormone to Living Osteoclasts", *Journal of Bone and Mineral Research*, 7:531–539, 1992.

Bonadio et al., "Transgenic mouse model of the mild dominant form of osteogenesis imperfecta," *Proc. Natl. Acad. Sci. USA*, 87:7145–7149, 1990.

Davidson et al., "A model system for in vivo gene transfer into the central nervous system using an adenviral vector," *Nature Genetics*, 3:219–223, 1993.

Falcone et al., "Macrophage and Foam Cell Release of Matrix–bound Growth Factors," *The Journal of Biological Chemistry*, 268 (15):11951–11958, 1993.

Flaumenhaft et al., "Role of the Latent TGF–β Binding Protein in the Activation of Latent TGF–β by Co–Cultures of Endothelial and Smooth Muscle Cells," *The Journal of Cell Biology*, 120 (4) :995–1002, 1993.

Majmudar et al., "Bone Cell Culture in a Three–Dimensional Polymer Bead Stabilizers the Differentiated Phenotype and Provides Evidence That Osteoblastic Cells Synthesize Type III Collagen and Fibronectin," *Journal of Bone and Mineral Research*, 6 (8):869–881, 1991.

Miyazono et al., "Retention of the Transforming Growth Factor–β1 Precursor in the Golgi Complex in a Latent Endoglycosidase H–sensitive Form," *The Journal of Biological Chemistry*, 267(8):5668–5675, 1992.

Pereira et al., "Genomic organization of the sequence coding for fibrillin, the defective gene product in Marfan syndrome," *Human Molecular Genetics*, 2 (7):961–968, 1993.

Seitz et al., "Effect of Transforming Growth Factor β on Parathyroid Hormone Receptor Binding and cAMP Formation in Rat Osteosarcoma Cells", *Journal of Bone and Mineal Research*, 7:541–546, 1992.

Selander–Sunnerhagen et al., "How an Epidermal Growth Factor (EGF)–like Domain Binds Calcium," *The Journal of Biological Chemistry*, 267 (27):19642–19649, 1992.

Steiner et al., "The New Enzymology of Precursor Processing Endoproteases," *The Journal of Biological Chemistry*, 267 (33):23435–23438, 1992.

Stratford–Perricaudet et al., "Widespread Long–term Gene Transfer to Mouse Skeletal Muscles and Heart," *J. Clin. Invest.*, 90:626–630, 1992.

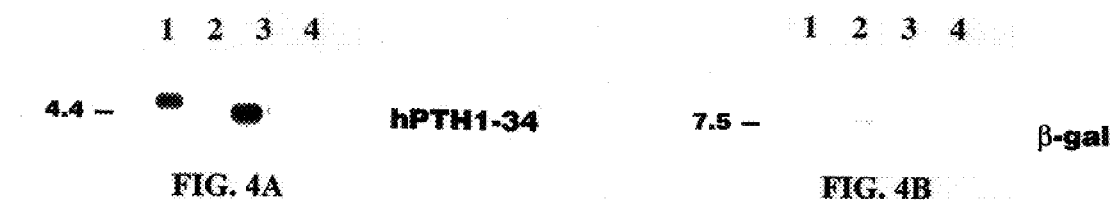
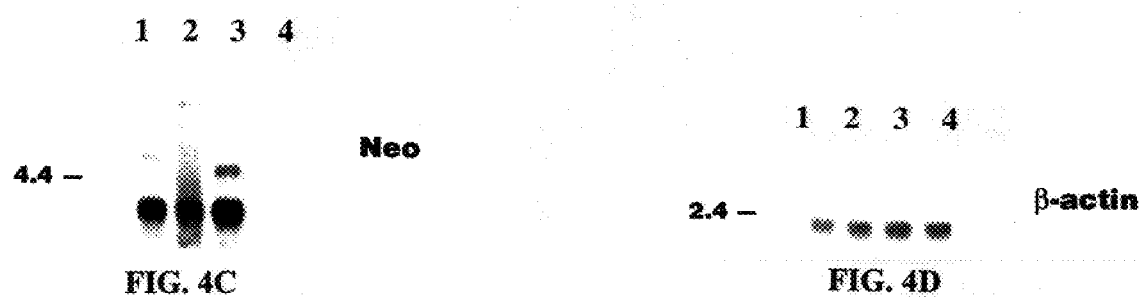

```
MIPGNRMLMV  VLLCQVLLGG  ATDASLMPET  GKKKVAEIQG  HAGGRRSGQS  HELLRDFEAT  LLQMFGLRRR
PQPSKSAVIP  DYMSDLYRLQ  SGEEEEEQS   QGTGLEYPER  PASSANTVSS  FHHEEHLENI  PGTSESSAFR
FFFNLSSIPE  NEVISSAELR  LFREQVDQGP  DWEQGFHRMN  IYEVMKPPAE  MVPGHLITRL  LDTSLVRHNV
TRWETFDVSP  AVLRWTREKQ  PNYGLAIEVT  HLHQTRTHQG  QHVSISRSLP  QGSGNWAQLR  PLLVTFGHDG
RGHTLTRRSA  KRSPKHHPQR  SSKKNKNCRR  HSLYVDFSDV  GWNDWIVAPP  GYQAFYCHGD  CPFPLADHLN
STNHAIVQTL  VNSVNSSIPK  ACCVPTELSA  ISMLYLDEYD  KVVLKNYQEM  VVEGCGCRYP  YDVPDYA

SEQ ID NO:1
```

FIG. 9

SEQUENCE LISTING (1) GENERAL INFORMATION:

(iii) NUMBER OF SEQUENCES: 15

(2) INFORMATION FOR SEQ ID NO:1:

(i) SEQUENCE CHARACTERISTICS:
    (A) LENGTH: 417 amino acids
    (B) TYPE: amino acid
    (C) STRANDEDNESS: single
    (D) TOPOLOGY: linear (ii) MOLECULE TYPE: protein (xi) SEQUENCE DESCRIPTION: SEQ ID NO:1:

```
Met Ile Pro Gly Asn Arg Met Leu Met Val Val Leu Leu Cys Gln Val
1               5                   10                  15

Leu Leu Gly Gly Ala Thr Asp Ala Ser Leu Met Pro Glu Thr Gly Lys
            20                  25                  30

Lys Lys Val Ala Glu Ile Gln Gly His Ala Gly Gly Arg Arg Ser Gly
        35                  40                  45

Gln Ser His Glu Leu Leu Arg Asp Phe Glu Ala Thr Leu Leu Gln Met
    50                  55                  60

Phe Gly Leu Arg Arg Arg Pro Gln Pro Ser Lys Ser Ala Val Ile Pro
65                  70                  75                  80

Asp Tyr Met Ser Asp Leu Tyr Arg Leu Gln Ser Gly Glu Glu Glu Glu
                85                  90                  95

Glu Glu Gln Ser Gln Gly Thr Gly Leu Glu Tyr Pro Glu Arg Pro Ala
                100                 105                 110

Ser Ser Ala Asn Thr Val Ser Ser Phe His His Glu Glu His Leu Glu
            115                 120                 125

Asn Ile Pro Gly Thr Ser Glu Ser Ser Ala Phe Arg Phe Phe Phe Asn
    130                 135                 140

Leu Ser Ser Ile Pro Glu Asn Glu Val Ile Ser Ser Ala Glu Leu Arg
145                 150                 155                 160

Leu Phe Arg Glu Gln Val Asp Gln Gly Pro Asp Trp Glu Gln Gly Phe
                165                 170                 175

His Arg Met Asn Ile Tyr Glu Val Met Lys Pro Pro Ala Glu Met Val
                180                 185                 190

Pro Gly His Leu Ile Thr Arg Leu Leu Asp Thr Ser Leu Val Arg His
            195                 200                 205

Asn Val Thr Arg Trp Glu Thr Phe Asp Val Ser Pro Ala Val Leu Arg
210                 215                 220

Trp Thr Arg Glu Lys Gln Pro Asn Tyr Gly Leu Ala Ile Glu Val Thr
225                 230                 235                 240

His Leu His Gln Thr Arg Thr His Gln Gly Gln His Val Ser Ile Ser
                245                 250                 255

Arg Ser Leu Pro Gln Gly Ser Gly Asn Trp Ala Gln Leu Arg Pro Leu
            260                 265                 270

Leu Val Thr Phe Gly His Asp Gly Arg Gly His Thr Leu Thr Arg Arg
            275                 280                 285

Ser Ala Lys Arg Ser Pro Lys His His Pro Gln Arg Ser Ser Lys Lys
        290                 295                 300

Asn Lys Asn Cys Arg Arg His Ser Leu Tyr Val Asp Phe Ser Asp Val
305                 310                 315                 320

Gly Trp Asn Asp Trp Ile Val Ala Pro Pro Gly Tyr Gln Ala Phe Tyr
                325                 330                 335

Cys His Gly Asp Cys Pro Phe Pro Leu Ala Asp His Leu Asn Ser Thr
            340                 345                 350

Asn His Ala Ile Val Gln Thr Leu Val Asn Ser Val Asn Ser Ser Ile
        355                 360                 365
```

```
Pro Lys Ala Cys Cys Val Pro Thr Glu Leu Ser Ala Ile Ser Met Leu
    370             375                 380

Tyr Leu Asp Glu Tyr Asp Lys Val Val Leu Lys Asn Tyr Gln Glu Met
385                 390                 395                 400

Val Val Glu Gly Cys Gly Cys Arg Tyr Pro Tyr Asp Val Pro Asp Tyr
                405                 410                 415

Ala
```

(2) INFORMATION FOR SEQ ID NO:2:

(i) SEQUENCE CHARACTERISTICS:
        (A) LENGTH: 4314 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 157..3912

(xi) SEQUENCE DESCRIPTION: SEQ ID NO:2:

```
CCTCCTGCTG TCCCCTCCCT ACCCTTGGCT TCTCGCCCCG CTCTGCCCTC TGCTACCAAC      60

ACTCGATCCC CTGCTCGGGC TCGACCTCCA ATCTCCGAGG GTCGTGCGGC CCCGGATGCC     120

CGGGCCCCGA GCGGTGCCCA CGGCCTGGCC CCTGCG ATG CGC CAG GCC GGC GGA      174
                                    Met Arg Gln Ala Gly Gly
                                     1               5

TTG GGG CTG CTG GCA CTA CTC CTG CTG GCG CTG CTG GGC CCC GGC GGC      222
Leu Gly Leu Leu Ala Leu Leu Leu Leu Ala Leu Leu Gly Pro Gly Gly
             10                  15                  20

CGA GGG GTG GGC CGG CCG GGC AGC GGG GCA CAG GCG GGG GCG GGG CGC      270
Arg Gly Val Gly Arg Pro Gly Ser Gly Ala Gln Ala Gly Ala Gly Arg
         25                  30                  35

TGG GCC CAA CGC TTC AAG GTG GTC TTT GCG CCT GTG ATC TGC AAG CGG      318
Trp Ala Gln Arg Phe Lys Val Val Phe Ala Pro Val Ile Cys Lys Arg
     40                  45                  50

ACC TGT CTG AAG GGC CAG TGT CGG GAC AGC TGT CAG CAG GGC TCC AAC      366
Thr Cys Leu Lys Gly Gln Cys Arg Asp Ser Cys Gln Gln Gly Ser Asn
 55                  60                  65                  70

ATG ACG CTC ATC GGA GAG AAC GGC CAC AGC ACC GAC ACG CTC ACC GGT      414
Met Thr Leu Ile Gly Glu Asn Gly His Ser Thr Asp Thr Leu Thr Gly
                 75                  80                  85

TCT GCC TTC CGC GTG GTG GTG TGC CCT CTA CCC TGC ATG AAC GGT GGC      462
Ser Ala Phe Arg Val Val Val Cys Pro Leu Pro Cys Met Asn Gly Gly
             90                  95                 100

CAG TGC TCT TCC CGA AAC CAG TGC CTG TGT CCC CCG GAT TTC ACG GGG      510
Gln Cys Ser Ser Arg Asn Gln Cys Leu Cys Pro Pro Asp Phe Thr Gly
        105                 110                 115

CGC TTC TGC CAG GTG CCT GCT GCA GGA ACC GGA GCT GGC ACC GGG AGT      558
Arg Phe Cys Gln Val Pro Ala Ala Gly Thr Gly Ala Gly Thr Gly Ser
    120                 125                 130

TCA GGC CCC GGC TGG CCC GAC CGG GCC ATG TCC ACA GGC CCG CTG CCG      606
Ser Gly Pro Gly Trp Pro Asp Arg Ala Met Ser Thr Gly Pro Leu Pro
135                 140                 145                 150

CCC CTT GCC CCA GAA GGA GAG TCT GTG GCT AGC AAA CAC GCC ATT TAC      654
Pro Leu Ala Pro Glu Gly Glu Ser Val Ala Ser Lys His Ala Ile Tyr
                155                 160                 165

GCG GTG CAG GTG ATC GCA GAT CCT CCC GGG CCG GGG GAG GGT CCT CCT      702
Ala Val Gln Val Ile Ala Asp Pro Pro Gly Pro Gly Glu Gly Pro Pro
            170                 175                 180
```

```
GCA CAA CAT GCA GCC TTC TTG GTG CCC CTG GGG CCA GGA CAA ATC TCG         750
Ala Gln His Ala Ala Phe Leu Val Pro Leu Gly Pro Gly Gln Ile Ser
        185                 190                 195

GCA GAA GTG CAG GCT CCG CCC CCC GTG GTG AAC GTG CGT GTC CAT CAC         798
Ala Glu Val Gln Ala Pro Pro Pro Val Val Asn Val Arg Val His His
200                 205                 210

CCT CCT GAA GCT TCC GTT CAG GTG CAC CGC ATC GAG GGG CCG AAC GCT         846
Pro Pro Glu Ala Ser Val Gln Val His Arg Ile Glu Gly Pro Asn Ala
215                 220                 225                 230

GAA GGC CCA GCC TCT TCC CAG CAC TTG CTG CCG CAT CCC AAG CCC CCG         894
Glu Gly Pro Ala Ser Ser Gln His Leu Leu Pro His Pro Lys Pro Pro
                235                 240                 245

CAC CCG AGG CCA CCC ACT CAA AAG CCA CTG GGC CGC TGC TTC CAG GAC         942
His Pro Arg Pro Pro Thr Gln Lys Pro Leu Gly Arg Cys Phe Gln Asp
        250                 255                 260

ACA TTG CCC AAG CAG CCT TGT GGC AGC AAC CCT TTG CCT GGC CTT ACC         990
Thr Leu Pro Lys Gln Pro Cys Gly Ser Asn Pro Leu Pro Gly Leu Thr
        265                 270                 275

AAG CAG GAA GAT TGC TGC GGT AGC ATC GGT ACT GCC TGG GGA CAA AGC        1038
Lys Gln Glu Asp Cys Cys Gly Ser Ile Gly Thr Ala Trp Gly Gln Ser
280                 285                 290

AAG TGT CAC AAG TGC CCA CAG CTT CAG TAT ACA GGG GTG CAG AAG CCT        1086
Lys Cys His Lys Cys Pro Gln Leu Gln Tyr Thr Gly Val Gln Lys Pro
295                 300                 305                 310

GTA CCT GTA CGT GGG GAG GTG GGT GCT GAC TGC CCC CAG GGC TAC AAG        1134
Val Pro Val Arg Gly Glu Val Gly Ala Asp Cys Pro Gln Gly Tyr Lys
                315                 320                 325

AGG CTC AAC AGC ACC CAC TGC CAG GAT ATC AAC GAA TGT GCG ATG CCC        1182
Arg Leu Asn Ser Thr His Cys Gln Asp Ile Asn Glu Cys Ala Met Pro
                330                 335                 340

GGG AAT GTG TGC CAT GGT GAC TGC CTC AAC AAC CCT GGC TCT TAT CGC        1230
Gly Asn Val Cys His Gly Asp Cys Leu Asn Asn Pro Gly Ser Tyr Arg
        345                 350                 355

TGT GTC TGC CCG CCC GGT CAT AGC TTG GGT CCC CTC GCA GCA CAG TGC        1278
Cys Val Cys Pro Pro Gly His Ser Leu Gly Pro Leu Ala Ala Gln Cys
        360                 365                 370

ATT GCC GAC AAA CCA GAG GAG AAG AGC CTG TGT TTC CGC CTT GTG AGC        1326
Ile Ala Asp Lys Pro Glu Glu Lys Ser Leu Cys Phe Arg Leu Val Ser
375                 380                 385                 390

ACC GAA CAC CAG TGC CAG CAC CCT CTG ACC ACA CGC CTA ACC CGC CAG        1374
Thr Glu His Gln Cys Gln His Pro Leu Thr Thr Arg Leu Thr Arg Gln
                395                 400                 405

CTC TGC TGC TGT AGT GTG GGT AAA GCC TGG GGT GCC CGG TGC CAG CGC        1422
Leu Cys Cys Cys Ser Val Gly Lys Ala Trp Gly Ala Arg Cys Gln Arg
        410                 415                 420

TGC CCG GCA GAT GGT ACA GCA GCC TTC AAG GAG ATC TGC CCC GGC TGG        1470
Cys Pro Ala Asp Gly Thr Ala Ala Phe Lys Glu Ile Cys Pro Gly Trp
        425                 430                 435

GAA AGG GTA CCA TAT CCT CAC CTC CCA CCA GAC GCT CAC CAT CCA GGG        1518
Glu Arg Val Pro Tyr Pro His Leu Pro Pro Asp Ala His His Pro Gly
        440                 445                 450

GGA AAG CGA CTT CTC CCT CTT CCT GCA CCC GAC GGG CCA CCC AAA CCC        1566
Gly Lys Arg Leu Leu Pro Leu Pro Ala Pro Asp Gly Pro Pro Lys Pro
455                 460                 465                 470

CAG CAG CTT CCT GAA AGC CCC AGC CGA GCA CCA CCC CTC GAG GAC ACA        1614
Gln Gln Leu Pro Glu Ser Pro Ser Arg Ala Pro Pro Leu Glu Asp Thr
                475                 480                 485

GAG GAA GAG AGA GGA GTG ACC ATG GAT CCA CCA GTG AGT GAG GAG CGA        1662
Glu Glu Glu Arg Gly Val Thr Met Asp Pro Pro Val Ser Glu Glu Arg
                490                 495                 500
```

-continued

| | |
|---|---|
| TCG GTG CAG CAG AGC CAC CCC ACT ACC ACC ACC TCA CCC CCC CGG CCT<br>Ser Val Gln Gln Ser His Pro Thr Thr Thr Thr Ser Pro Pro Arg Pro<br>     505                    510                    515 | 1710 |
| TAC CCA GAG CTC ATC TCT CGC CCC TCC CCA CCT ACC TTC CAC CGG TTC<br>Tyr Pro Glu Leu Ile Ser Arg Pro Ser Pro Pro Thr Phe His Arg Phe<br>520                    525                    530 | 1758 |
| CTG CCA GAC TTG CCC CCA TCC CGA AGT GCA GTG GAG ATC GCC CCC ACT<br>Leu Pro Asp Leu Pro Pro Ser Arg Ser Ala Val Glu Ile Ala Pro Thr<br>535                    540                    545                    550 | 1806 |
| CAG GTC ACA GAG ACC GAT GAG TGC CGA TTG AAC CAG AAT ATC TGT GGC<br>Gln Val Thr Glu Thr Asp Glu Cys Arg Leu Asn Gln Asn Ile Cys Gly<br>                    555                    560                    565 | 1854 |
| CAT GGA CAG TGT GTG CCT GGC CCC TCG GAT TAC TCC TGC CAC TGC AAC<br>His Gly Gln Cys Val Pro Gly Pro Ser Asp Tyr Ser Cys His Cys Asn<br>     570                    575                    580 | 1902 |
| GCT GGC TAC CGG TCA CAC CCG CAG CAC CGC TAC TGT GTT GAT GTG AAC<br>Ala Gly Tyr Arg Ser His Pro Gln His Arg Tyr Cys Val Asp Val Asn<br>585                    590                    595 | 1950 |
| GAG TGC GAG GCA GAG CCC TGC GGC CCC GGG AAA GGC ATC TGT ATG AAC<br>Glu Cys Glu Ala Glu Pro Cys Gly Pro Gly Lys Gly Ile Cys Met Asn<br>600                    605                    610 | 1998 |
| ACT GGT GGC TCC TAC AAT TGT CAC TGC AAC CGA GGC TAC CGC CTC CAC<br>Thr Gly Gly Ser Tyr Asn Cys His Cys Asn Arg Gly Tyr Arg Leu His<br>615                    620                    625                    630 | 2046 |
| GTG GGT GCA GGG GGC CGC TCG TGC GTG GAC CTG AAC GAG TGC GCC AAG<br>Val Gly Ala Gly Gly Arg Ser Cys Val Asp Leu Asn Glu Cys Ala Lys<br>                    635                    640                    645 | 2094 |
| CCT CAC CTG TGT GGG GAC GGT GGC TTC TGC ATC AAC TTC CCT GGT CAC<br>Pro His Leu Cys Gly Asp Gly Gly Phe Cys Ile Asn Phe Pro Gly His<br>     650                    655                    660 | 2142 |
| TAC AAA TGC AAC TGC TAT CCT GGC TAC CGG CTC AAG GCC TCC CGA CCG<br>Tyr Lys Cys Asn Cys Tyr Pro Gly Tyr Arg Leu Lys Ala Ser Arg Pro<br>665                    670                    675 | 2190 |
| CCC ATT TGC GAA GAC ATC GAC GAG TGT CGC GAC CCT AGC ACC TGC CCT<br>Pro Ile Cys Glu Asp Ile Asp Glu Cys Arg Asp Pro Ser Thr Cys Pro<br>                    680                    685                    690 | 2238 |
| GAT GGC AAA TGT GAA AAC AAA CCT GGC AGC TTC AAG TGC ATC GCC TGC<br>Asp Gly Lys Cys Glu Asn Lys Pro Gly Ser Phe Lys Cys Ile Ala Cys<br>695                    700                    705                    710 | 2286 |
| CAG CCT GGC TAC CGT AGC CAG GGG GGC GGG GCC TGT CGT GAT GTC AAC<br>Gln Pro Gly Tyr Arg Ser Gln Gly Gly Gly Ala Cys Arg Asp Val Asn<br>                    715                    720                    725 | 2334 |
| GAA TGC TCC GAA GGT ACC CCC TGC TCT CCT GGA TGG TGT GAG AAA CTT<br>Glu Cys Ser Glu Gly Thr Pro Cys Ser Pro Gly Trp Cys Glu Lys Leu<br>                    730                    735                    740 | 2382 |
| CCG GGT TCT TAC CGT TGC ACG TGT GCC CAG GGG ATA CGA ACC CGC ACA<br>Pro Gly Ser Tyr Arg Cys Thr Cys Ala Gln Gly Ile Arg Thr Arg Thr<br>745                    750                    755 | 2430 |
| GGA CGC CTC AGT TGC ATA GAC GTG GAT GAC TGT GAG GCT GGG AAA GTG<br>Gly Arg Leu Ser Cys Ile Asp Val Asp Asp Cys Glu Ala Gly Lys Val<br>                    760                    765                    770 | 2478 |
| TGC CAA GAT GGC ATC TGC ACG AAC ACA CCA GGC TCT TTC CAG TGT CAG<br>Cys Gln Asp Gly Ile Cys Thr Asn Thr Pro Gly Ser Phe Gln Cys Gln<br>775                    780                    785                    790 | 2526 |
| TGC CTC TCC GGC TAT CAT CTG TCA AGG GAT CGG AGC CGC TGT GAG GAC<br>Cys Leu Ser Gly Tyr His Leu Ser Arg Asp Arg Ser Arg Cys Glu Asp<br>                    795                    800                    805 | 2574 |
| ATT GAT GAA TGT GAC TTC CCT GCG GCC TGC ATC GGG GGT GAC TGC ATC<br>Ile Asp Glu Cys Asp Phe Pro Ala Ala Cys Ile Gly Gly Asp Cys Ile<br>                    810                    815                    820 | 2622 |

-continued

| | |
|---|---|
| AAT ACC AAT GGT TCC TAC AGA TGT CTC TGT CCC CTG GGT CAT CGG TTG<br>Asn Thr Asn Gly Ser Tyr Arg Cys Leu Cys Pro Leu Gly His Arg Leu<br>          825                830                835 | 2670 |
| GTG GGC GGC AGG AAG TGC AAG AAA GAT ATA GAT GAG TGC AGC CAG GAC<br>Val Gly Gly Arg Lys Cys Lys Lys Asp Ile Asp Glu Cys Ser Gln Asp<br>840                      845                      850 | 2718 |
| CCA GGC CTG TGC CTG CCC CAT GCC TGC GAG AAC CTC CAG GGC TCC TAT<br>Pro Gly Leu Cys Leu Pro His Ala Cys Glu Asn Leu Gln Gly Ser Tyr<br>855                      860                      865                870 | 2766 |
| GTC TGT GTC TGT GAT GAG GGT TTC ACA CTC ACC CAG GAC CAG CAT GGG<br>Val Cys Val Cys Asp Glu Gly Phe Thr Leu Thr Gln Asp Gln His Gly<br>                  875                      880                      885 | 2814 |
| TGT GAG GAG GTG GAG CAG CCC CAC CAC AAG AAG GAG TGC TAC CTT AAC<br>Cys Glu Glu Val Glu Gln Pro His His Lys Lys Glu Cys Tyr Leu Asn<br>                890                      895                      900 | 2862 |
| TTC GAT GAC ACA GTG TTC TGT GAC AGC GTA TTG GCT ACC AAT GTC ACT<br>Phe Asp Asp Thr Val Phe Cys Asp Ser Val Leu Ala Thr Asn Val Thr<br>905                      910                      915 | 2910 |
| CAG CAG GAA TGC TGT TGC TCT CTG GGA GCT GGC TGG GGA GAC CAC TGC<br>Gln Gln Glu Cys Cys Cys Ser Leu Gly Ala Gly Trp Gly Asp His Cys<br>            920                      925                      930 | 2958 |
| GAA ATC TAT CCC TGT CCA GTC TAC AGC TCA GCC GAA TTT CAC AGC CTG<br>Glu Ile Tyr Pro Cys Pro Val Tyr Ser Ser Ala Glu Phe His Ser Leu<br>935                      940                      945                950 | 3006 |
| GTG CCT GAT GGG AAA AGG CTA CAC TCA GGA CAA CAA CAT TGT GAA CTA<br>Val Pro Asp Gly Lys Arg Leu His Ser Gly Gln Gln His Cys Glu Leu<br>                  955                      960                      965 | 3054 |
| TGC ATT CCT GCC CAC CGT GAC ATC GAC GAA TGC ATA TTG TTT GGG GCA<br>Cys Ile Pro Ala His Arg Asp Ile Asp Glu Cys Ile Leu Phe Gly Ala<br>                  970                      975                      980 | 3102 |
| GAG ATC TGC AAG GAG GGC AAG TGT GTG AAC TCG CAG CCC GGC TAC GAG<br>Glu Ile Cys Lys Glu Gly Lys Cys Val Asn Ser Gln Pro Gly Tyr Glu<br>985                      990                      995 | 3150 |
| TGC TAC TGC AAG CAG GGC TTC TAC TAC GAT GGC AAC CTG CTG GAG TGC<br>Cys Tyr Cys Lys Gln Gly Phe Tyr Tyr Asp Gly Asn Leu Leu Glu Cys<br>1000                      1005                      1010 | 3198 |
| GTG GAC GTG GAC GAG TGC TTG GAT GAG TCT AAC TGC AGG AAC GGA GTG<br>Val Asp Val Asp Glu Cys Leu Asp Glu Ser Asn Cys Arg Asn Gly Val<br>1015                      1020                      1025                      1030 | 3246 |
| TGT GAG AAC ACG TGG CGG CTA CCG TGT GCC TGC ACT CCG CCG GCA GAG<br>Cys Glu Asn Thr Trp Arg Leu Pro Cys Ala Cys Thr Pro Pro Ala Glu<br>                1035                      1040                      1045 | 3294 |
| TAC AGT CCC GCA CAG GCC CAG TGT CTG ATC CCG GAG AGA TGG AGC ACG<br>Tyr Ser Pro Ala Gln Ala Gln Cys Leu Ile Pro Glu Arg Trp Ser Thr<br>                1050                      1055                      1060 | 3342 |
| CCC CAG AGA GAC GTG AAG TGT GCT GGG GCC AGC GAG GAG AGG ACG GCA<br>Pro Gln Arg Asp Val Lys Cys Ala Gly Ala Ser Glu Glu Arg Thr Ala<br>                1065                      1070                      1075 | 3390 |
| TGT GTA TGG GGC CCC TGG GCG GGA CCT GCC CTC ACT TTT GAT GAC TGC<br>Cys Val Trp Gly Pro Trp Ala Gly Pro Ala Leu Thr Phe Asp Asp Cys<br>1080                      1085                      1090 | 3438 |
| TGC TGC CGC CAG CCG CGG CTG GGT ACC CAG TGC AGA CCG TGC CCG CCA<br>Cys Cys Arg Gln Pro Arg Leu Gly Thr Gln Cys Arg Pro Cys Pro Pro<br>1095                      1100                      1105                      1110 | 3486 |
| CGT GGC ACC GGG TCC CAG TGC CCG ACT TCA CAG AGT GAG AGC AAT TCT<br>Arg Gly Thr Gly Ser Gln Cys Pro Thr Ser Gln Ser Glu Ser Asn Ser<br>                1115                      1120                      1125 | 3534 |
| TTC TGG GAC ACA AGC CCC CTG CTA CTG GGG AAG TCT CCG CGA GAC GAA<br>Phe Trp Asp Thr Ser Pro Leu Leu Leu Gly Lys Ser Pro Arg Asp Glu<br>                1130                      1135                      1140 | 3582 |

```
GAC AGC TCA GAG GAG GAT TCA GAT GAG TGC CGT TGT GTG AGC GGA CCG      3630
Asp Ser Ser Glu Glu Asp Ser Asp Glu Cys Arg Cys Val Ser Gly Pro
            1145                1150                1155

TGT GTG CCA CGG CCA GGC GGG GCG GTA TGC GAG TGT CCT GGA GGC TTT      3678
Cys Val Pro Arg Pro Gly Gly Ala Val Cys Glu Cys Pro Gly Gly Phe
    1160                1165                1170

CAG CTG GAC GCC TCC CGT GCC CGC TGC GTG GAC ATT GAT GAG TGC CGA      3726
Gln Leu Asp Ala Ser Arg Ala Arg Cys Val Asp Ile Asp Glu Cys Arg
1175                1180                1185                1190

GAA CTG AAC CAG CGG GGA CTG CTG TGT AAG AGC GAG CGG TGC GTG AAC      3774
Glu Leu Asn Gln Arg Gly Leu Leu Cys Lys Ser Glu Arg Cys Val Asn
                1195                1200                1205

ACC AGT GGA TCC TTC CGC TGT GTC TGC AAA GCT GGC TTC ACG CGC AGC      3822
Thr Ser Gly Ser Phe Arg Cys Val Cys Lys Ala Gly Phe Thr Arg Ser
            1210                1215                1220

CGC CCT CAC GGG CCT GCG TGC CTC AGC GCC GCC GCT GAT GAT GCA GCC      3870
Arg Pro His Gly Pro Ala Cys Leu Ser Ala Ala Ala Asp Asp Ala Ala
        1225                1230                1235

ATA GCC CAC ACC TCA GTG ATC GAT CAT CGA GGG TAT TTT CAC              3912
Ile Ala His Thr Ser Val Ile Asp His Arg Gly Tyr Phe His
1240                1245                1250

TGAAAGTGGA GACAGACAAG TACATCCTTT GCTCCTGACC AAACGAGAGC ATGGACCCAA    3972

GGATCCTTCA GGGCCCACAA ATCTCCTTCC CACACCCCAA ACCCAAGGTG CTCCTGTCTG    4032

CAGAGTGCTG TCTGCTTTCT CCCAAGGGTG ATTCCTAGAA ACTTCGACAT CAGATCTGCC    4092

CCTTTAATTT ACTCTTGGCT TTCAAGGCAA ATTGATATTC ACATCCAAAG CGGGCAGCAT    4152

CAACTGCTTG GCGGGTTGGA CTGAGCTGGG ACCCAGGATG TGAAATAGAA TTTATTGTGG    4212

CTCTGATTAT GTACACTAGA TGTGCCTGAC CTGCTGACCA GGCTCACATG GTTTGTACAA    4272

TAAATACATC CGCCGGGAAA AAAAAAAAA AAAAAAAAA AA                        4314

(2) INFORMATION FOR SEQ ID NO:3:

(i) SEQUENCE CHARACTERISTICS:
        (A) LENGTH: 1252 amino acids
        (B) TYPE: amino acid
        (D) TOPOLOGY: linear (ii) MOLECULE TYPE: protein (xi) SEQUENCE DESCRIPTION: SEQ ID NO:3:

Met Arg Gln Ala Gly Gly Leu Gly Leu Leu Ala Leu Leu Leu Ala
1               5                   10                  15

Leu Leu Gly Pro Gly Gly Arg Gly Val Gly Arg Pro Gly Ser Gly Ala
                20                  25                  30

Gln Ala Gly Ala Gly Arg Trp Ala Gln Arg Phe Lys Val Val Phe Ala
            35                  40                  45

Pro Val Ile Cys Lys Arg Thr Cys Leu Lys Gly Gln Cys Arg Asp Ser
        50                  55                  60

Cys Gln Gln Gly Ser Asn Met Thr Leu Ile Gly Glu Asn Gly His Ser
65                  70                  75                  80

Thr Asp Thr Leu Thr Gly Ser Ala Phe Arg Val Val Cys Pro Leu
                85                  90                  95

Pro Cys Met Asn Gly Gly Gln Cys Ser Ser Arg Asn Gln Cys Leu Cys
                100                 105                 110

Pro Pro Asp Phe Thr Gly Arg Phe Cys Gln Val Pro Ala Ala Gly Thr
            115                 120                 125

Gly Ala Gly Thr Gly Ser Ser Gly Pro Gly Trp Pro Asp Arg Ala Met
        130                 135                 140
```

```
Ser Thr Gly Pro Leu Pro Pro Leu Ala Pro Glu Gly Ser Val Ala
145                 150                 155                 160

Ser Lys His Ala Ile Tyr Ala Val Gln Val Ile Ala Asp Pro Pro Gly
                165                 170                 175

Pro Gly Glu Gly Pro Pro Ala Gln His Ala Ala Phe Leu Val Pro Leu
            180                 185                 190

Gly Pro Gly Gln Ile Ser Ala Glu Val Gln Ala Pro Pro Val Val
        195                 200                 205

Asn Val Arg Val His His Pro Pro Glu Ala Ser Val Gln Val His Arg
    210                 215                 220

Ile Glu Gly Pro Asn Ala Glu Gly Pro Ala Ser Ser Gln His Leu Leu
225                 230                 235                 240

Pro His Pro Lys Pro Pro His Pro Arg Pro Thr Gln Lys Pro Leu
                245                 250                 255

Gly Arg Cys Phe Gln Asp Thr Leu Pro Lys Gln Pro Cys Gly Ser Asn
            260                 265                 270

Pro Leu Pro Gly Leu Thr Lys Gln Glu Asp Cys Cys Gly Ser Ile Gly
            275                 280                 285

Thr Ala Trp Gly Gln Ser Lys Cys His Lys Cys Pro Gln Leu Gln Tyr
        290                 295                 300

Thr Gly Val Gln Lys Pro Val Pro Val Arg Gly Glu Val Gly Ala Asp
305                 310                 315                 320

Cys Pro Gln Gly Tyr Lys Arg Leu Asn Ser Thr His Cys Gln Asp Ile
                325                 330                 335

Asn Glu Cys Ala Met Pro Gly Asn Val Cys His Gly Asp Cys Leu Asn
            340                 345                 350

Asn Pro Gly Ser Tyr Arg Cys Val Cys Pro Pro Gly His Ser Leu Gly
            355                 360                 365

Pro Leu Ala Ala Gln Cys Ile Ala Asp Lys Pro Glu Glu Lys Ser Leu
            370                 375                 380

Cys Phe Arg Leu Val Ser Thr Glu His Gln Cys Gln His Pro Leu Thr
385                 390                 395                 400

Thr Arg Leu Thr Arg Gln Leu Cys Cys Cys Ser Val Gly Lys Ala Trp
                405                 410                 415

Gly Ala Arg Cys Gln Arg Cys Pro Ala Asp Gly Thr Ala Ala Phe Lys
            420                 425                 430

Glu Ile Cys Pro Gly Trp Glu Arg Val Pro Tyr Pro His Leu Pro Pro
            435                 440                 445

Asp Ala His His Pro Gly Gly Lys Arg Leu Leu Pro Leu Pro Ala Pro
    450                 455                 460

Asp Gly Pro Pro Lys Pro Gln Gln Leu Pro Glu Ser Pro Ser Arg Ala
465                 470                 475                 480

Pro Pro Leu Glu Asp Thr Glu Glu Glu Arg Gly Val Thr Met Asp Pro
            485                 490                 495

Pro Val Ser Glu Glu Arg Ser Val Gln Gln Ser His Pro Thr Thr Thr
            500                 505                 510

Thr Ser Pro Pro Arg Pro Tyr Pro Glu Leu Ile Ser Arg Pro Ser Pro
        515                 520                 525

Pro Thr Phe His Arg Phe Leu Pro Asp Leu Pro Pro Ser Arg Ser Ala
        530                 535                 540

Val Glu Ile Ala Pro Thr Gln Val Thr Glu Thr Asp Glu Cys Arg Leu
545                 550                 555                 560

Asn Gln Asn Ile Cys Gly His Gly Gln Cys Val Pro Gly Pro Ser Asp
```

-continued

```
                565                 570                 575
Tyr Ser Cys His Cys Asn Ala Gly Tyr Arg Ser His Pro Gln His Arg
                580                 585                 590
Tyr Cys Val Asp Val Asn Glu Cys Glu Ala Glu Pro Cys Gly Pro Gly
                595                 600                 605
Lys Gly Ile Cys Met Asn Thr Gly Gly Ser Tyr Asn Cys His Cys Asn
                610                 615                 620
Arg Gly Tyr Arg Leu His Val Gly Ala Gly Gly Arg Ser Cys Val Asp
625                 630                 635                 640
Leu Asn Glu Cys Ala Lys Pro His Leu Cys Gly Asp Gly Gly Phe Cys
                645                 650                 655
Ile Asn Phe Pro Gly His Tyr Lys Cys Asn Cys Tyr Pro Gly Tyr Arg
                660                 665                 670
Leu Lys Ala Ser Arg Pro Pro Ile Cys Glu Asp Ile Asp Glu Cys Arg
                675                 680                 685
Asp Pro Ser Thr Cys Pro Asp Gly Lys Cys Glu Asn Lys Pro Gly Ser
                690                 695                 700
Phe Lys Cys Ile Ala Cys Gln Pro Gly Tyr Arg Ser Gln Gly Gly Gly
705                 710                 715                 720
Ala Cys Arg Asp Val Asn Glu Cys Ser Glu Gly Thr Pro Cys Ser Pro
                725                 730                 735
Gly Trp Cys Glu Lys Leu Pro Gly Ser Tyr Arg Cys Thr Cys Ala Gln
                740                 745                 750
Gly Ile Arg Thr Arg Thr Gly Arg Leu Ser Cys Ile Asp Val Asp Asp
                755                 760                 765
Cys Glu Ala Gly Lys Val Cys Gln Asp Gly Ile Cys Thr Asn Thr Pro
770                 775                 780
Gly Ser Phe Gln Cys Gln Cys Leu Ser Gly Tyr His Leu Ser Arg Asp
785                 790                 795                 800
Arg Ser Arg Cys Glu Asp Ile Asp Glu Cys Asp Phe Pro Ala Ala Cys
                805                 810                 815
Ile Gly Gly Asp Cys Ile Asn Thr Asn Gly Ser Tyr Arg Cys Leu Cys
                820                 825                 830
Pro Leu Gly His Arg Leu Val Gly Gly Arg Lys Cys Lys Lys Asp Ile
                835                 840                 845
Asp Glu Cys Ser Gln Asp Pro Gly Leu Cys Leu Pro His Ala Cys Glu
850                 855                 860
Asn Leu Gln Gly Ser Tyr Val Cys Val Cys Asp Glu Gly Phe Thr Leu
865                 870                 875                 880
Thr Gln Asp Gln His Gly Cys Glu Glu Val Glu Gln Pro His His Lys
                885                 890                 895
Lys Glu Cys Tyr Leu Asn Phe Asp Asp Thr Val Phe Cys Asp Ser Val
                900                 905                 910
Leu Ala Thr Asn Val Thr Gln Gln Glu Cys Cys Cys Ser Leu Gly Ala
                915                 920                 925
Gly Trp Gly Asp His Cys Glu Ile Tyr Pro Cys Pro Val Tyr Ser Ser
                930                 935                 940
Ala Glu Phe His Ser Leu Val Pro Asp Gly Lys Arg Leu His Ser Gly
945                 950                 955                 960
Gln Gln His Cys Glu Leu Cys Ile Pro Ala His Arg Asp Ile Asp Glu
                965                 970                 975
Cys Ile Leu Phe Gly Ala Glu Ile Cys Lys Glu Gly Lys Cys Val Asn
                980                 985                 990
```

```
Ser Gln Pro Gly Tyr Glu Cys Tyr Cys Lys Gln Gly Phe Tyr Tyr Asp
    995                 1000                1005

Gly Asn Leu Leu Glu Cys Val Asp Val Asp Glu Cys Leu Asp Glu Ser
    1010                1015                1020

Asn Cys Arg Asn Gly Val Cys Glu Asn Thr Trp Arg Leu Pro Cys Ala
1025                1030                1035                1040

Cys Thr Pro Pro Ala Glu Tyr Ser Pro Ala Gln Ala Gln Cys Leu Ile
                1045                1050                1055

Pro Glu Arg Trp Ser Thr Pro Gln Arg Asp Val Lys Cys Ala Gly Ala
                1060                1065                1070

Ser Glu Glu Arg Thr Ala Cys Val Trp Gly Pro Trp Ala Gly Pro Ala
                1075                1080                1085

Leu Thr Phe Asp Asp Cys Cys Cys Arg Gln Pro Arg Leu Gly Thr Gln
    1090                1095                1100

Cys Arg Pro Cys Pro Pro Arg Gly Thr Gly Ser Gln Cys Pro Thr Ser
1105                1110                1115                1120

Gln Ser Glu Ser Asn Ser Phe Trp Asp Thr Ser Pro Leu Leu Leu Gly
                1125                1130                1135

Lys Ser Pro Arg Asp Glu Asp Ser Ser Glu Glu Asp Ser Asp Glu Cys
                1140                1145                1150

Arg Cys Val Ser Gly Pro Cys Val Pro Arg Pro Gly Gly Ala Val Cys
                1155                1160                1165

Glu Cys Pro Gly Gly Phe Gln Leu Asp Ala Ser Arg Ala Arg Cys Val
    1170                1175                1180

Asp Ile Asp Glu Cys Arg Glu Leu Asn Gln Arg Gly Leu Leu Cys Lys
1185                1190                1195                1200

Ser Glu Arg Cys Val Asn Thr Ser Gly Ser Phe Arg Cys Val Cys Lys
                1205                1210                1215

Ala Gly Phe Thr Arg Ser Arg Pro His Gly Pro Ala Cys Leu Ser Ala
    1220                1225                1230

Ala Ala Asp Asp Ala Ala Ile Ala His Thr Ser Val Ile Asp His Arg
    1235                1240                1245

Gly Tyr Phe His
    1250

(2) INFORMATION FOR SEQ ID NO:4:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:4:

AACATGACGC TCATCGGAGA GAAC                                          24

(2) INFORMATION FOR SEQ ID NO:5:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:5:

AGGTGATCGC AGATCCTC                                                 18
```

(2) INFORMATION FOR SEQ ID NO:6:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:6:

TACCGATGCT ACCGCAGCAA TCTT        24

(2) INFORMATION FOR SEQ ID NO:7:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:7:

ATGCCTAAAC TCTACCAGCA CG        22

(2) INFORMATION FOR SEQ ID NO:8:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:8:

GAGTCACGTC ATCCATTCCA CA        22

(2) INFORMATION FOR SEQ ID NO:9:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:9:

CGTCCAAGTT GTGTCTTAGC AG        22

(2) INFORMATION FOR SEQ ID NO:10:

(i) SEQUENCE CHARACTERISTICS:
        (A) LENGTH: 53 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:10:

Gly Pro Pro Gly Pro Gln Gly Ala Thr Gly Pro Leu Gly Pro Lys Gly
1               5                   10              15

Gln Thr Gly Glu Pro Gly Ile Ala Gly Phe Lys Gly Glu Gln Gly Pro
             20                 25              30

```
Lys Gly Glu Thr Gly Pro Ala Gly Pro Gln Gly Ala Pro Gly Pro Ala
        35                  40                  45

Gly Glu Glu Gly Lys
        50

(2) INFORMATION FOR SEQ ID NO:11:

(i) SEQUENCE CHARACTERISTICS:
        (A) LENGTH: 159 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:11:

GGCCCTCCCG GTCCTCAAGG TGCAACTGGT CCTCTGGGCC CCAAAGGTCA GACGGGTGAG        60

CCCGGCATCG CTGGCTTCAA AGGTGAACAA GGCCCCAAGG GAGAGACTGG ACCTGCTGGG       120

CCCCAGGGAG CCCCTGGCCC TGCTGGTGAA GAAGGAAAA                              159

(2) INFORMATION FOR SEQ ID NO:12:

(i) SEQUENCE CHARACTERISTICS:
        (A) LENGTH: 1442 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:12:

Met Ile Arg Leu Gly Ala Pro Gln Ser Leu Val Leu Leu Thr Leu Leu
1               5                   10                  15

Ile Ala Ala Val Leu Arg Cys Gln Gly Gln Asp Ala Gln Glu Ala Gly
            20                  25                  30

Ser Cys Leu Gln Asn Gly Gln Arg Tyr Lys Asp Lys Asp Val Trp Lys
        35                  40                  45

Pro Ser Ser Cys Arg Ile Cys Val Cys Asp Thr Gly Asn Val Leu Cys
    50                  55                  60

Asp Asp Ile Ile Cys Glu Asp Pro Asp Cys Leu Asn Pro Glu Ile Pro
65                  70                  75                  80

Phe Gly Glu Cys Cys Pro Ile Cys Pro Ala Asp Leu Ala Thr Ala Ser
                85                  90                  95

Gly Arg Lys Leu Gly Pro Lys Gly Gln Lys Gly Glu Pro Gly Asp Ile
            100                 105                 110

Arg Asp Gly Pro Ala Gly Glu Gln Gly Pro Arg Gly Asp Arg Gly Asp
        115                 120                 125

Lys Gly Glu Lys Asn Phe Ala Ala Gln Met Ala Gly Gly Tyr Asp Glu
    130                 135                 140

Lys Ala Gly Gly Ala Gln Met Gly Val Met Gln Gly Pro Met Gly Pro
145                 150                 155                 160

Met Gly Pro Arg Gly Pro Pro Gly Pro Ala Gly Ala Pro Gly Pro Gln
                165                 170                 175

Gly Phe Gln Gly Asn Pro Gly Glu Pro Gly Glu Pro Gly Val Ser Gly
            180                 185                 190

Pro Met Gly Pro Arg Gly Pro Pro Gly Pro Ala Gly Lys Pro Gly Asp
        195                 200                 205

Asp Gly Glu Ala Gly Lys Pro Gly Lys Ser Gly Glu Arg Gly Leu Pro
    210                 215                 220
```

-continued

Gly Pro Met Gly Ala Arg Gly Phe Pro Gly Thr Pro Gly Leu Pro Gly
225                 230                 235                 240

Val Lys Gly His Arg Gly Tyr Pro Gly Leu Asp Gly Ala Lys Gly Glu
            245                 250                 255

Ala Gly Ala Pro Gly Val Lys Gly Ser Gly Ser Pro Gly Glu Asn
        260                 265                 270

Gly Ser Pro Gly Pro Met Gly Pro Arg Gly Leu Pro Gly Glu Arg Gly
        275                 280                 285

Arg Thr Gly Pro Ala Gly Ala Gly Ala Arg Gly Asn Asp Gly Gln
    290                 295                 300

Pro Gly Pro Ala Gly Pro Gly Pro Val Gly Pro Ala Gly Gly Pro
305             310                 315                 320

Gly Phe Pro Gly Ala Pro Gly Ala Lys Gly Glu Ala Gly Pro Thr Gly
            325                 330                 335

Ala Arg Gly Pro Glu Gly Ala Gln Gly Ser Arg Gly Glu Pro Gly Asn
            340                 345                 350

Pro Gly Ser Pro Gly Pro Ala Gly Ala Ser Gly Asn Pro Gly Thr Asp
        355                 360                 365

Gly Ile Pro Gly Ala Lys Gly Ser Ala Gly Ala Pro Gly Ile Ala Gly
        370                 375                 380

Ala Pro Gly Phe Pro Gly Pro Arg Gly Pro Pro Gly Pro Gln Gly Ala
385                 390                 395                 400

Thr Gly Pro Leu Gly Pro Lys Gly Gln Ala Gly Glu Pro Gly Ile Ala
            405                 410                 415

Gly Phe Lys Gly Asp Gln Gly Pro Lys Gly Glu Thr Gly Pro Ala Gly
            420                 425                 430

Pro Gln Gly Ala Pro Gly Pro Ala Gly Glu Glu Gly Lys Arg Gly Ala
        435                 440                 445

Arg Gly Glu Pro Gly Gly Ala Gly Pro Ile Gly Pro Pro Gly Glu Arg
    450                 455                 460

Gly Ala Pro Gly Asn Arg Gly Phe Pro Gly Gln Asp Gly Leu Ala Gly
465                 470                 475                 480

Pro Lys Gly Ala Pro Gly Glu Arg Gly Pro Ser Gly Leu Ala Gly Pro
            485                 490                 495

Lys Gly Ala Asn Gly Asp Pro Gly Arg Pro Gly Glu Pro Gly Leu Pro
            500                 505                 510

Gly Ala Arg Gly Leu Thr Gly Arg Pro Gly Asp Ala Gly Pro Gln Gly
        515                 520                 525

Lys Val Gly Pro Ser Gly Ala Pro Gly Glu Asp Gly Arg Pro Gly Pro
    530                 535                 540

Pro Gly Pro Gln Gly Ala Arg Gly Gln Pro Gly Val Met Gly Phe Pro
545                 550                 555                 560

Gly Pro Lys Gly Ala Asn Gly Glu Pro Gly Lys Ala Gly Glu Lys Gly
            565                 570                 575

Leu Ala Gly Ala Pro Gly Leu Arg Gly Leu Pro Gly Lys Asp Gly Glu
            580                 585                 590

Thr Gly Ala Ala Gly Pro Pro Gly Pro Ser Gly Pro Ala Gly Glu Arg
        595                 600                 605

Gly Glu Gln Gly Ala Pro Gly Pro Ser Gly Phe Gln Gly Leu Pro Gly
    610                 615                 620

Pro Pro Gly Pro Pro Gly Glu Gly Gly Lys Gln Gly Asp Gln Gly Ile
625                 630                 635                 640

Pro Gly Glu Ala Gly Ala Pro Gly Leu Val Gly Pro Arg Gly Glu Arg
            645                 650                 655

-continued

```
Gly Phe Pro Gly Glu Arg Gly Ser Pro Gly Ala Gln Gly Leu Gln Gly
                660                 665                 670

Pro Arg Gly Leu Pro Gly Thr Pro Gly Thr Asp Gly Pro Lys Gly Ala
            675                 680                 685

Ala Gly Pro Asp Gly Pro Pro Gly Ala Gln Gly Pro Pro Gly Leu Gln
        690                 695                 700

Gly Met Pro Gly Glu Arg Gly Ala Ala Gly Ile Ala Gly Pro Lys Gly
705                 710                 715                 720

Asp Arg Gly Asp Val Gly Glu Lys Gly Pro Glu Gly Ala Pro Gly Lys
                725                 730                 735

Asp Gly Gly Arg Gly Leu Thr Gly Pro Ile Gly Pro Pro Gly Pro Ala
            740                 745                 750

Gly Ala Asn Gly Glu Lys Gly Glu Ala Gly Pro Pro Gly Pro Ser Gly
        755                 760                 765

Ser Thr Gly Ala Arg Gly Ala Pro Gly Glu Pro Gly Glu Thr Gly Pro
    770                 775                 780

Pro Gly Pro Ala Gly Phe Ala Gly Pro Pro Gly Ala Asp Gly Gln Pro
785                 790                 795                 800

Gly Ala Lys Gly Asp Gln Gly Glu Ala Gly Gln Lys Gly Asp Ala Gly
                805                 810                 815

Ala Pro Gly Pro Gln Gly Pro Ser Gly Ala Pro Gly Pro Gln Gly Pro
            820                 825                 830

Thr Gly Val Thr Gly Pro Lys Gly Ala Arg Gly Ala Gln Gly Pro Pro
        835                 840                 845

Gly Ala Thr Gly Phe Pro Gly Ala Ala Gly Arg Val Gly Pro Pro Gly
    850                 855                 860

Ala Asn Gly Asn Pro Gly Pro Ala Gly Pro Pro Gly Pro Ala Gly Lys
865                 870                 875                 880

Asp Gly Pro Lys Gly Val Arg Gly Asp Ser Gly Pro Pro Gly Arg Ala
                885                 890                 895

Gly Asp Pro Gly Leu Glu Gly Pro Ala Gly Ala Pro Gly Glu Lys Gly
            900                 905                 910

Glu Pro Gly Asp Asp Gly Pro Ser Gly Leu Asp Gly Pro Pro Gly Pro
        915                 920                 925

Gln Gly Leu Ala Gly Gln Arg Gly Ile Val Gly Leu Pro Gly Gln Arg
    930                 935                 940

Gly Glu Arg Gly Phe Pro Gly Leu Pro Gly Pro Ser Gly Glu Pro Gly
945                 950                 955                 960

Lys Gln Gly Ala Pro Gly Ala Ser Gly Asp Arg Gly Pro Pro Gly Pro
                965                 970                 975

Val Gly Pro Pro Gly Leu Thr Gly Pro Ala Gly Glu Pro Gly Arg Glu
            980                 985                 990

Gly Ser Pro Gly Ala Asp Gly Pro Pro Gly Arg Asp Gly Ala Ala Gly
        995                 1000                1005

Val Lys Gly Asp Arg Gly Glu Thr Gly Ala Leu Gly Ala Pro Gly Ala
    1010                1015                1020

Pro Gly Pro Pro Gly Ser Pro Gly Pro Ala Gly Pro Thr Gly Lys Gln
1025                1030                1035                1040

Gly Asp Arg Gly Glu Ala Gly Ala Gln Gly Pro Met Gly Pro Ser Gly
                1045                1050                1055

Pro Ala Gly Ala Arg Gly Ile Ala Gly Pro Gln Gly Pro Arg Gly Asp
            1060                1065                1070

Lys Gly Glu Ser Gly Glu Gln Gly Glu Arg Gly Leu Lys Gly His Arg
```

```
                    1075                1080                1085
Gly Phe Thr Gly Leu Gln Gly Leu Pro Gly Pro Gly Pro Ser Gly
    1090                1095                1100

Asp Gln Gly Ala Ser Gly Pro Ala Gly Pro Ser Gly Pro Arg Gly Pro
1105                1110                1115                1120

Pro Gly Pro Val Gly Pro Ser Gly Lys Asp Gly Ser Asn Gly Ile Pro
                1125                1130                1135

Gly Pro Ile Gly Pro Pro Gly Pro Arg Gly Arg Ser Gly Glu Thr Gly
                1140                1145                1150

Pro Val Gly Pro Pro Gly Ser Pro Gly Pro Pro Gly Pro Pro Gly Pro
            1155                1160                1165

Pro Gly Pro Gly Ile Asp Met Ser Ala Phe Ala Gly Leu Gly Gln Arg
    1170                1175                1180

Glu Lys Gly Pro Asp Pro Met Gln Tyr Met Arg Ala Asp Glu Ala Asp
1185                1190                1195                1200

Ser Thr Leu Arg Gln His Asp Val Glu Val Asp Ala Thr Leu Lys Ser
                1205                1210                1215

Leu Asn Asn Gln Ile Glu Ser Ile Arg Ser Pro Asp Gly Ser Arg Lys
            1220                1225                1230

Asn Pro Ala Arg Thr Cys Gln Asp Leu Lys Leu Cys His Pro Glu Trp
            1235                1240                1245

Lys Ser Gly Asp Tyr Trp Ile Asp Pro Asn Gln Gly Cys Thr Leu Asp
            1250                1255                1260

Ala Met Lys Val Phe Cys Asn Met Glu Thr Gly Glu Thr Cys Val Tyr
1265                1270                1275                1280

Pro Asn Pro Ala Thr Val Pro Arg Lys Asn Trp Trp Ser Ser Lys Ser
                1285                1290                1295

Lys Glu Lys Lys His Ile Trp Phe Gly Glu Thr Met Asn Gly Gly Phe
            1300                1305                1310

His Phe Ser Tyr Gly Asp Gly Asn Leu Ala Pro Asn Thr Ala Asn Val
            1315                1320                1325

Gln Met Thr Phe Leu Arg Leu Leu Ser Thr Glu Gly Ser Gln Asn Ile
            1330                1335                1340

Thr Tyr His Cys Lys Asn Ser Ile Ala Tyr Leu Asp Glu Ala Ala Gly
1345                1350                1355                1360

Asn Leu Lys Lys Ala Leu Leu Ile Gln Gly Ser Asn Asp Val Glu Met
                1365                1370                1375

Arg Ala Glu Gly Asn Ser Arg Phe Thr Tyr Thr Ala Leu Lys Asp Gly
            1380                1385                1390

Cys Thr Lys His Thr Gly Lys Trp Gly Lys Thr Val Ile Glu Tyr Arg
            1395                1400                1405

Ser Gln Lys Thr Ser Arg Leu Pro Ile Ile Asp Ile Ala Pro Met Asp
            1410                1415                1420

Ile Gly Gly Ala Glu Gln Glu Phe Gly Val Asp Ile Gly Pro Val Cys
1425                1430                1435                1440

Phe Leu (2) INFORMATION FOR SEQ ID NO:13:

(i) SEQUENCE CHARACTERISTICS:
        (A) LENGTH: 267 base pairs
        (B) TYPE: nucleic acid
        (C) STRANDEDNESS: single
        (D) TOPOLOGY: linear (ii) MOLECULE TYPE: DNA (genomic)
```

(xi) SEQUENCE DESCRIPTION: SEQ ID NO:13:

| | | | |
|---|---|---|---|
| ATAGGCCCTT TGGAGACGGC TGTTTTCCAG ACTCCAAACT ATCGTGTCAC ACGTGTGGGA | 60 | | |
| AATGAAGTGT CTTTCAATTG TGAGCAAACC CTGGACCACA ATACTATGTA CTGGTACAAG | 120 | | |
| CAAGACTCTA AGAAATTGCT GAAGATTATG TTTAGCTACA ATAATAAGCA ACTCATTGTA | 180 | | |
| AACGAAACAG TTCCAAGGCG CTTCTCACCT CAGTCTTCAG ATAAAGCTCA TTTGAATCTT | 240 | | |
| CGAATCAAGT CTGTAGAGCT GGAGGAC | 267 | | |

(2) INFORMATION FOR SEQ ID NO:14:

(i) SEQUENCE CHARACTERISTICS:
        (A) LENGTH: 54 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:14:

```
Gly Pro Ser Gly Asp Gln Gly Ala Ser Gly Pro Ala Gly Pro Ser Gly
 1               5                  10                  15

Pro Arg Gly Pro Pro Gly Pro Val Gly Pro Ser Gly Lys Asp Gly Ala
            20                  25                  30

Asn Gly Ile Pro Gly Pro Ile Gly Pro Pro Gly Pro Arg Gly Arg Ser
        35                  40                  45

Gly Glu Thr Gly Pro Ala
    50
```

(2) INFORMATION FOR SEQ ID NO:15:

(i) SEQUENCE CHARACTERISTICS:
        (A) LENGTH: 731 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:15:

| | |
|---|---|
| AGAATATAGA TAGATATGTC TGTGCTGACC GTGGCCTTTT GCCTCTTCCT TCTACACAGG | 60 |
| GTCCTTCTGG AGACCAAGGT GCTTCTGGTC CTGCTGGTCC TTCTGGCCCT AGAGTAAGTG | 120 |
| ACATGGAGTT GGAAGATGGA GGGGGCCCTT CAGAGAGTGT GGGCCTGTGT TCCCATGGGG | 180 |
| AGGGAAATGC TGCTGCTTCT GGGGAAGCTG TGGGCTCAGG GGTCCTCACT CAGTAATGGG | 240 |
| GGCAGGACTG GCTCATGTGC CTATGGCCAG AAAAGCGCCT GAGGCCACAA TGGCTGTAAG | 300 |
| ACAAACATGA ATCAGCCTCT CGCTGTCAGA CAGAACAGCA TTTTACAAAG AGGAGCTTAG | 360 |
| GAGGGTAGGC AAGCCATGGA GCTATCCTGC TGGTTCTTGG CCAAATAGAG ACCAACTTAG | 420 |
| GGTTCCATGA CTGAGCATGT GAAGAACTGG GGGCGGAGTG GCTGGTGCTA TCAGGACAGC | 480 |
| CACCTACCCA GCCCCAGCGA CTCCCCAGCC TTCCCTGTGG TGACCACTCT TTCCTCACGA | 540 |
| CCTCTCTCTC TTGCAGGGTC CTCCTGGCCC CGTCGGTCCC TCTGGCAAAG ATGGTGCTAA | 600 |
| TGGAATCCCT GGCCCCATTG GGCCTCCTGG TCCCCGTGGA CGATCAGGCG AAACCGGCCC | 660 |
| TGCTGTAAGT GTCCTGACTC CTTCCCTGCT GTCGAGGTGT CCCTACCATC CGGGAGGCTT | 720 |
| GAGCTCTTTT T | 731 |

METHODS AND COMPOSITIONS FOR MULTIPLE GENE TRANSFER INTO BONE CELLS

The present application is a continuation-in-part of U. S. Ser. No. 08/199,780, now U.S. Pat. No. 5,763,416, filed Feb. 18, 1994; the entire text and figures of which disclosure are specifically incorporated herein by reference without disclaimer. The United States government has certain rights in the present invention pursuant to Grants AR40673, AR40679 and AR4242 from the National Institutes of Health.

BACKGROUND OF THE INVENTION

1. Field of the Invention

The present invention relates generally to the field of bone cells and tissues. More particularly, certain embodiments concern the transfer of genetic material into bone and other embodiments concern type II collagen. In certain examples, the invention concerns the use of type II collagen and nucleic acids to stimulate bone growth, repair and regeneration. Methods, compositions, kits and devices are provided for transferring an osteotropic gene into bone progenitor cells, which is shown to stimulate progenitor cells and to promote increased bone formation in vivo.

2. Description of the Related Art

Defects in the process of bone repair and regeneration are linked to the development of several human diseases and disorders, e.g., osteoporosis and osteogenesis imperfecta. Failure of the bone repair mechanism is, of course, also associated with significant complications in clinical orthopaedic practice, for example, fibrous non-union following bone fracture, implant interface failures and large allograft failures. The lives of many individuals would be improved by the development of new therapies designed to stimulate and strengthen the fracture repair process.

Naturally, any new technique to stimulate bone repair would be a valuable tool in treating bone fractures. A significant portion of fractured bones are still treated by casting, allowing natural mechanisms to effect wound repair. Although there have been advances in fracture treatment in recent years, including improved devices, the development of new processes to stimulate, or complement, the wound repair mechanisms would represent significant progress in this area.

A very significant patient population that would benefit from new therapies designed to promote fracture repair, or even prevent or lessen fractures, are those patients suffering from osteoporosis. The term osteoporosis refers to a heterogeneous group of disorders characterized by decreased bone mass and fractures. Clinically, osteoporosis is segregated into type I and type II. Type I osteoporosis occurs predominantly in middle aged women and is associated with estrogen loss at the menopause, while osteoporosis type II is associated with advancing age.

An estimated 20–25 million people are at increased risk for fracture because of site-specific bone loss. The cost of treating osteoporosis in the United States is currently estimated to be in the order of $10 billion per year. Demographic trends, i.e., the gradually increasing age of the US population, suggest that these costs may increase 2–3 fold by the year 2020 if a safe and effective treatment is not found.

The major focus of current therapies for osteoporosis is fracture prevention, not fracture repair. This is an important consideration, as it is known that significant morbidity and mortality are associated with prolonged bed rest in the elderly, especially those who have suffered hip fracture. New methods are clearly needed for stimulating fracture repair, thus restoring mobility in these patients before the complications arise.

Osteogenesis imperfecta (OI) refers to a group of inherited connective tissue diseases characterized by bone and soft connective tissue fragility (Byers & Steiner, 1992; Prockop, 1990). Males and females are affected equally, and the overall incidence is currently estimated to be 1 in 5,000–14,000 live births. Hearing loss, dentinogenesis imperfecta, respiratory insufficiency, severe scoliosis and emphysema are just some of the conditions that are associated with one or more types of OI. While accurate estimates of the health care costs are not available, the morbidity and mortality associated with OI certainly result from the extreme propensity to fracture (OI types I–IV) and the deformation of abnormal bone following fracture repair (OI types II–IV) (Bonadio & Goldstein, 1993). The most relevant issue with OI treatment is to develop new methods by which to improve fracture repair and thus to improve the quality of life of these patients.

The techniques of bone reconstruction, such as is used to reconstruct defects occurring as a result of trauma, cancer surgery or errors in development, would also be improved by new methods to promote bone repair. Reconstructive methods currently employed, such as using autologous bone grafts, or bone grafts with attached soft tissue and blood vessels, are associated with significant drawbacks of both cost and difficulty. For example, harvesting a useful amount of autologous bone is not easily achieved, and even autologous grafts often become infected or suffer from resorption.

The process of bone repair and regeneration resembles the process of wound healing in other tissues. A typical sequence of events includes; hemorrhage; clot formation; dissolution of the clot with concurrent removal of damaged tissues; ingrowth of granulation tissue; formation of cartilage; capillary ingrowth and cartilage turnover; rapid bone formation (callus tissue); and, finally, remodeling of the callus into cortical and trabecular bone. Therefore, bone repair is a complex process that involves many cell types and regulatory molecules. The diverse cell populations involved in fracture repair include stem cells, macrophages, fibroblasts, vascular cells, osteoblasts, chondroblasts, and osteoclasts.

Regulatory factors involved in bone repair are known to include systemic hormones, cytokines, growth factors, and other molecules that regulate growth and differentiation. Various osteoinductive agents have been purified and shown to be polypeptide growth-factor-like molecules. These stimulatory factors are referred to as bone morphogenetic or morphogenic proteins (BMPs), and have also been termed osteogenic bone inductive proteins or osteogenic proteins (OPs). Several BMP (or OP) genes have now been cloned, and the common designations are BMP-1 through BMP-8. Although the BMP terminology is widely used, it may prove to be the case that there is an OP counterpart term for every individual BMP (Alper, 1994).

BMPs 2–8 are generally thought to be osteogenic, although BMP-1 is a more generalized morphogen (Shimell et al., 1991). BMP-3 is also called osteogenin (Luyten et al., 1989) and BMP-7 is also called OP-1 (Ozkaynak et al., 1990). BMPs are related to, or part of, the transforming growth factor-β (TGF-β) superfamily, and both TGF-β1 and TGF-β2 also regulates osteoblast function (Seitz et al., 1992). Several BMP (or OP) nucleotide sequences and polypeptides have been described in U.S. Pat. Nos. e.g., 4,795,804; 4,877,864; 4,968,590; 5,108,753; including, specifically, BMP-1 disclosed in U.S. Pat. No. 5,108,922; BMP-2A (currently referred to as BMP-2) in U.S. Pat. Nos. 5,166,058 and 5,013,649; BMP-2B (currently referred to as BMP-4) disclosed in U.S. Pat. No. 5,013,649; BMP-3 in 5,116,738; BMP-5 in 5,106,748; BMP-6 in 5,187,076; BMP-7 in 5,108,753 and 5,141,905; and OP-1, COP-5 and COP-7 in 5,011,691.

Other growth factors or hormones that have been reported to have the capacity to stimulate new bone formation include acidic fibroblast growth factor (Jingushi et al., 1990); estrogen (Boden et al., 1989); macrophage colony stimulating factor (Horowitz et al., 1989); and calcium regulatory agents such as parathyroid hormone (PTH) (Raisz & Kream, 1983).

Several groups have investigated the possibility of using bone stimulating proteins and polypeptides, particularly recombinant BMPs, to influence bone repair in vivo. For example, recombinant BMP-2 has been employed to repair surgically created defects in the mandible of adult dogs (Toriumi et al., 1991), and high doses of this molecule have been shown to functionally repair segmental defects in rat femurs (Yasko et al., 1992). Chen and colleagues showed that a single application of 25–100 mg of recombinant TGF-$\beta$1 adjacent to cartilage induced endochondral bone formation in the rabbit ear full thickness skin wounds (Chen et al., 1991). It has also been reported that an application of TGF-$\beta$1 in a 3% methylcellulose gel was able to repair surgically induced large skull defects that otherwise heal by fibrous connective tissue and never form bone (Beck et al., 1991).

However, there are many drawbacks associated with these type of treatment protocols, not least the expensive and time-consuming purification of the recombinant proteins from their host cells. Also, polypeptides, once administered to an animal are more unstable than is generally desired for a therapeutic agent, and they are susceptible to proteolytic attack. Furthermore, the administration of recombinant proteins can initiate various inhibitive or otherwise harmful immune responses. It is clear, therefore, that a new method capable of promoting bone repair and regeneration in vivo would represent a significant scientific and medical advance with immediate benefits to a large number of patients. A method readily adaptable for use with a variety of matrices and bone-stimulatory genes would be particularly advantageous.

SUMMARY OF THE INVENTION

The present invention overcomes one or more of these and other drawbacks inherent in the prior art by providing novel methods, compositions and devices for use in transferring nucleic acids into bone cells and tissues, and for promoting bone repair and regeneration. Certain embodiments of the invention rest, generally, with the inventors' surprising finding that nucleic acids can be effectively transferred to bone progenitor cells in vivo and that, in certain embodiments, the transfer of an osteotropic gene stimulates bone repair in an animal.

The invention, in general terms, thus concerns methods, compositions and devices for transferring a nucleic acid segment into bone progenitor cells or tissues. The methods of the invention generally comprise contacting bone progenitor cells with a composition comprising a nucleic acid segment in a manner effective to transfer the nucleic acid segment into the cells. The cells may be cultured cells or recombinant cells maintained in vitro, when all that is required is to add the nucleic acid composition to the cells, e.g., by adding it to the culture media.

Alternatively, the progenitor cells may be located within a bone progenitor tissue site of an animal, when the nucleic acid composition would be applied to the site in order to effect, or promote, nucleic acid transfer into bone progenitor cells in vivo. In transferring nucleic acids into bone cells within an animal, a preferred method involves first adding the genetic material to a bone-compatible matrix and then using the impregnated matrix to contact an appropriate tissue site within the animal.

An extremely wide variety of genetic material can be transferred to bone progenitor cells or tissues using the compositions and methods of the invention. For example, the nucleic acid segment may be DNA (double or single-stranded) or RNA (e.g., mRNA, tRNA, rRNA); it may also be a "coding segment", i.e., one that encodes a protein or polypeptide, or it may be an antisense nucleic acid molecule, such as antisense RNA that may function to disrupt gene expression. The nucleic acid segments may thus be genomic sequences, including exons or introns alone or exons and introns, or coding cDNA regions, or in fact any construct that one desires to transfer to a bone progenitor cell or tissue. Suitable nucleic acid segments may also be in virtually any form, such as naked DNA or RNA, including linear nucleic acid molecules and plasmids; functional inserts within the genomes of various recombinant viruses, including viruses with DNA genomes and retroviruses; and any form of nucleic acid segment, plasmid or virus associated with a liposome or a gold particle, the latter of which may be employed in connection with the gene gun technology.

The invention may be employed to promote expression of a desired gene in bone cells or tissues and to impart a particular desired phenotype to the cells. This expression could be increased expression of a gene that is normally expressed (i.e., "over-expression"), or it could be used to express a gene that is not normally associated with bone progenitor cells in their natural environment. Alternatively, the invention may be used to suppress the expression of a gene that is naturally expressed in such cells and tissues, and again, to change or alter the phenotype. Gene suppression may be a way of expressing a gene that encodes a protein that exerts a down-regulatory function, or it may utilize antisense technology.

Bone Progenitor Cells and Tissues

In certain embodiments, this invention provides advantageous methods for using genes to stimulate bone progenitor cells. As used herein, the term "bone progenitor cells" refers to any or all of those cells that have the capacity to ultimately form, or contribute to the formation of, new bone tissue. This includes various cells in different stages of differentiation, such as, for example, stem cells, macrophages, fibroblasts, vascular cells, osteoblasts, chondroblasts, osteoclasts, and the like. Bone progenitor cells also include cells that have been isolated and manipulated in vitro, e.g., subjected to stimulation with agents such as cytokines or growth factors or even genetically engineered cells. The particular type or types of bone progenitor cells that are stimulated using the methods and compositions of the invention are not important, so long as the cells are stimulated in such a way that they are activated and, in the context of in vivo embodiments, ultimately give rise to new bone tissue.

The term "bone progenitor cell" is also used to particularly refer to those cells that are located within, are in contact with, or migrate towards (i.e., "home to"), bone progenitor tissue and which cells directly or indirectly stimulate the formation of mature bone. As such, the progenitor cells may be cells that ultimately differentiate into mature bone cells themselves, i.e., cells that "directly" form new bone tissue. Cells that, upon stimulation, attract further progenitor cells or promote nearby cells to differentiate into bone-forming cells (e.g., into osteoblasts, osteocytes and/or osteoclasts) are also considered to be progenitor cells in the context of this disclosure—as their stimulation "indirectly" leads to bone repair or regeneration. Cells affecting bone formation indirectly may do so by the elaboration of various growth factors or cytokines, or by their physical interaction with other cell types. Although of scientific interest, the direct or indirect mechanisms by which progenitor cells stimulate bone or wound repair is not a consideration in practicing this invention.

Bone progenitor cells and bone progenitor tissues may be cells and tissues that, in their natural environment, arrive at an area of active bone growth, repair or regeneration (also referred to as a wound repair site). In terms of bone progenitor cells, these may also be cells that are attracted or recruited to such an area. These may be cells that are present within an artificially-created osteotomy site in an animal model, such as those disclosed herein. Bone progenitor cells may also be isolated from animal or human tissues and maintained in an in vitro environment. Suitable areas of the body from which to obtain bone progenitor cells are areas such as the bone tissue and fluid surrounding a fracture or other skeletal defect (whether or not this is an artificially created site), or indeed, from the bone marrow. Isolated cells may be stimulated using the methods and compositions disclosed herein and, if desired, be returned to an appropriate site in an animal where bone repair is to be stimulated. In such cases, the nucleic-acid containing cells would themselves be a form of therapeutic agent. Such ex vivo protocols are well known to those of skill in the art.

In important embodiments of the invention, the bone progenitor cells and tissues will be those cells and tissues that arrive at the area of bone fracture or damage that one desires to treat. Accordingly, in treatment embodiments, there is no difficulty associated with the identification of suitable target progenitor cells to which the present therapeutic compositions should be applied. All that is required in such cases is to obtain an appropriate stimulatory composition, as disclosed herein, and contact the site of the bone fracture or defect with the composition. The nature of this biological environment is such that the appropriate cells will become activated in the absence of any further targeting or cellular identification by the practitioner.

Certain methods of the invention involve, generally, contacting bone progenitor cells with a composition comprising one or more osteotropic genes (with or without additional genes, proteins or other biomolecules) so as to promote expression of said gene in said cells. As outlined above, the cells may be contacted in vitro or in vivo. This is achieved, in the most direct manner, by simply obtaining a functional osteotropic gene construct and applying the construct to the cells. The present inventors surprisingly found that there are no particular molecular biological modifications that need to be performed in order to promote effective expression of the gene in progenitor cells. Contacting the cells with DNA, e.g., a linear DNA molecule, or DNA in the form of a plasmid or other recombinant vector, that contains the gene of interest under the control of a promoter, along with the appropriate termination signals, is sufficient to result in uptake and expression of the DNA, with no further steps necessary.

In preferred embodiments, the process of contacting the progenitor cells with the osteotropic gene composition is conducted in vivo. Again, a direct consequence of this process is that the cells take up and express the gene and that they, without additional steps, function to stimulate bone tissue growth, repair or regeneration.

An assay of an osteoinductive gene may be conducted using the bone induction bioassay of Sampath & Reddi (1981; incorporated herein by reference). This is a rat bone formation assay that is routinely used to evaluate the osteogenic activity of bone inductive factors. However, for analyzing the effects of osteotropic genes on bone growth, one is generally directed to use the novel osteotomy model disclosed herein.

Osteotropic Genes

As used herein, the terms "osteotropic and osteogenic gene" are used to refer to a gene or DNA coding region that encodes a protein, polypeptide or peptide that is capable of promoting, or assisting in the promotion of, bone formation, or one that increases the rate of primary bone growth or healing (or even a gene that increases the rate of skeletal connective tissue growth or healing). The terms promoting, inducing and stimulating are used interchangeably throughout this text to refer to direct or indirect processes that ultimately result in the formation of new bone tissue or in an increased rate of bone repair. Thus, an osteotropic gene is a gene that, when expressed, causes the phenotype of a cell to change so that the cell either differentiates, stimulates other cells to differentiate, attracts bone-forming cells, or otherwise functions in a manner that ultimately gives rise to new bone tissue.

In using the new osteotomy model of the invention, an osteotropic gene is characterized as a gene that is capable of stimulating proper bone growth in the osteotomy gap to any degree higher than that observed in control studies, e.g., parallel studies employing an irrelevant marker gene such as $\beta$-galactosidase. This stimulation of "proper bone growth" includes both the type of tissue growth and the rate of bone formation. In using the model with a 5 mm osteotomy gap, an osteotropic gene is generally characterized as a gene that is capable of promoting or inducing new bone formation, rather than abnormal bone fracture repair, i.e. fibrous nonunion. In using the 2 mm osteotomy gap, one may characterize osteotropic genes as genes that increase the rate of primary bone healing as compared to controls, and more preferably, genes capable of stimulating repair of the osteotomy defect in a time period of less than nine weeks.

In general terms, an osteotropic gene may also be characterized as a gene capable of stimulating the growth or regeneration of skeletal connective tissues such as, e.g., tendon, cartilage, and ligament. Thus, in certain embodiments, the methods and compositions of the invention may be employed to stimulate the growth or repair of both bone tissue itself and also of skeletal connective tissues.

A variety of osteotropic genes are now known, all of which are suitable for use in connection with the present invention. Osteotropic genes and the proteins that they encode include, for example, systemic hormones, such as parathyroid hormone (PTH) and estrogen; many different growth factors and cytokines; chemotactic or adhesive peptides or polypeptides; molecules such as activin (U.S. Pat. No. 5,208,219, incorporated herein by reference); specific bone morphogenetic proteins (BMPs); and even growth factor receptor genes.

Examples of suitable osteotropic growth factors include those of the transforming growth factor (TGF) gene family, including TGFs 1–4, and particularly TGF-β1, TGF-β2 and TGF-β2, (U.S. Pat. Nos. 4,886,747 and 4,742,003, incorporated herein by reference), with TGF-α (U.S. Pat. No. 5,168,051, incorporated herein by reference) also being of possible use; and also fibroblast growth factors (FGF), such as acidic FGF and kFGF; granulocyte/macrophage colony stimulating factor (GMCSF); epidermal growth factor (EGF); platelet derived growth factor (PDGF); insulin-like growth factors (IGF), including IGF-I and IGF-II; and leukemia inhibitory factor (LIF), also known as HILDA and DIA. Any of the above or other related genes, or DNA segments encoding the active portions of such proteins, may be used in the novel methods and compositions of the invention.

Certain preferred osteotropic genes and DNA segments are those of the TGF superfamily, such as TGF-β1, TGF-β2, TGF-β3 and members of the BMP family of genes. For example, several BMP genes have been cloned that are ideal candidates for use in the nucleic acid transfer or delivery protocols of the invention. Suitable BMP genes are those designated BMP-2 through BMP-12. BMP-1 is not considered to be particularly useful at this stage.

There is considerable variation in the terminology currently employed in the literature in referring to these genes and polypeptides. It will be understood by those of skill in the art that all BMP genes that encode an active osteogenic protein are considered for use in this invention, regardless of the differing terminology that may be employed. For example, BMP-3 is also called osteogenin and BMP-7 is also called OP-1 (osteogenic protein-1). It is likely that the family of factors termed OP(s) is as large as that termed BMP(s), and that these terms, in fact, describe the same set of molecules (Alper, 1994).

The DNA sequences for several BMP (or OP) genes have been described both in scientific articles and in U.S. Pat. Nos. such as 4,877,864; 4,968,590; 5,108,753. Specifically, BMP-1 sequences are disclosed in U.S. Pat. No. 5,108,922; BMP-2A (currently referred to as BMP-2) in U.S. Pat. Nos. 5,166,058 and 5,013,649; BMP-2B (currently referred to as BMP-4) disclosed in U.S. Pat. No. 5,013,649; BMP-3 in 5,116,738; BMP-5 in 5,106,748; BMP-6 in 5,187,076; and BMP-7 in 5,108,753 and 5,141,905; all incorporated herein by reference). The article by Wozney et al. (1988; incorporated herein by reference) is considered to be particularly useful for describing BMP molecular clones and their activities. DNA sequences encoding the osteogenic proteins designated OP-1, COP-5 and COP-7 are also disclosed in U.S. Pat. No. 5,011,691.

All of the above issued U.S. Patents are incorporated herein by reference and are intended to be used in order to supplement the present teachings regarding the preparation of BMP and OP genes and DNA segments that express osteotropic polypeptides. As disclosed in the above patents, and known to those of skill in the art, the original source of a recombinant gene or DNA segment to be used in a therapeutic regimen need not be of the same species as the animal to be treated. In this regard, it is contemplated that any recombinant PTH, TGF or BMP gene may be employed to promote bone repair or regeneration in a human subject or an animal, such as, e.g., a horse. Particularly preferred genes are those from human, mouse and bovine sources, in that such genes and DNA segments are readily available, with the human or mouse forms of the gene being most preferred for use in human treatment regimens. Recombinant proteins and polypeptides encoded by isolated DNA segments and genes are often referred to with the prefix "r" for recombinant and "rh" for recombinant human. As such, DNA segments encoding rBMPs, such as rhBMP-2 or rhBMP-4, are contemplated to be particularly useful in connection with this invention.

The definition of a "BMP gene", as used herein, is a gene that hybridizes, under relatively stringent hybridization conditions (see, e.g., Mainiatis et al., 1982, Molecular Cloning: A Laboratory Manual, Cold Spring Harbor Laboratory), to DNA sequences presently known to include BMP gene sequences.

To prepare an osteotropic gene segment or cDNA one may follow the teachings disclosed herein and also the teachings of any of patents or scientific documents specifically referenced herein. Various nucleotide sequences encoding active BMPs are disclosed in U.S. Pat. Nos. 5,166,058, 5,013,649, 5,116,738, 5,106,748, 5,187,076, 5,108,753 and 5,011,691, each incorporated herein by reference. By way of example only, U.S. Pat. No. 5,166,058, teaches that hBMP-2 is encoded by a nucleotide sequence from nucleotide #356 to nucleotide #1543 of the sequence shown in Table II of the patent. One may thus obtain a hBMP-2 DNA segment using molecular biological techniques, such as polymerase chain reaction (PCR") or screening a CDNA or genomic library, using primers or probes with sequences based on the above nucleotide sequence. The practice of such techniques is a routine matter for those of skill in the art, as taught in various scientific articles, such as Sambrook et al. (1989), incorporated herein by reference. Certain documents further particularly describe suitable mammalian expression vectors, e.g., U.S. Pat. No. 5,168,050, incorporated herein by reference.

Osteotropic genes and DNA segments that are particularly preferred for use in certain aspects of the present compositions and methods are the TGF, PTH and BMP genes. TGF genes are described in U.S. Pat. Nos. 5,168,051; 4,886,747 and 4,742,003, each incorporated herein by reference. TGFα may not be as widely applicable as TGFβ, but is proposed for use particularly in applications involving skeletal soft tissues. The PTH gene, or a DNA segment encoding the active fragment thereof, such as a DNA segment encoding a polypeptide that includes the amino acids 1–34 (hPTH1-34; Hendy et al., 1981; incorporated herein by reference) is another preferred gene; as are the BMP genes termed BMP-4 and BMP-2, such as the gene or CDNA encoding the mouse BMP-4 disclosed herein.

It is also contemplated that one may clone further genes or cDNAs that encode an osteotropic protein or polypeptide. The techniques for cloning DNA molecules, i.e., obtaining a specific coding sequence from a DNA library that is distinct from other portions of DNA, are well known in the art. This can be achieved by, for example, screening an appropriate DNA library, as disclosed in Example XIII herein, which relates to the cloning of a wound healing gene. The screening procedure may be based on the hybridization of oligonucleotide probes, designed from a consideration of portions of the amino acid sequence of known DNA sequences encoding related osteogenic proteins. The operation of such screening protocols are well known to those of skill in the art and are described in detail in the scientific literature, for example, in Sambrook et al. (1989), incorporated herein by reference.

Osteotropic genes with sequences that vary from those described in the literature are also encompassed by the invention, so long as the altered or modified gene still encodes a protein that functions to stimulate bone progenitor cells in any direct or indirect manner. These sequences include those caused by point mutations, those due to the degeneracies of the genetic code or naturally occurring allelic variants, and further modifications that have been introduced by genetic engineering, i.e., by the hand of man.

Techniques for introducing changes in nucleotide sequences that are designed to alter the functional properties of the encoded proteins or polypeptides are well known in the art, e.g., U.S. Pat. No. 4,518,584, incorporated herein by reference, which techniques are also described in further detail herein. Such modifications include the deletion, insertion or substitution of bases, and thus, changes in the amino acid sequence. Changes may be made to increase the osteogenic activity of a protein, to increase its biological stability or half-life, to change its glycosylation pattern, and the like. All such modifications to the nucleotide sequences are encompassed by this invention.

It will, of course, be understood that one or more than one osteotropic gene may be used in the methods and compositions of the invention. The nucleic acid delivery methods may thus entail the administration of one, two, three, or more, osteotropic genes. The maximum number of genes that may be applied is limited only by practical considerations, such as the effort involved in simultaneously preparing a large number of gene constructs or even the possibility of eliciting an adverse cytotoxic effect. The particular combination of genes may be two or more distinct BMP genes; or it may be such that a growth factor gene is combined with a hormone gene, e.g. a BMP gene and a PTH gene; a hormone or growth factor gene may even be combined with a gene encoding a cell surface receptor capable of interacting with the polypeptide product of the first gene.

In using multiple genes, they may be combined on a single genetic construct under control of one or more promoters, or they may be prepared as separate constructs of the same of different types. Thus, an almost endless combination of different genes and genetic constructs may be employed. Certain gene combinations may be designed to, or their use may otherwise result in, achieving synergistic effects on cell stimulation and bone growth, any and all such combinations are intended to fall within the scope of the present invention. Indeed, many synergistic effects have been described in the scientific literature, so that one of ordinary skill in the art would readily be able to identify likely synergistic gene combinations, or even gene-protein combinations.

It will also be understood that, if desired, the nucleic segment or gene could be administered in combination with further agents, such as, e.g. proteins or polypeptides or various pharmaceutically active agents. So long as genetic material forms part of the composition, there is virtually no limit to other components which may also be included, given that the additional agents do not cause a significant adverse effect upon contact with the target cells or tissues. The nucleic acids may thus be delivered along with various other agents, for example, in certain embodiments one may wish to administer an angiogenic factor, and/or an inhibitor of bone resorption, as disclosed in U.S. Pat. Nos. 5,270,300 and 5,118,667, respectively, each incorporated herein by reference.

Gene Constructs and DNA Segments

As used herein, the terms "gene" and "DNA segment" are both used to refer to a DNA molecule that has been isolated free of total genomic DNA of a particular species. Therefore, a gene or DNA segment encoding an osteotropic gene refers to a DNA segment that contains sequences encoding an osteotropic protein, but is isolated away from, or purified free from, total genomic DNA of the species from which the DNA is obtained. Included within the term "DNA segment", are DNA segments and smaller fragments of such segments, and also recombinant vectors, including, for example, plasmids, cosmids, phage, retroviruses, adenoviruses, and the like.

The term "gene" is used for simplicity to refer to a functional protein or peptide encoding unit. As will be understood by those in the art, this functional term includes both genomic sequences and cDNA sequences. "Isolated substantially away from other coding sequences" means that the gene of interest, in this case, an osteotropic gene, forms the significant part of the coding region of the DNA segment, and that the DNA segment does not contain large portions of naturally-occurring coding DNA, such as large chromosomal fragments or other functional genes or cDNA coding regions. of course, this refers to the DNA segment as originally isolated, and does not exclude genes or coding regions, such as sequences encoding leader peptides or targeting sequences, later added to the segment by the hand of man.

This invention provides novel ways in which to utilize various known osteotropic DNA segments and recombinant vectors. As described above, many such vectors are readily available, one particular detailed example of a suitable vector for expression in mammalian cells is that described in U.S. Pat. No. 5,168,050, incorporated herein by reference. However, there is no requirement that a highly purified vector be used, so long as the coding segment employed encodes a osteotropic protein and does not include any coding or regulatory sequences that would have an adverse effect on bone progenitor cells. Therefore, it will also be understood that useful nucleic acid sequences may include additional residues, such as additional non-coding sequences flanking either of the 5' or 3' portions of the coding region or may include various internal sequences, i.e., introns, which are known to occur within genes.

After identifying an appropriate osteotropic gene or DNA molecule, it may be inserted into any one of the many vectors currently known in the art, so that it will direct the expression and production of the osteotropic protein when incorporated into a bone progenitor cell. In a recombinant expression vector, the coding portion of the DNA segment is positioned under the control of a promoter. The promoter may be in the form of the promoter which is naturally associated with an osteotropic gene, as may be obtained by isolating the 5' non-coding sequences located upstream of the coding segment or exon, for example, using recombinant cloning and/or PCR technology, in connection with the compositions disclosed herein.

In other embodiments, it is contemplated that certain advantages will be gained by positioning the coding DNA segment under the control of a recombinant, or heterologous, promoter. As used herein, a recombinant or heterologous promoter is intended to refer to a promoter that is not normally associated with an osteotropic gene in its natural environment. Such promoters may include those normally associated with other osteotropic genes, and/or promoters isolated from any other bacterial, viral, eukaryotic, or mammalian cell. Naturally, it will be important to employ a promoter that effectively directs the expression of the DNA segment in bone progenitor cells.

The use of recombinant promoters to achieve protein expression is generally known to those of skill in the art of molecular biology, for example, see Sambrook et al. (1989). The promoters employed may be constitutive, or inducible, and can be used under the appropriate conditions to direct high level or regulated expression of the introduced DNA segment. The currently preferred promoters are those such as CMV, RSV LTR, the SV40 promoter alone, and the SV40 promoter in combination with the SV40 enhancer.

Osteotropic genes and DNA segments may also be in the form of a DNA insert which is located within the genome of a recombinant virus, such as, for example a recombinant adenovirus, adeno-associated virus (AAV) or retrovirus. In such embodiments, to place the gene in contact with a bone progenitor cell, one would prepare the recombinant viral particles, the genome of which includes the osteotropic gene insert, and simply contact the progenitor cells or tissues with the virus, whereby the virus infects the cells and transfers the genetic material.

In preferred embodiments, one would impregnate a matrix or implant material with virus by soaking the material in recombinant virus stock solution, e.g., for 1–2 hours, and then contact the bone progenitor cells or tissues with the impregnated matrix. Cells then penetrate, or grow into, the matrix, thereby contacting the virus and allowing viral infection which leads to the cells taking up the desired gene or cDNA and expressing the encoded protein.

Bone-Compatible Matrices

In certain preferred embodiments, the methods of the invention involved preparing a composition in which the osteotropic gene, genes, DNA segments, or cells already incorporating such genes or segments, are associated with, or impregnated within, a bone-compatible matrix, to form a "matrix-gene composition" and the matrix-gene composition is then placed in contact with the bone progenitor cells or tissue. The matrix may become impregnated with a gene DNA segment simply by soaking the matrix in a solution containing the DNA, such as a plasmid solution, for a brief period of time of anywhere from about 5 minutes or so, up to and including about an hour. Matrix-gene compositions are all those in which a gene is adsorbed, absorbed, or otherwise maintained in contact with the matrix.

The type of matrix that may be used in the compositions, devices and methods of the invention is virtually limitless, so long as it is a "bone-compatible matrix". This means that the matrix has all the features commonly associated with being "biocompatible", in that it is in a form that does not produce an adverse, allergic or other untoward reaction when administered to an animal, and it is also suitable for placing in contact with bone tissue. This latter requirement takes into consideration factors such as the capacity of the matrix to provide a structure for the developing bone and, preferably, its capacity to resorbed into the body after the bone has been repaired.

The choice of matrix material will differ according to the particular circumstances and the site of the bone that is to be treated. Matrices such as those described in U.S. Pat. No. 5,270,300 (incorporated herein by reference) may be employed. Physical and chemical characteristics, such as, e.g., biocompatibility, biodegradability, strength, rigidity, interface properties and even cosmetic appearance may be considered in choosing a matrix, as is well known to those of skill in the art. Appropriate matrices will both deliver the gene composition and also provide a surface for new bone growth, i.e., will act as an in situ scaffolding through which progenitor cells may migrate.

A particularly important aspect of the present invention is its use in connection with orthopaedic implants and interfaces and artificial joints, including implants themselves and functional parts of an implant, such as, e.g., surgical screws, pins, and the like. In preferred embodiments, it is contemplated that the metal surface or surfaces of an implant or a portion thereof, such as a titanium surface, will be coated with a material that has an affinity for nucleic acids, most preferably, with hydroxyl apatite, and then the coated-metal will be further coated with the gene or nucleic acid that one wishes to transfer. The available chemical groups of the absorptive material, such as hydroxyl apatite, may be readily manipulated to control its affinity for nucleic acids, as is known to those of skill in the art.

In certain embodiments, non-biodegradable matrices may be employed, such as sintered hydroxyapatite, bioglass, aluminates, other bioceramic materials and metal materials, particularly titanium. A suitable ceramic delivery system is that described in U.S. Pat. No. 4,596,574, incorporated herein by reference. Polymeric matrices may also be employed, including acrylic ester polymers and lactic acid polymers, as disclosed in U.S. Pat. Nos. 4,526,909, and 4,563,489, respectively, each incorporated herein by reference.

In preferred embodiments, it is contemplated that a biodegradable matrix will likely be most useful. A biodegradable matrix is generally defined as one that is capable of being resorbed into the body. Potential biodegradable matrices for use in connection with the compositions, devices and methods of this invention include, for example, biodegradable and chemically defined calcium sulfate, tricalciumphosphate, hydroxyapatite, polylactic acid, polyanhydrides, matrices of purified proteins, and semi-purified extracellular matrix compositions.

A particularly preferred group of matrices are those prepared from tendon or dermal collagen, as may be obtained from a variety of commercial sources, such as e.g., Sigma and Collagen Corporation, or collagen matrices prepared as described in U.S. Pat. Nos. 4,394,370 and 4,975,527, each incorporated herein by reference. One preferred collagenous material is that termed UltraFiber™, obtainable from Norian Corp. (Mountain View, Calif.).

The various collagenous materials may also be in the form of mineralized collagen. U.S. Pat. No. 5,231,169, incorporated herein by reference, describes the preparation of mineralized collagen through the formation of calcium phosphate mineral under mild agitation in situ in the presence of dispersed collagen fibrils. Such a formulation may be employed in the context of delivering a nucleic acid segment to a bone tissue site.

Certain other preferred collagenous materials are those based upon type II collagen. Type II collagen preparations have been discovered to have the surprising and advantageous property of, absent any osteotropic gene, being capable of stimulating bone progenitor cells. Prior to the present invention, it was thought that type II collagen only had a structural role in the extracellular matrix and the present finding that type II collagen is actually an osteoconductive/osteoinductive material is unexpected. The present invention thus contemplates the use of a variety of type II collagen preparations as bone cell stimulants, either with or without DNA segments, including native type II collagen, as prepared from cartilage, and recombinant type II collagen.

Nucleic Acid Transfer Embodiments

Once a suitable matrix-gene composition has been prepared or obtained, all that is required to deliver the osteotropic gene to bone progenitor cells within an animal is to place the matrix-gene composition in contact with the site in the body in which one wishes to promote bone growth. This could be a simple bone fracture site that one wishes to repair, an area of weak bone, such as in a patient with osteoporosis, or a bone cavity site that one wishes to fill with new bone tissue. Bone cavities may arise as a result of an inherited disorder, birth defect, or may result following dental or periodontal surgery or after the removal of an osteosarcoma.

The amount of gene construct that is applied to the matrix and the amount of matrix-gene material that is applied to the bone tissue will be determined by the attending physician or veterinarian considering various biological and medical factors. For example, one would wish to consider the particular osteotropic gene and matrix, the amount of bone weight desired to be formed, the site of bone damage, the condition of the damaged bone, the patient's or animal's age, sex, and diet, the severity of any infection, the time of administration and any further clinical factors that may affect bone growth, such as serum levels of various factors and hormones. The suitable dosage regimen will therefore be readily determinable by one of skill in the art in light of the present disclosure, bearing in mind the individual circumstances.

In treating humans and animals, progress may be monitored by periodic assessment of bone growth and/or repair, e.g., using x-rays. The therapeutic methods and compositions of the invention are contemplated for use in both medical and veterinary applications, due to the lack of species specificity in bone inductive factors. In particular, it is contemplated that domestic, farm and zoological animals, as well as thoroughbred horses, would be treatable using the nucleic acid transfer protocols disclosed herein.

The present methods and compositions may also have prophylactic uses in closed and open fracture reduction and also in the improved fixation of artificial joints. The invention is applicable to stimulating bone repair in congenital, trauma-induced, or oncologic resection-induced craniofacial defects, and also is useful in the treatment of periodontal disease and other tooth repair processes and even in cosmetic plastic surgery. The matrix-gene compositions and devices of this invention may also be used in wound healing and related tissue repair, including, but not limited to healing of burns, incisions and ulcers.

The present invention also encompasses DNA-based compositions for use in cellular transfer to treat bone defects and disorders. The compositions of the invention generally comprise an osteotropic gene in association with a bone-compatible matrix, such as type II collagen, wherein the composition is capable of stimulating bone growth, repair or regeneration upon administration to, or implantation within, a bone progenitor tissue site of an animal. The osteotropic gene or genes may be any of those described above, with TGF-α (for soft skeletal tissues), TGF-β1, TGF-β2, TGF-β2, PTH, BMP-2 and BMP-4 genes being generally preferred. Likewise, irrespective of the choice of gene, the bone-compatible matrix may be any of those described above, with biodegradable matrices such as collagen and, more particularly, type II collagen, being preferred.

In still further embodiments, the present invention concerns osteotropic devices, which devices may be generally considered as molded or designed matrix-gene compositions. The devices of the invention naturally comprise a bone-compatible matrix in which an osteotropic gene is associated with the matrix. The combination of genes and matrix components is such that the device is capable of stimulating bone growth or healing when implanted in an animal. The devices may be of virtually any size or shape, so that their dimensions are adapted to fit a bone fracture or bone cavity site in the animal that is to be treated, allowing the fracture join and/or bone regrowth to be more uniform. Other particularly contemplated devices are those that are designed to act as an artificial joint. Titanium devices and hydroxylapatite-coated titanium devices will be preferred in certain embodiments. Parts of devices in combination with an osteotropic nucleic acid segment, such as a DNA-coated screw for an artificial joint, and the like, also fall within the scope of the invention.

Therapeutic kits comprising, in suitable container means, a bone compatible matrix, such as type II collagen, and an osteotropic gene form another aspect of the invention. Such kits will generally contain a pharmaceutically acceptable formulation of the matrix and a pharmaceutically acceptable formulation of an osteotropic gene, such as PTH, BMP, TGF-β, FGF, GMCSF, EGF, PDGF, IGF or a LIF gene. Currently preferred genes include PTH, TGF-β1, TGF-β2, TGF-β3, and BMP-4 genes.

The kits may comprise a single container means that contains both the biocompatible matrix and the osteotropic gene. In this sense, the container means may contain a pharmaceutically acceptable sterile gelatinous matrix having associated with it, the osteotropic gene composition. The gelatinous matrix-DNA formulation may be in the form of a syringeable composition, e.g., a type II collagen-DNA composition. In which cases, the container means may itself be a syringe, pipette, or other such like apparatus, from which the matrix-DNA material may be applied to a bone tissue site or wound area. However, the single container means may contain a dry, or lyophilized, mixture of a matrix and osteotropic gene composition, which may or may not require pre-wetting before use.

Alternatively, the kits of the invention may comprise distinct container means for each component. In such cases, one container would contain the osteotropic gene, either as a sterile DNA solution or in a lyophilised form, and the other container would include the matrix, which may or may not itself be prewetted with a sterile solution.

The kits may also comprise a second or third container means for containing a sterile, pharmaceutically acceptable buffer or other diluent. Such a solution may be required to formulate either the DNA component, the matrix component, both components separately, or a pre-mixed combination of the components, into a more gelatinous form for application to the body. It should be noted, however, that all components of a kit could be supplied in a dry form, which would allow for "wetting" upon contact with body fluids. Thus, the presence of any type of pharmaceutically acceptable buffer is not a requirement for the kits of the invention.

The container means will generally be a container such as a vial, test tube, flask, bottle, syringe or other container means, into which the components of the kit may placed. The matrix and gene components may also be aliquoted into smaller containers, should this be desired. The kits of the present invention may also include a means for containing the individual containers in close confinement for commercial sale, such as, e.g., injection or blow-molded plastic containers into which the desired vials or syringes are retained.

Irrespective of the number of containers, the kits of the invention may also comprise, or be packaged with, an instrument for assisting with the placement of the ultimate matrix-gene composition within the body of an animal. Such an instrument may be a syringe, pipette, forceps, or any such medically approved delivery vehicle.

Type II Collagen as an Osteoconductive/inductive Material

The present invention also provides methods for stimulating bone progenitor cells, as may be applied, in certain circumstances, to promote new bone formation, or to stimulate wound-healing. As such, the bone progenitor cells that are the targets of the invention may also be termed "wound healing bone progenitor cells", although the function of wound healing itself is not required to practice all aspects of the invention.

To stimulate a bone progenitor cell in accordance with these aspects of the invention, generally one would contact a bone progenitor cell with a composition comprising a biologically effective amount of type II collagen. Although preparations of crushed bone and mineralized collagen have been shown to be osteoconductive, this property has not previously been ascribed to type II collagen. The present inventors have found that type II collagen alone is surprisingly effective at promoting new bone formation, it being able to bridge a 5 mm osteotomy gap in only three weeks in all animals tested.

The forms of type II collagen that may be employed in this invention are virtually limitless. For example, type II collagen may be purified from hyaline cartilage, as isolated from diarthrodial joints or growth plates. Purified type II collagen is commercially available and may be purchased from, e.g., Sigma Chemical Company, St. Louis. Any form of recombinant type II collagen may also be employed, as may be obtained from a type II collagen-expressing recombinant host cell, including bacterial, yeast, mammalian, and insect cells. One particular example of a recombinant type II collagen expression system is a yeast cell that includes an expression vector that encodes type II collagen, as disclosed herein in Example VI.

The type II collagen used in the invention may, if desired, be supplemented with additional minerals, such as calcium, e.g., in the form of calcium phosphate. Both native and recombinant type II collagen may be supplemented by admixing, adsorbing, or otherwise associating with, additional minerals in this manner. Such type II collagen preparations are clearly distinguishable from the types of "mineralized collagen" previously described, e.g., in U.S. Pat. No. 5,231,169 that describes the preparation of mineralized total collagen fibrils.

An object of this aspect of the invention is to provide a source of osteoconductive matrix material, that may be reproducibly prepared in a straightforward and cost-effective manner, and that may be employed, with or without an osteotropic gene segment, to stimulate bone progenitor cells. Recombinant type II collagen was surprisingly found to satisfy these criteria. Although clearly not required for effective results, the combination of native or recombinant type II collagen with mineral supplements, such as calcium, is encompassed by this invention.

A biologically effective amount of type II collagen is an amount of type II collagen that functions to stimulate a bone progenitor cell, as described herein. By way of example, one measure of a biologically effective amount is an amount effective to stimulate bone progenitor cells to the extent that new bone formation is evident. In this regard, the inventors have shown that 10 mg of lyophilized collagen functions effectively to close a 5 mm osteotomy gap in three weeks. This information may be used by those of skill in the art to optimize the amount of type II collagen needed for any given situation.

Depending on the individual case, the artisan would, in light of this disclosure, readily be able to calculate an appropriate amount, or dose, of type II collagen for stimulating bone cells and promoting bone growth. Suitable effective amounts of collagen include between about 1 mg and about 100 mgs of lyophilized type II collagen per bone tissue site. Of course, it is likely that there will be variations due to, e.g., individual responses, particular tissue conditions, and the speed with which bone formation is required. While 10 mg were demonstrated to be useful in the illustrative example, the inventors contemplate that 1, 5, 10, 15, 20, 30, 40, 50, 75, 100, 125 mg, and the like, may be usefully employed. Of course any values within these contemplated ranges may be useful in any particular case. Exceptional cases where even greater amounts of type II collagen need to be employed are not excluded from the methods of the invention.

In contacting or applying type II collagen, with or without a DNA segment, to bone progenitor cells located within a bone progenitor tissue site of an animal, bone tissue growth will be stimulated. Thus, bone cavity sites and bone fractures may be filled and repaired.

The use of type II collagen in combination with a nucleic acid segment that encodes a polypeptide or protein that stimulates bone progenitor cells when expressed in said cells is preferred, as described above. Nucleic acid segments that comprise an isolated PTH gene, BMP gene, growth factor gene, growth factor receptor gene, cytokine gene or a chemotactic factor gene are preferred, with PTH, TGF-$\beta$ and BMP genes being most preferred. The genes function subsequent to their transfer into, and expression in, bone progenitor cells of the treated animal, thus promoting bone growth.

Although type II collagen alone is effective, its combined use with an osteotropic gene segment may prove to give synergistic and particularly advantageous effects. Type II collagen, whether native or recombinant, may thus also be formulated into a therapeutic kit with an osteotropic gene segment, in accordance with those kits described herein above. This includes the use of single or multiple container means; any medically approved delivery vehicle, including, but not limited to, syringes, pipettes, forceps, additional diluents, and the like.

BRIEF DESCRIPTION OF THE DRAWINGS

The drawings form part of the present specification and are included to further demonstrate certain aspects of the present invention. The invention may be better understood by reference to one or more of these drawings in combination with the detailed description of specific embodiments presented herein.

FIG. 3. Southern analysis of retroviral integration in the YZ-15 clone. 10 mg of YZ-15 genomic DNA were digested with KpnI (for which there is a unique site in the vector LTR) and analyzed by Southern blotting. A cDNA fragment that coded for prepro-hPTH1–35 was used as a probe. The positive control for the Southern hybridization conditions was a KpnI digest of genomic DNA from Rat-1 cells infected and selected with the recombinant, replication-defective retrovirus PLJ-hPTH1-84 (Wilson et al., 1992). KpnI digests of DNA were also prepared from two negative controls: native Rat-1 cells and Rat-1 cells infected and selected with BAG ("BAG cells", (Wilson et al., 1992), a replication-defective recombinant retrovirus that encodes β-galactosidase, which is an irrelevant marker gene in these studies. Lane assignments were as follows: 1, PLJ-hPTH1-84 cells; 2 BAG cells; 3, YZ-15; 4, native Rat-1 cells. DNA sizes (kb) are shown at the left of the figure. As expected, a fragment of the predicted size (e.g., 4.3 kb) is seen only in lane 1 (the positive control) and in lane 3 (YZ-15 DNA).

FIG. 4A, FIG. 4B, FIG. 4C and FIG. 4D. Northern blot analysis of a transduced Rat-1 clone. Poly-A($^+$)RNA was prepared from the YZ-15 clone and analyzed by Northern blotting as described (Chen et al., 1993). Poly-A($^+$) RNA prepared from PLJ-hPTH1-84 cells, BAG cells, and native Rat-1 cells were used as positive and negative controls. Four probes were applied to a single blot following sequential stripping: hPTH1-34 (FIG. 4A), β-gal (FIG. 4B), Neo, (FIG.4C) and β-actin (FIG. 4D). Lane assignments were as follows: 1, PLJ-hPTH1-84 cells; 2, BAG cells; 3, YZ-15 cells; 4, native Rat-1 cells. As expected, the hPTH1-34 transcript is seen only in lane 1 (positive control) and in lane 3–4; a Neo transcript is seen in lanes 1–3; a β-gal transcript is seen only in lane 2; and β-actin transcripts are seen in lanes 1–4.

FIG. 8A shows an exemplary result, 4 weeks post surgery (Rat #14) using the normal sense hPTH 1-34 construct applied to a 5 mm gap (as described herein, such as in Example X). The arrows point to new bone formed around new bone at pin sites and in gap, as defined by plain film x-ray examination.

FIG. 8B shows an exemplary control (Rat #15) to compare with FIG. 8A in which an antisense construct was applied to a 5 mm gap. There is no evidence of new bone formation 4 weeks post surgery.

FIG. 9. The mouse BMP-4 amino acid sequence, SEQ ID NO:1. The HA epitope is shown in bold at the extreme carboxy terminus of the sequence.

FIG. 10A: note the positive (the bracketed gray region) β-gal cytoplasmic staining of callus tissue cells from the UltraFiber™+adenovirus implant. This result indicates that cel surface receptors that mediate infection, and thus viral transduction, are expressed by (at least one population) callus cells during the fracture healing process. FIG. 10B: serial section negative control stained with the vehicle of the β-gal antibody plus cocktail of non-specific rabbit lgG antibodies. FIG.10C: note the positive (boxed) β-gal nuclear staining of chondrocytes in the osteotomy site filled with UltraFiber™ and AdRSVnt-lacZ. This result demonstrates the exquisite specificity of the anti-β-gal antibody, and conclusively demonstrates expression of the marker gene product in the osteotomy gap.

FIG. 11A shows tendon tissue with the SIS+plasmid graft. Note the positive cytoplasmic staining of fibroblastic cells as shown by the continuous light gray staining, as indicated by the arrows. The bottom panel shows tendon tissue with the SIS-alone graft. Note the virtual absence of specific cytoplasmic staining in this negative control tissue section.

FIG. 13A, FIG. 13B, FIG. 13C, FIG. 13D, FIG. 13E and FIG. 13F consists of autoradiograms made by direct exposure of tissue sections (FIG. 13A and FIG. 13D) to film after hybridization with radiolabeled probes. Day 8.5–9.0 sections contained embryos surrounded by intact membranes, uterine tissues, and the placental disk, cut in random planes. Day 13.5 (FIG. 13B and FIG. 13E) and (FIG. 13C and FIG. 13F) sections contain isolated whole embryos sectioned in the sagittal plane near or about the mid-line. FIG. 13A, FIG. 13B and FIG. 13C were hybridized with an antisense probe; FIG. 13D, FIG. 13E and FIG. 13F were hybridized with a sense probe. Identical conditions were maintained throughout autoradiography and photography, thereby allowing a comparison of the overall strength of hybridization in all tissue sections. The transcript is expressed in connective tissue, mesenchyme, liver, heart and CNS.

DESCRIPTION OF THE PREFERRED EMBODIMENT

Figure 1:
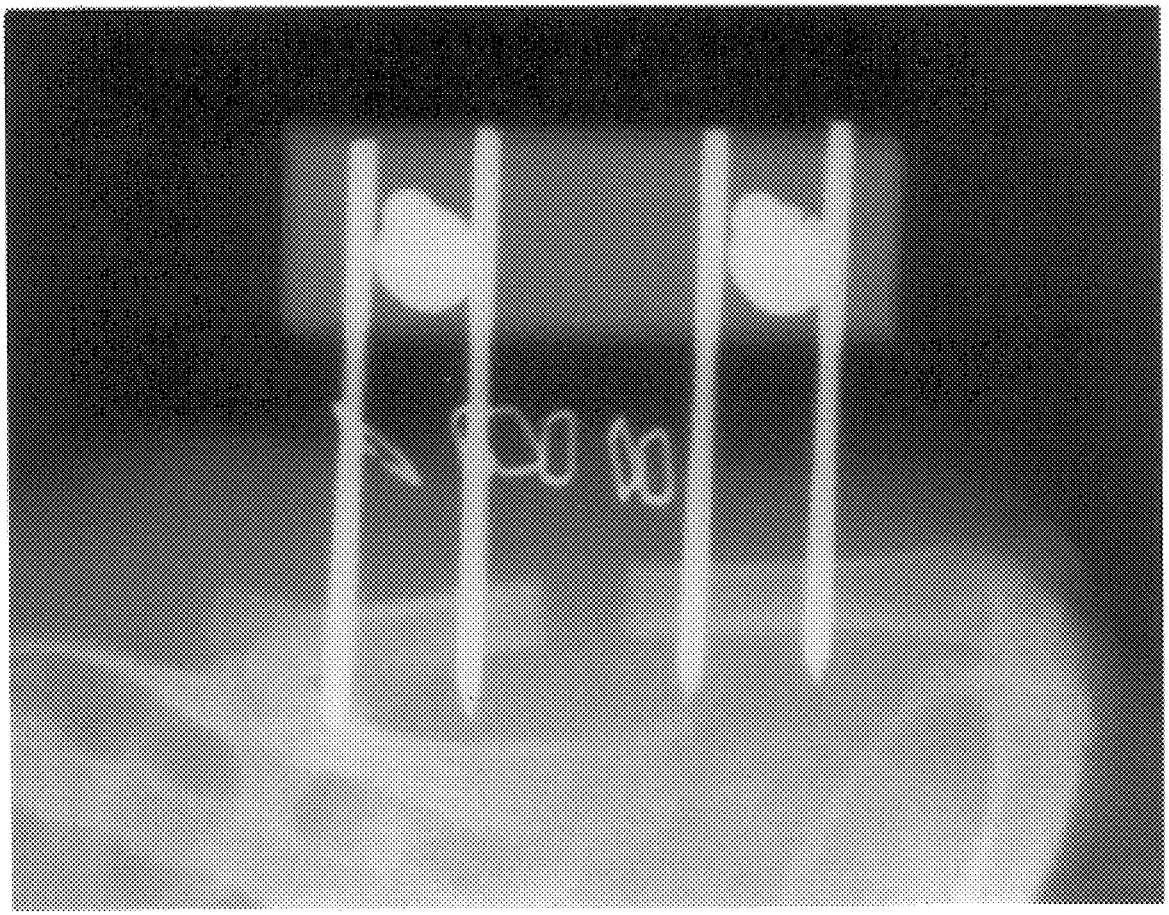
FIG. 1. Rat osteotomy model. The osteotomy site immediately after surgery. As expected, no evidence of mineralized tissue in the osteotomy gap was observed immediately post-op.

1. Applications of Bone Repair Technology to Human Treatment

The following is a brief discussion of four human conditions to exemplify the variety of diseases and disorders that would benefit from the development of new technology to improve bone repair and healing processes. In addition to the following, several other conditions, such as, for example, vitamin D deficiency; wound healing in general; soft skeletal tissue repair; and cartilage and tendon repair and regeneration, may also benefit from technology concerning the stimulation of bone progenitor cells.

The first example is the otherwise healthy individual who suffers a fracture. Often, clinical bone fracture is treated by casting to alleviate pain and allow natural repair mechanisms to repair the wound. There has been progress in the treatment of fracture in recent times, however, even without considering the various complications that may arise in treating fractured bones, any new procedures to increase bone healing in normal circumstances would be represent a great advance.

A second example which may benefit from new treatment methods is osteogenesis imperfecta (OI). OI encompasses various inherited connective tissue diseases that involve bone and soft connective tissue fragility in humans (Byers & Steiner, 1992; Prockop, 1990). About one child per 5,000–14,000 born is affected with OI and the disease is associated with significant morbidity throughout life. A certain number of deaths also occur, resulting from the high propensity for bone fracture and the deformation of abnormal bone after fracture repair (OI types II–IV; Donadio & Goldstein, 1993). The relevant issue here is quality of life; clearly, the lives of affected individuals would be improved by the development of new therapies designed to stimulate and strengthen the fracture repair process.

OI type I is a mild disorder characterized by bone fracture without deformity, blue sclerae, normal or near normal stature, and autosomal dominant inheritance (Bonadio & Goldstein). Osteopenia is associated with an increased rate of lone bone fracture upon ambulation (the fracture frequency decreases dramatically at puberty and during young adult life, but increases once again in late middle age). Hearing loss, which often begins in the second or third decade, is a feature of this disease in about half the families and can progress despite the general decline in fracture frequency. Dentinogenesis imperfecta is observed in a subset of individuals.

In contrast, OI types II–VI represent a spectrum of more severe disorders associated with a shortened life-span. OI type II, the perinatal lethal form, is characterized by short stature, a soft calvarium, blue sclerae, fragile skin, a small chest, floppy appearing lower extremities (due to external rotation and abduction of the femurs), fragile tendons and ligaments, bone fracture with severe deformity, and death in the perinatal period due to respiratory insufficiency. Radiographic signs of bone weakness include compression of the femurs, bowing of the tibiae, broad and beaded ribs, and calvarial thinning.

OI type III is characterized by short stature, a triangular facies, severe scoliosis, and bone fracture with moderate deformity. Scoliosis can lead to emphysema and a shortened life-span due to respiratory insufficiency. OI type IV is characterized by normal sclerae, bone fracture with mild to moderate deformity, tooth defects, and a natural history that essentially is intermediate between OI type II and OI type I.

More than 150 OI mutations have been characterized since 1989 (reviewed in Byers & Steiner, 1992; Prockop, 1990). The vast majority occur in the COL1A1 and COL1A2 genes of type I collagen. Most cases of OI type I appear to result from heterozygous mutations in the COL1A1 gene that decrease collagen production but do not alter primary structure, i.e. heterozygous null mutations affecting COL1A1 expression.

A third, important example is osteoporosis. The term osteoporosis refers to a heterogeneous group of disorders characterized by decreased bone mass and fractures. An estimated 20–25 million people are at increased risk for fracture because of site-specific bone loss. Risk factors for osteoporosis include increasing age, gender (more females), low bone mass, early menopause, race (Caucasians), low calcium intake, reduced physical activity, genetic factors, environmental factors (including cigarette smoking and abuse of alcohol or caffeine), and deficiencies in neuromuscular control that create a propensity to fall.

More than a million fractures in the USA each year can be attributed to osteoporosis, and in 1986 alone the treatment of osteoporosis cost an estimated 7–10 billion health care dollars. Demographic trends (i.e., the gradually increasing age of the US population) suggest that these costs may increase 2–3 fold by the year 2020 if a safe and effective treatment is not found. Clearly, osteoporosis is a significant health care problem.

Clinically, osteoporosis is segregated into type I and type II. Type I osteoporosis occurs predominantly in middle aged women and is associated with estrogen loss at the menopause, while osteoporosis type II is associated with advancing age. Much of the morbidity and mortality associated with osteoporosis results from immobilization of elderly patients following fracture.

Current therapies for osteoporosis patients focus on fracture prevention, not fracture repair. This remains an important consideration because of the literature, which clearly states that significant morbidity and mortality are associated with prolonged bed rest in the elderly, particularly those who have suffered hip fractures. Complications of bed rest include blood clots and pneumonia. These complications are recognized and measures are usually taken to avoid them, but these is hardly the best approach to therapy. thus, the osteoporotic patient population would benefit from new therapies designed to strengthen bone and speed up the fracture repair process, thus getting these people on their feet before the complications arise.

A fourth example is related to bone reconstruction and, specifically, the ability to reconstruct defects in bone tissue that result from traumatic injury; as a consequence of cancer or cancer surgery; as a result of a birth defect, an error in development, or a heritable disorder; or as a result of aging. There is a significant orthopaedic need for more frequent implants, and cranial and facial bone are particular targets for this type of reconstructive need. The availability of new implant materials, e.g., titanium, has permitted the repair of relatively large defects. Titanium implants provide excellent temporary stability across bony defects. However, experience has shown that a lack of viable bone bridging the defect can result in exposure of the appliance, infection, structural instability and, ultimately, failure to repair the defect.

Autologous bone grafts are another possibility, but they have several demonstrated disadvantages in that they must be harvested from a donor site such as iliac crest or rib, they usually provide insufficient bone to completely fill the defect, and the bone that does form is sometimes prone to infection and resorption. Partially purified xenogeneic preparations are not practical for clinical use because microgram quantities are purified from kilograms of bovine bone, making large scale commercial production both costly and impractical. Allografts and demineralized bone preparations are therefore often employed.

Microsurgical transfers of free bone grafts with attached soft tissue and blood vessels can close bony defects with an immediate source of blood supply to the graft. However, these techniques are time consuming, have been shown to produce a great deal of morbidity, and can only be used by specially trained individuals. Furthermore, the bone implant is often limited in quantity and is not readily contoured. In the mandible, for example, the majority of patients cannot wear dental appliances using presently accepted techniques (even after continuity is established), and thus gain little improvement in the ability to masticate. Toriumi et al. have written the "Reconstructive surgeons should have at their disposal a bone substitute that would be reliable, biocompatible, easy to use, and long lasting and that would restore mandibular continuity with little associated morbidity."

In connection with bone reconstruction, specific problem areas for improvement are those concerned with treating large defects, such as created by trauma, birth defects, or particularly, following tumor resection; and also the area of artificial joints. The success of orthopaedic implants, interfaces and artificial joints could conceivably be improved if the surface of the implant, or a functional part of an implant, were to be coated with a bone stimulatory agent. The surface of implants could be coated with one or more appropriate materials in order to promote a more effective interaction with the biological site surrounding the implant and, ideally, to promote tissue repair.

2. Bone Repair

Bone tissue is known to have the capacity for repair and regeneration and there is a certain understanding of the cellular and molecular basis of these processes. The initiation of new bone formation involves the commitment, clonal expansion, and differentiation of progenitor cells. Once initiated, bone formation is promoted by a variety of polypeptide growth factors, Newly formed bone is then maintained by a series of local and systemic growth and differentiation factors.

The concept of specific bone growth-promoting agents is derived from the work of Huggins and Urist. Huggins et al. demonstrated that autologous transplantation of canine incisor tooth to skeletal muscle resulted in local new bone formation (Huggins et al., 1936). Urist and colleagues reported that demineralized lyophilized bone segments induced bone formation (Urist, 1965; Urist et al., 1983), a process that involved macrophage chemotaxis; the recruitment of progenitor cells; the formation of granulation tissue, cartilage, and bone; bone remodeling; and marrow differentiation. The initiation of cartilage and bone formation in an extraskeletal site, a process referred to as osteoinduction, has permitted the unequivocal identification of initiators of bone morphogenesis (Urist, 1965; Urist et al., 1983; Sampath et al., 1984; Wang et al., 1990; Cunningham et al., 1992).

Significant progress has now been made in characterizing the biological agents elaborated by active bone tissue during growth and natural bone healing. Demineralized bone matrix is highly insoluble; Sampath and Reddi (1981) showed that only 3% of the proteins can be extracted using strong combinations of denaturants and detergents. They also showed that the unfractionated demineralized bone extract will initiate bone morphogenesis, a critical observation that led to the purification of "osteoinductive" molecules. Families of proteinaceous osteoinductive factors have now been purified and characterized. They have been variously referred to in the literature as bone morphogenetic or morphogenic proteins (BMPs), osteogenic bone inductive proteins or osteogenic proteins (OPs).

3. Bone Repair and Bone Morphogenetic Proteins (BMPs)

Following their initial purification, several bone morphogenetic protein genes have now been cloned using molecular techniques (Wozney et al., 1988; Rosen et al., 1989; summarized in Alper, 1994). This work has established BMPs as members of the transforming growth factor-$\beta$ (TGF-$\beta$) superfamily based on DNA sequence homologies. Other TGF molecules have also been shown to participate in new bone formation, and TGF-$\beta$ is regarded as a complex multifunctional regulator of osteoblast function (Centrella et al., 1988; Carrington et al., 1969–175; Seitz et al., 1992). Indeed, the family of transforming growth factors (TGF-$\alpha$ and TGF-$\beta$) has been proposed as potentially useful in the treatment of bone disease (U.S. Pat. No. 5,125,978, incorporated herein by reference).

The cloning of distinct EMP genes has led to the designation of individual BMP genes and proteins as BMP-1 through BMP-8. BMPs 2–8 are generally thought to be osteogenic (BMP-1 may be a more generalized morphogen; Shimell et al., 1991). BMP-3 is also called osteogenin (Luyten et al., 1989) and BMP-7 is also called OP-1 (Ozkaynak et al., 1990). TGFs and BMPs each act on cells via complex, tissue-specific interactions with families of cell surface receptors (Roberts & Sporn, 1989; Paralkar et al., 1991).

Several BMP (or OP) nucleotide sequences and vectors, cultured host cells and polypeptides have been described in the patent literature. For example, U.S. Pat. Nos., e.g., 4,877,864, 4,968,590 and 5,108,753 all concern osteogenic factors. More specifically, BMP-1 is disclosed in U.S. Pat. No. 5,108,922; BMP-2 species, including BMP-2A and BMP-2B, are disclosed in U.S. Pat. Nos. 5,166,058, 5,013, 649, and 5,013,649; BMP-3 in 5,116,738; BMP-5 in 5,106, 748; BMP-6 in 5,187,076; and BMP-7 in 5,108,753 and 5,141,905; all incorporated herein by reference. Various BMP clones and their activities are particularly described by Wozney et al. (1988; incorporated herein by reference). DNA sequences encoding the osteogenic proteins designated OP-1, COP-5 and COP-7 are also disclosed in U.S. Pat. No. 5,011,691. Although the BMP terminology is widely used, it may prove to be the case that there is an OP counterpart term for every individual BMP (Alper, 1994).

4. Bone Repair and Growth Factors and Cytokines

Transforming growth factors (TGFs) have a central role in regulating tissue healing by affecting cell proliferation, gene expression, and matrix protein synthesis (Roberts & Sporn, 1989). While not a direct effect, Bolander and colleagues have provided evidence that TGF-β1 and TGF-β2 can initiate both chondrogenesis and osteogenesis (Joyce et al., 1990; Izumi et al., 1992; Jingushi et al., 1992). In these studies new cartilage and bone formation appeared to be dose dependent (i.e. dependent on the local growth factor concentration). The data also suggested that TGF-β1 and TGF-β2 stimulated cell differentiation by a similar mechanism, even though they differed in terms of the ultimate amount of new cartilage and bone that was formed.

Other growth factors/hormones besides TGF and BMP may influence new bone formation following fracture. Bolander and colleagues injected recombinant acidic fibroblast growth factor into a rat fracture site (Jingushi et al., 1990). The major effect of multiple high doses (1.0 mg/50 ml) was a significant increase in cartilage tissue in the fracture gap, while lower doses had no effect. These investigators also used the reverse transcriptase-polymerase chain reaction (PCR) technique to demonstrate expression of estrogen receptor transcripts in callus tissue (Boden et al., 1989). These results suggested a role for estrogen in normal fracture repair.

Horowitz and colleagues have shown that activated osteoblasts will synthesize the cytokine, macrophage colony stimulating factor (Horowitz et al., 1989). The osteotropic agents used in this study included lipopolysaccharide, PTH1-84, PTH1-34, vitamin D and all-trans retinoic acid. This observation has led to the suggestion that osteoblast activation following fracture may lead to the production of cytokines that regulate both hematopoiesis and new bone formation. Various other proteins and polypeptides that have been found to be expressed at high levels in osteogenic cells, such as, e.g., the polypeptide designated Vgr-1 (Lyons et al. 1989), also have potential for use in connection with the present invention.

5. Bone Repair and Calcium Regulating Hormones

Calcium regulating hormones such as parathyroid hormone (PTH) participate in new bone formation and bone remodeling (Raisz & Kream, 1983). PTH is an 84 amino acid calcium-regulating hormone whose principle function is to raise the $Ca^{+2}$ concentration in plasma and extracellular fluid. Studies with the native hormone and with synthetic peptides have demonstrated that the amino-terminus of the molecule (aa 1-34) contains the structural requirements for biological activity (Tregear et al., 1973; Hermann-Erlee et al., 1976; Riond, 1993). PTH functions by binding to a specific cell surface receptor that belongs to the G protein-coupled receptor superfamily (Silve et al., 1982; Rizzoli et al., 1983; Juppner et al., 1991).

Using a retroviral approach, a human full-length PTH gene construct has been introduced into cultured rat fibroblasts to create recombinant PTH-secreting cells. These cells were then transplanted into syngeneic rat recipients that were observed to develop hypercalcemia mediated by the increased serum concentrations of PTH (Wilson et al., 1992). The object of these studies was to create an animal model of primary hyperparathyroidism.

PTH has a dual effect on new bone formation, a somewhat confusing aspect of hormone function despite intensive investigation. PTH has been shown to be a potent direct inhibitor of type I collagen production by osteoblasts (Kream et al., 1993). Intact PTH was also shown to stimulate bone resorption in organ culture over 30 years ago, and the hormone is known to increase the number and activity of osteoclasts. Recent studies by Gay and colleagues have demonstrated binding of $[^{125}I]PTH(1-84)$ to osteoclasts in tissue sections and that osteoclasts bind intact PTH in a manner that is both saturable and time- and temperature dependent (Agarwala & Gay, 1992). While these properties are consistent with the presence of PTH/PTHrP receptors on the osteoclast cell surface, this hypothesis is still considered controversial. A more accepted view, perhaps, is that osteoclast activation occurs via an osteoblast signaling mechanism.

On the other hand, osteosclerosis may occur in human patients with primary hyperparathyroidism (Seyle, 1932). It is well known that individuals with hyperparathyroidism do not inexorably lose bone mass, but eventually achieve a new bone remodeling steady state after an initial period of net bone loss. Chronic, low dose administration of the amino-terminal fragment of PTH (aa 1-34) also can induce new bone formation according to a time- and dose-dependent schedule (Seyle, 1932; Parsons & Reit, 1974).

Human PTH1-34 has recently been shown to: stimulate DNA synthesis in chick osteoblasts and chondrocytes in culture (van der Plas, 1985; Schluter et al., 1989; Somjen et al., 1990); increase bone cell number in vivo (Malluche et al., 1986); enhance the in vitro growth of chick embryonic cartilage and bone (Kawashima, 1980; Burch & Lebovitz, 1983; Lewinson & Silbermann, 1986; Endo et al., 1980; Klein-Nulend et al., 1990); enhance surface bone formation (both cortical and trabecular bone) in normal and osteogenic animals and in humans with osteoporosis (Reeve et al., 1976; Reeve et al., 1980; Tam et al., 1982; Hefti et al., 1982; Podbesek et al., 1983; Stevenson & Parsons, 1983; Slovik et al., 1986; Gunness-Hey & Hock, 1984; Tada et al., 1988; Spencer et al., 1989; Hock & Fonseca, 1990; Liu & Kalu, 1990; Hock & Gera, 1992; Mitlak et al., 1992; Ejersted et al., 1993); and delay and reverse the catabolic effects of estrogen deprivation on bone mass (Hock et al., 1988; Hori et al., 1988; Gunness-Hey & Hock, 1989) Liu et al., 1991). Evidence of synergistic interactions between hPTH-1-34 and other anabolic molecules has been presented, including insulin-like growth factor, BMP-2, growth hormone, vitamin D, and TGF-β (Slovik et al., 1986; Spencer et al., 1989; Mitlak et al., 1992; Canalis et al., 1989; Linkhart & Mohan, 1989; Seitz et al., 1992; Vukicevic et al., 1989).

Anecdotal observation has shown that serum PTH levels may be elevated following bone fracture (Meller et al., 1984; Johnston et al., 1985; Compston et al., 1989; Hardy et al., 1993), but the significance of this observation is not understood. There are apparently no reports in the literature concerning attempts to localize either PTH or the PTH/PTHrP receptor in situ in human fracture sites or in experimental models. Furthermore, no attempt has been made to augment bone repair by the exogenous addition of PTH peptides. Although hPTH1-34 has known to function as an anabolic agent for bone, prior to the present invention, much remained to be learned about the role (if any) of PTH during bone regeneration and repair.

6. Protein Administration and Bone Repair

Several studies have been conducted in which preparations of protein growth factors, including BMPs, have been administered to animals in an effort to stimulate bone growth. The results of four such exemplary studies are described blow.

Toriumi et al. studied the effect of recombinant BMP-2 on the repair of surgically created defects in the mandible of adult dogs (Toriumi et al., 1991). Twenty-six adult hounds were segregated into three groups following the creation of a 3 cm full thickness mandibular defect: 12 animals received test implants composed of inactive dog bone matrix carrier and human BMP-2, 10 animals received control implants composed of carrier without BMP-2, and BMP-4 animals received no implant. The dogs were euthanized at 2.5–6 months, and the reconstructed segments were analyzed by radiography, histology, histomorphometry, and biomechanical testing. Animals that received test implants were euthanized after 2.5 months because of the presence of well mineralized bone bridging the defect. The new bone allowed these animals to chew a solid diet, and the average bending strength of reconstructed mandibles was 27% of normal ('normal' in this case represents the unoperated, contralateral hemimandible). In contrast, the implants in the other two groups were non-functional even after 6 months and showed minimal bone formation.

Yasko et al. published a related study in which the effect of BMP-2 on the repair of segmental defects in the rat femur was examined (Yasko et al., 1992). The study design included a group that received a dose of 1.4 mg of BMP-2, another group that received 11.0 mg of BMP-2, and a control group that received carrier matrix alone. Endochondral bone formation was observed in both groups of animals that received BMP-2. As demonstrated by radiography, histology, and whole bone (torsion) tests of mechanical integrity, the larger dose resulted in functional repair of the 5 mm defect beginning 4.5 weeks after surgery. The lower dose resulted in radiographic and histological evidence of new bone formation, but functional union was not observed even after 9 weeks post surgery. There was also no evidence of bone formation in control animals at this time.

Chen et al. showed that a single application of 25–100 mg of recombinant TGF-β1 adjacent to cartilage induced endochondral bone formation in the rabbit ear full thickness skin wounds (Chen et al., 1991). Bone formation began 21 days following the creation of the wound and reached a peak at day 42, as demonstrated by morphological methods. Active bone remodeling was observed beyond this point.

In a related study, Beck et al. demonstrated that a single application of TGF-β1 in a 3% methylcellulose gel was able to repair surgically induced large skull defects that otherwise heal by fibrous connective tissue and never form bone (Beck et al., 1991). Bony closure was achieved within 28 days of the application of 200 mg of TGF-β1 and the rate of healing was shown to be dose dependent.

Studies such as those described above have thus established that exogenous growth factors can be used to stimulate new bone formation/repair/regeneration in vivo. Certain U.S. Patents also concern methods for treating bone defects or inducing bone formation. For example, U.S. Pat. No. 4,877,864 relates to the administration of a therapeutic composition of bone inductive protein to treat cartilage and/or bone defects; U.S. Pat. No. 5,108,753 concerns the use of a device containing a pure osteogenic protein to induce endochondral bone formation and for use in periodontal, dental or craniofacial reconstructive procedures.

However, nowhere in this extensive literature does there appear to be any suggestion that osteogenic genes themselves may be applied to an animal in order to promote bone repair or regeneration. Indeed, even throughout the patent literature that concerns genes encoding various bone stimulatory factors and their in vitro expression in host cells to produce recombinant proteins, there seems to be no mention of the possibility of using nucleic acid transfer in an effort to express an osteogenic gene in bone progenitor cells in vivo or to promote new bone formation in an animal or human subject.

7. Biocompatible Matrices for use in Bone Repair

There is a considerable amount of work that has been directed to the development of biocompatible matrices for use in medical implants, including those specifically for bone implantation work. In context of the present invention, a matrix may be employed in association with the gene or DNA coding region encoding the osteotropic polypeptide in order to easily deliver the gene to the site of bone damage. The matrix is thus a "biofiller" that provides a structure for the developing bone and cartilage. Such matrices may be formed from a variety of materials presently in use for implanted medical applications.

Matrices that may be used in certain embodiments include non-biodegradable and chemically defined matrices, such as sintered hydroxyapatite, bioglass, aluminates, and other ceramics. The bioceramics may be altered in composition, such as in calcium-aluminate-phosphate; and they may be processed to modify particular physical and chemical characteristics, such as pore size, particle size, particle shape, and biodegradability. Certain polymeric matrices may also be employed if desired, these include acrylic ester polymers and lactic acid polymers, as disclosed in U.S. Pat. Nos. 4,526,909, and 4,563,489, respectively, each incorporated herein by reference. Particular examples of useful polymers are those of orthoesters, anhydrides, propylene-cofumarates, or a polymer of one or more α-hydroxy carboxylic acid monomers, (e.g. α-hydroxy acetic acid (glycolic acid) and/or α-hydroxy propionic acid (lactic acid).

Optimally, the best matrices for present purposes are those that are capable of being resorbed into the body. Potential biodegradable matrices for use in bone gene transfer include, for example, biodegradable and chemically defined calcium sulfate, tricalciumphosphate, hydroxyapatite, polylactic acid and polyanhydrides. Furthermore, biomatrices comprised of pure proteins and/or extracellular matrix components may be employed.

The inventors currently prefer to use bone or dermal collagenous materials as matrices, as may be prepared from various commercially-available lyophilized collagen preparations, such as those from bovine or rat skin. Collagen matrices may also be formulated as described in U.S. Pat. No. 4,394,370, incorporated herein by reference, which concerns the use of collagenous matrices as delivery vehicles for osteogenic protein. UltraFiber™, as may be obtained from Norian Corp. (Mountain View, Calif.), is a preferred matrix. Preferred matrices are those formulated with type II collagen, and most preferably, recombinant type II collagen and mineralized type II collagen.

Further suitable matrices may also be prepared from combinations of materials, such as polylactic acid and hydroxyapatite or collagen and tricalciumphosphate. Although sufficient sequestration and subsequent delivery of an osteotropic gene is in no way a limitation of the present invention, should it be desired, a porous matrix and gene combination may also be administered to the bone tissue site in combination with an autologous blood clot. The basis for this is that blood clots have previously been employed to increase sequestration of osteogenic proteins for use in bone treatment (U.S. Pat. No. 5,171,579, incorporated herein by reference) and their use in connection with the present invention is by no means excluded (they may even attract growth factors for cytokines).

8. Collagen

Although not previously proposed for use with a nucleic acid molecule, the use of collagen as a pharmaceutical delivery vehicle has been described. The biocompatibility of collagen matrices is well known in the art. U.S. Pat. Nos. 5,206,028, 5,128,136, 5,081,106, 4,585,797, 4,390,519, and 5,197,977 (all incorporated herein by reference) describe the biocompatibility of collagen-containing matrices in the treatment of skin lesions, use as a wound dressing, and as a means of controlling bleeding. In light of these documents, therefore, there is no question concerning the suitability of applying a collagen preparation to a tissue site of an animal.

U.S. Pat. No. 5,197,977 describes the preparation of a collagen-impregnated vascular graft including drug materials complexed with the collagen to be released slowly from the graft following implant. U.S. Pat. No. 4,538,603 is directed to an occlusive dressing useful for treating skin lesions and a granular material capable of interacting with wound exudate. U.S. Pat. No. 5,162,430 describes a pharmaceutically acceptable, non-immunogenic composition comprising atelopeptide collagen chemically conjugated to a synthetic hydrophilic polymer.

Further documents that one of skill in the art may find useful include U.S. Pat. Nos. 4,837,285, 4,703,108, 4,409,332, and 4,347,234, each incorporated herein by reference. These references describe the uses of collagen as a non-immunogenic, biodegradable, and bioresorbable binding agent.

The inventors contemplate that collagen from many sources will be useful in the present invention. Particularly useful are the amino acid sequences of type II collagen. Examples of type II collagen are well known in the art. For example, the amino acid sequences of human (Lee et al., 1989), rat (Michaelson et al., 1994), and mouse (Ortman et al., 1994) have been determined (SEQ ID NO:10, SEQ ID NO:12, and SEQ ID NO:14, respectively).

Although not previously known to be capable of stimulating bone progenitor cells itself, type II collagen is herein surprisingly shown to possess this property, which thus gives rise to new possibilities for clinical use.

9. Nucleic Acid Delivery

The transfer of nucleic acids to mammalian cells has been proposed a method for treating certain diseases or disorders. Nucleic acid transfer or delivery is often referred to as "gene therapy". Initial efforts toward postnatal (somatic) gene therapy relied on indirect means of introducing genes into tissues, e.g., target cells were removed from the body, infected with viral vectors carrying recombinant genes, and implanted into the body. These type of techniques are generally referred to as ex vivo treatment protocols. Direct in vivo gene transfer has recently been achieved with formulations of DNA trapped in liposomes (Ledley et al., 1987); or in proteoliposomes that contain viral envelope receptor proteins (Nicolau et al., 1983); calcium phosphate-coprecipitated DNA (Benvenisty & Reshef, 1986); and DNA coupled to a polylysine-glycoprotein carrier complex (Wu & Wu, 1988). The use of recombinant replication-defective viral vectors to infect target cells in vivo has also been described (e.g., Seeger et al., 1984).

In recent years, Wolff et al. demonstrated that direct injection of purified preparations of DNA and RNA into mouse skeletal muscle resulted in significant reporter gene expression (Wolfe et al., 1990). This was an unexpected finding, and the mechanism of gene transfer could not be defined. The authors speculated that muscle cells may be particularly suited to take up and express polynucleotides in vivo or that damage associated with DNA injection may allow transfection to occur.

Wolff et al. suggested several potential applications of the direct injection method, including (a) the treatment of heritable disorders of muscle, (b) the modification of non-muscle disorders through muscle tissue expression of therapeutic transgenes, (c) vaccine development, and (d) a reversible type of gene transfer, in which DNA is administered much like a conventional pharmaceutical treatment. In an elegant study Liu and coworkers recently showed that the direct injection method can be successfully applied to the problem of influenza vaccine development (Ulmer et al., 1993).

The use of gene transfer to synoviocytes as a means of treating arthritis has also been discussed (Bandara et al., 1992; Roessler et al., 1993). The protocols considered have included both the ex vivo treatment of isolated synoviocytes and their re-introduction into the animal and also direct gene transfer in which suitable vectors are injected into the joint. The transfer of marker genes into synoviocytes has already been demonstrated using both retroviral and adenoviral technology (Bandara et al., 1992; Roessler et al., 1993).

Despite the exclusive emphasis on protein treatment by those working in this field, the present inventors saw that there was great potential for using nucleic acids themselves to promote bone regeneration/repair in vivo. In addition to the ease and cost, it was reasoned that using DNA transfer rather than peptide transfer would provide many further advantages. For example, DNA transfer allows for the expression or over-expression of integral membrane receptors on the surface of bone regeneration/repair cells, whereas this cannot be done using peptide transfer because the latter (a priori) is an extracellular manipulation. Importantly, DNA transfer also allows for the expression of polypeptides modified in a site-directed fashion with the very minimum of additional work (i.e., straightforward molecular biological manipulation without protein purification).

The inventors contemplated that both naked DNA and viral-mediate DNA could be employed in an effort to transfer genes to bone progenitor cells. In beginning to study this, the most appropriate animal model had to be employed, that is, one in which the possibilities of using nucleic acids to promote bone repair could be adequately tested in controlled studies.

10. Osteotomy Model

Prior to the present invention, three model systems were available for study in this area, including Mov13 mice, an animal model of OI. Unfortunately, each of the models suffers from significant drawbacks. With the Mov13 mice, first, these mice typically die in young adulthood because of retrovirus-induced leukemia (Schnieke et al., 1983); second, gene transfer studies in Mov13 mice conducted between postnatal weeks 8–16 (i.e. prior to the development of leukemia) may be complicated by a natural adaptation in which a significant amount of new bone is deposited on the periosteal surface (Bonadio et al., 1993); and third, an osteotropic gene transferred into an osteotomy site may synergize with the active retrovirus and make it even more virulent.

Another system is the in vivo bone fracture model created by Einhorn and colleagues (Bonnarens & Einhorn, 1984). However, this model is a closed system that would not easily permit gene transfer in vivo. The organ culture model developed by Bolander and colleagues (Joyce et al., 1991) was also available, but again, this model is not suitable for studying gene transfer in vivo. Due to the unsuitability of the above models for studying the effects of gene transfer on bone repair and regeneration, the inventors employed a rat osteotomy system, as described below.

The important features of the rat osteotomy model are as follows: Under general anesthesia, four 1.2 mm diameter pins are screwed into the femoral diaphysis of normal adult Sprague-Dawley rats. A surgical template ensures parallel placement of the pins. An external fixator is then secured on the pins, and a 2 mm, or 5 mm, segmental defect is created in the central diaphysis with a Hall micro 100 oscillating saw. A biodegradable implant material, soaked in a solution of plasmid DNA, other genetic construct or recombinant virus preparation, is then placed in the intramedullary canal and the defect is closed (FIG. 1).

New bone formation can be detected as early as three weeks later in the 2 mm gap, although up to 9 weeks is generally allowed for new bone formation to occur. The fixator provided the necessary stability, and there were no limitations on animal ambulation. The surgical protocol has been successfully performed on 21/21 animals to date. None of these animals have died. Assays of new bone formation are performed after sacrifice, except plain film radiography, which is performed weekly from the time of surgery to sacrifice.

Previous studies in Sprague-Dawley rats have shown that the 5 mm osteotomy gap will heal as a fibrous non-union, whereas a gap of less than 3 mm, (such as the 2 mm gap routinely employed in the studies described herein) will heal by primary bone formation. Studies using the 5 mmgap thus allow a determination of whether transgene expression can stimulate new bone formation when fibrous tissue healing normally is expected. On the other hand, studies with the 2 mm gap allow a determination of whether transgene expression can speed up natural primary bone healing.

11. Gene Transfer Promotes Bone Repair In Vivo

The present inventors surprisingly found that gene transfer into bone progenitor cells in vivo (i.e., cells in the regenerating tissue in the osteotomy gap) could be readily achieved. Currently, the preferred methods for achieving gene transfer generally involve using a fibrous collagen implant material soaked in a solution of DNA shortly before being placed in the site in which one desires to promote bone growth. As the studies presented herein show, the implant material facilitates the uptake of exogenous plasmid constructs by cells (in the osteotomy gap) which clearly participate in bone regeneration/repair. The transgenes, following cellular uptake, direct the expression of recombinant polypeptides, as evidenced by the in vivo expression of functional marker gene products.

Further studies are presented herein demonstrating that the transfer of an osteotropic gene results in cellular expression of a recombinant osteotropic molecule, which expression is directly associated with stimulation of new bone formation. After considering a relatively large number of candidate genes, a gene transfer vector coding for a fragment of human parathyroid hormone (hPTH1-34) was chosen for the inventors' initial studies. Several factors were considered in making this choice: (a), recombinant hPTH1-34 peptides can be discriminated from any endogenous rat hormone present in osteotomy tissues; (b), hPTH1-34 peptides will stimulate new bone formation in Sprague-Dawley rats, indicating that the human peptide can efficiently bind the PTH/PTHrP receptor on the rat osteoblast cell surface; and (c), there is only one PTH/PTHrP receptor, the gene for this receptor has been cloned, and cDNA probes to the receptor are available.

Thus, in terms of understanding the mechanism of action of the transgene on new bone formation in vivo, the inventors reasoned it most straightforward to correlate the expression of recombinant hPTH1-34 peptide and its receptor with new bone formation in the rat osteotomy model. Of course, following these initial studies, it is contemplated that any one of a wide variety of genes may be employed in connection with the bone gene transfer embodiments of the present invention.

Previous studies have indicated that hPTH1-34 is a more powerful anabolic agent when given intermittently as opposed to continuously. Despite the fact that an anabolic effect would still be expected with continuous dosing, as documented by the studies of Parsons and co-workers (Tam et al., 1982) and Spencer et al. (1989), there was a concern that the PLJ-hPTH1-34 transgene may not function very effectively as transfected cells would be expected to express recombinant hPTH1-34 molecules in a constitutive manner. The finding that transfection and expression of the LPH-hPTH1-34 transgene did effectively stimulate bone formation in the rat osteotomy model was therefore an important result.

As the osteotomy site in this model is highly vascularized, one possible complication of the studies with the PLJ-hPTH1-34 transgene is the secretion of recombinant human PTH from the osteotomy site with consequent hypercalcemia and (potentially) animal death. Weekly serum calcium levels should therefore be determined when using this transgene. the fact that no evidence of disturbed serum calcium levels has been found in this work is therefore a further encouraging finding.

These studies complement others by the inventors in which direct gene transfer was employed to introduce genes into Achilles' tendon and cruciate ligament, as described in Example XI.

Various immediate applications for using nucleic acid delivery in connection with bone disorders became apparent to the inventors following these surprising findings. The direct transfer of an osteotropic gene to promote fracture repair in clinical orthopaedic practice is just one use. Other important aspects of this technology include the use of gene transfer to treat patients with "weak bones", such as in diseases like osteoporosis; to improve poor healing which may arise fro unknown reasons, e.g., fibrous non-union; to promote implant integration and the function of artificial joints; to stimulate healing of other skeletal tissues such as Achilles' tendon; and as an adjuvant to repair large defects. In all such embodiments, DNA is being used as a direct pharmaceutical agent.

The use of the methods and compositions of the present invention in stimulating vascular graft survival is also contemplated. The invention may thus be employed in connection with the technology described by Sandusky et al. (1992; incorporate herein by reference). In this case, the matrix part of the composition would be the biological graft, preferably made from acellular collagen, and more preferably type II collagen, and most preferably recombinant type II collagen, such as a small intestine submucosa (SIS) graft. To practice these aspects of the invention one would simply impregnate the biological graft with the nucleic acid that one desired to transfer to the tissue surrounding the graft site.

12. Biological Functional Equivalents

As mentioned above, modification and changes may be made in the structure of an osteotropic gene and still obtain a functional molecule that encodes a protein or polypeptide with desirable characteristics. The following is a discussion based upon changing the amino acids of a protein to create an equivalent, or even an improved, second-generation molecule. The amino acid changes may be achieved by change the codons of the DNA sequence, according to the following codon table:

TABLE 1

| Amino Acids   |     |   | Codons |     |     |     |     |     |
|---------------|-----|---|--------|-----|-----|-----|-----|-----|
| Alanine       | Ala | A | GCA    | GCC | GCG | GCU |     |     |
| Cysteine      | Cys | C | UGC    | UGU |     |     |     |     |
| Aspartic acid | Asp | D | GAC    | GAU |     |     |     |     |
| Glutamic acid | Glu | E | GAA    | GAG |     |     |     |     |
| Phenylalanine | Phe | F | UUC    | UUU |     |     |     |     |
| Glycine       | Gly | G | GGA    | GGC | GGG | GGU |     |     |
| Histidine     | His | H | CAC    | CAU |     |     |     |     |
| Isoleucine    | Ile | I | AUA    | AUC | AUU |     |     |     |
| Lysine        | Lys | K | AAA    | AAG |     |     |     |     |
| Leucine       | Leu | L | UUA    | UUG | CUA | CUC | CUG | CUU |
| Methionine    | Met | M | AUG    |     |     |     |     |     |
| Asparagine    | Asn | N | AAC    | AAU |     |     |     |     |
| Proline       | Pro | P | CCA    | CCC | CCG | CCU |     |     |
| Glutamine     | Gln | Q | CAA    | CAG |     |     |     |     |
| Arginine      | Arg | R | AGA    | AGG | CGA | CGC | CGG | CGU |
| Serine        | Ser | S | AGC    | AGU | UCA | UCC | UCG | UCU |
| Threonine     | Thr | T | ACA    | ACC | ACG | ACU |     |     |
| Valine        | Val | V | GUA    | GUC | GUG | GUU |     |     |
| Tryptophan    | Trp | W | UGG    |     |     |     |     |     |
| Tyrosine      | Tyr | Y | UAC    | UAU |     |     |     |     |

For example, certain amino acids may be substituted for other amino acids in a protein structure without appreciable loss of interactive binding capacity with structures such as, for example, antigen-binding regions of antibodies or binding sites on substrate molecules. Since it is the interactive capacity and nature of a protein that defines that protein's biological functional activity, certain amino acid sequence substitutions can be made in a protein sequence, and, of course, its underlying DNA coding sequence, and nevertheless obtain a protein with like properties. It is thus contemplated by the inventors that various changes may be made in the DNA sequences of osteotropic genes without appreciable loss of their biological utility or activity.

In making such changes, the hydropathic index of amino acids may be considered. The importance of the hydropathic amino acid index in conferring interactive biologic function on a protein is generally understood in the art (Kyte & Doolittle, 1982, incorporate herein by reference). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

Each amino acid has been assigned a hydropathic index on the basis of their hydrophobicity and charge characteristics (Kyte & Doolittle, 1982), these are: Isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is known in the art that certain amino acids may be substituted by other amino acids having a similar hydropathic index or score and still result in a protein with similar biological activity, i.e., still obtain a biological functionally equivalent protein. In making such changes, the substitution of amino acids whose hydropathic indices are within ±2 is preferred, those which are within ±1 are particularly preferred, and those within ±0.5 are even more particularly preferred.

It is also understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with a biological property of the protein.

As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine *−0.5); cysteine (−1.0); methionine (−1.3); valine (−1.5); leucine (−1.8); isoleucine (−1.8); tyrosine (−2.3); phenylalanine (−2.5); tryptophan (−3.4).

It is understood that an amino acid can be substituted for another having a similar hydrophilicity value and still obtain a biologically equivalent, and in particular, an immunologically equivalent protein. In such changes, the substitution of amino acids whose hydrophilicity values are within ±2 is preferred, those which are within ±1 are particularly preferred, and those within ±0.5 are even more particularly preferred.

As outline above, amino acid substitutions are generally therefore based on the relative similarity of the amino acid side-chain substituents, for example, their hydrophobicity, hydrophilicity, charge, size, and the like. Exemplary substitutions which take various of the foregoing characteristics into consideration are well known to those of skill in the art and include: arginine and lysine; glutamate and aspartate; serine and threonine; glutamine and asparagine; and valine, leucine and isoleucine.

13. Site-Specific Mutagenesis

Site-specific mutagenesis is a technique useful in the preparation of individual peptides, or biologically functional equivalent proteins or peptides, through specific mutagenesis of the underlying DNA. The technique further provides a ready ability to prepare and test sequence variants, for example, incorporating one or more of the foregoing considerations, by introducing one or more nucleotide sequence changes into the DNA. Site-specific mutagenesis allows the production of mutants through the use of specific oligonucleotide sequences which encode the DNA sequence of the desired mutation, as well as a sufficient number of adjacent nucleotides, to provide a primer sequence of sufficient size and sequence complexity to form a stable duplex on both sides of the deletion junction being traversed. Typically, a primer of about 17 to 25 nucleotides in length is preferred, with about 5 to 10 residues on both sides of the junction of the sequence being altered.

In general, the technique of site-specific mutagenesis is well known in the art, as exemplified by various publications. As will be appreciated, the technique typically employs a phage vector which exists in both a single stranded and double stranded form. Typical vectors useful in site-directed mutagenesis include vectors such as the M13 phage. These phage are readily commercially available and their use is generally well known to those skilled in the art. Double stranded plasmids are also routinely employed in site directed mutagenesis which eliminates the step of transferring the gene of interest from a plasmid to a phage.

In general, site-directed mutagenesis in accordance herewith is performed by first obtaining a single-stranded vector or melting apart of two strands of a double stranded vector which includes within its sequence a DNA sequence which encodes the desired osteotropic protein. An oligonucleotide primer bearing the desired mutated sequence is prepared, generally synthetically. This primer is then annealed with the single-stranded vector, and subjected to DNA polymerizing enzymes such as E. coli polymerase I Klenow fragment, in order to complete the synthesis of the mutation-bearing strand. Thus, a heteroduplex is formed wherein one strand encodes the original non-mutated sequence and the second strand bears the desired mutation. This heteroduplex vector is then used to transform appropriate cells, such as E. coli cells, and clones are selected which include recombinant vectors bearing the mutated sequence arrangement.

The preparation of sequence variants of the selected osteotropic gene using site-directed mutagenesis is provided as a means of producing potentially useful species and is not meant to be limiting as there are other ways in which sequence variants of osteotropic genes may be obtained. For example, recombinant vectors encoding the desired osteotropic gene may be treated with mutagenic agents, such as hydroxylamine, to obtain sequence variants.

14. LTBP-2

Other aspects of the present invention concern isolated DNA segments and recombinant vectors encoding LTBP-2, and the creation and use of recombinant host cells through the application of DNA technology, that express LTBP-2 gene products. As such, the invention concerns DNA segment comprising an isolated gene that encodes a protein or peptide that includes an amino acid sequence essentially as set forth by a contiguous sequence from SEQ ID NO:3. These DNA segments are represented by those that include a nucleic acid sequence essentially as set forth by a contiguous sequence from SEQ ID NO:2 (FIG. 17). Compositions that include a purified protein that has an amino acid sequence essentially as set forth by the amino acid sequence of SEQ ID NO:3 (FIG. 18) are also encompassed by the invention.

Transforming growth factor-β (TGF-β) is a family of structurally related molecules with diverse effects on cell shape, growth, and differentiation (Roberts and Sporn, 1990; Lyons and Moses, 1990). TGF-β is initially synthesized as a precursor molecule with an amino-terminal propeptide followed by the mature or active form of TGF-β. Two chains of newly synthesized pro-TGF-β associate to form a $M_r$=~106,000 disulfide bonded dimer; homodimers are most common but heterodimers have also been described (Cheifetz et al., 1987; Ogawa et al. 1992). Cultured cells secrete all three TGF-β isoforms as latent complexes. The carboxy-termini of TGF-β precursors are cleaved from their amino-terminal propeptides during secretion, and latency results in part from the non-covalent association of the propeptide dimer and the mature TGF-β dimer. Consequently, the propeptide dimer is also known as the latency associated protein (LAP). (For additional discussion of the mechanism of latency, see Pircher et al., 1984; Pircher et al., 1986; Lyons et al., 1988; Miyazono et al., 1988; Miyazono and Heldin, 1989; Kovacina et al., 1989; Brown et al., 1990.) LAP plus the 25 kDa disulfide-bonded TGF-β dimer is also known as the small latent complex.

Latent complexes produced by cultured cells may also contain additional high molecular weight proteins to form large latent complexes (Miyazono et al., 1988; Wakefiled et al., 1988; Olofsson et al., 1992; Pircher et al., 1984, 1986; Wakefield et al., 1987). The best characterized of these proteins is a molecule known as the latent TGF-β binding protein (LTBP), which covalently binds LAP by a disulfide bond (Miyazono et al., 1988). Molecular cloning of human LTBP has shown that the molecule contains 17 epidermal growth factor-like repeats and 3 copies of a unique motif containing 8 cysteine residues (Kanzaki et al., 1990). LTBP has been shown to bind calcium, probably via its EGF-like repeats, which in turn induces a structural change that protects the molecule against proteolysis (Colosetti et al., 1993). The EGF-like repeats of LTBP may also be modified to contain hydroxyaspartic acid and hydroxyasparagine, but the significance of this finding is unknown (Kanzaki et al., 1990). LTBP contains several structurally distinct domains and it is heterogeneous, ranging in size from 125–205 kDa in different cell types because of alternative splicing of the LTBP transcript and cell specific proteolysis (Tsuji et al., 1990).

LTBP may have an important role in the assembly and secretion of latent TGF-β from cells, as evidenced by the fact that the small latent complex is secreted slowly from cultured cells and may contain anomalous disulfide bonds. The large latent TGF-β complex, on the other hand, is efficiently secreted (Miyazono et al., 1991; Miyazono et al., 1992). LTBP appears to be covalently bound to the extracellular matrix following its secretion and may therefore have the additional function of targeting latent TGF-β to specific types of connective tissue. (Taipale et al., 1994). Recent studies have shown that the subsequent release of mature TGF-β and LAP from the extracellular matrix of cultured cells occurs as a secondary consequence of the cleavage of LTBP by proteases such as plasmin and thrombin (Taipale et al., 1992; Falcone et al., 1993; Benezra et al., 1993).

Regarding the novel protein LTBP-2, the present invention concerns DNA segments, that can be isolated from virtually any mammalian source, that are free from total genomic DNA and that encode proteins having LTBP-2-like activity. DNA segments encoding LTBP-2-like species may prove to encode proteins, polypeptides, subunits, functional domains, and the like.

As used herein, the term "DNA segment" refers to a DNA molecule that has been isolated free of total genomic DNA of a particular species. Therefore, a DNA segment encoding LTBP-2 refers to a DNA segment that contains LTBP-2 coding sequences yet is isolated away from, or purified free from, total genomic DNA of the species from which the DNA segment is obtained. Included within the term "DNA segment", are DNA segments and smaller fragments of such segments, and also recombinant vectors, including, for example, plasmids, cosmids, phagemids, phage, viruses, and the like.

Similarly, a DNA segment comprising an isolated or purified LTBP-2 gene refers to a DNA segment including LTBP-2 coding sequences and, in certain aspects, regulatory sequences, isolated substantially away from other naturally occurring genes or protein encoding sequences. In this respect, the term "gene" is used for simplicity to refer to a functional protein, polypeptide or peptide encoding unit. As will be understood by those in the art, this functional term includes both genomic sequences, cDNA sequences and smaller engineered gene segments that express, or may be adapted to express, proteins, polypeptides or peptides.

"Isolated substantially away from other coding sequences" means that the gene of interest, in this case, a gene encoding LTBP-2, forms the significant part of the coding region of the DNA segment, and that the DNA segment does not contain large portions of naturally-occurring coding DNA, such as large chromosomal fragments or other functional genes or cDNA coding regions. Of course, this refers to the DNA segment as originally isolated, and does not exclude genes or coding regions later added to the segment by the hand of man.

In particular embodiments, the invention concerns isolated DNA segments and recombinant vectors incorporating DNA sequences that encode an LTBP-2 species that includes within its amino acid sequence an amino acid sequence essentially as set forth in SEQ ID NO:3. In other particular embodiments, the invention concerns isolated DNA segments and recombinant vectors incorporating DNA sequences that include within their sequence a nucleotide sequence essentially as set forth in SEQ ID NO:2.

The term "a sequence essentially as set forth in SEQ ID NO:3" means that the sequence substantially corresponds to a portion of SEQ ID NO:3 and has relatively few amino acids that are not identical to, or a biologically functional equivalent of, the amino acids of SEQ ID NO:3. The term "biologically functional equivalent" is well understood in the art and is further defined in detail herein (for example, see section 7, preferred embodiments). Accordingly, sequences that have between about 70% and about 80%; or more preferably, between about 81% and about 90%; or even more preferably, between about 91% and about 99%; of amino acids that are identical or functionally equivalent to the amino acids of SEQ ID NO:3 will be sequences that are "essentially as set forth in SEQ ID NO:3".

In certain other embodiments, the invention concerns isolated DNA segments and recombinant vectors that include within their sequence a nucleic acid sequence essentially as set forth in SEQ ID NO:2. The term "essentially as set forth in SEQ ID NO:2" is used in the same sense as described above and means that the nucleic acid sequence substantially corresponds to a portion of SEQ ID NO:2 and has relatively few codons that are not identical, or functionally equivalent, to the codons of SEQ ID NO:2. Again, DNA segments that encode proteins exhibiting LTBP-2-like activity will be most preferred.

It will also be understood that amino acid and nucleic acid sequences may include additional residues, such as additional N- or C-terminal amino acids or 5' or 3' sequences, and yet still be essentially as set forth in one of the sequences disclosed herein, so long as the sequence meets the criteria set forth above, including the maintenance of biological protein activity where protein expression is concerned. The addition of terminal sequences particularly applies to nucleic acid sequences that may, for example, include various non-coding sequences flanking either of the 5' or 3' portions of the coding region or may include various internal sequences, i.e., introns, which are known to occur within genes.

Naturally, the present invention also encompasses DNA segments that are complementary, or essentially complementary, to the sequence set forth in SEQ ID NO:2. Nucleic acid sequences that are "complementary" are those that are capable of basepairing according to the standard Watson-Crick complementarity rules. As used herein, the term "complementary sequences" means nucleic acid sequences that are substantially complementary, as may be assessed by the same nucleotide comparison set forth above, or as defined as being capable of hybridizing to the nucleic acid segment of SEQ ID NO:2, under relatively stringent conditions such as those described herein.

The nucleic acid segments of the present invention, regardless of the length of the coding sequence itself, may be combined with other DNA sequences, such as promoters, polyadenylation signals, additional restriction enzyme sites, multiple cloning sites, other coding segments, and the like, such that their overall length may vary considerably. It is therefore contemplated that a nucleic acid fragment of almost any length may be employed, with the total length preferably being limited by the ease of preparation and use in the intended recombinant DNA protocol. For example, nucleic acid fragments may be prepared that include a short contiguous stretch identical to or complementary to SEQ ID NO:2, such as about 14 nucleotides, and that are up to about 10,000 or about 5,000 base pairs in length, with segments of about 3,000 being preferred in certain cases. DNA segments with total lengths of about 1,000, about 500, about 200, about 100 and about 50 base pairs in length (including all intermediate lengths) are also contemplated to be useful.

It will be readily understood that "intermediate lengths", in these contexts, means any length between the quoted ranges, such as 14, 15, 16, 17, 18, 19, 20, etc.; 21, 22, 23, etc; 30, 31, 32, etc.; 50, 51, 52, 53, etc.; 100, 101, 102, 103, etc.; 150, 151, 152, 153, etc.; including all integers through the 200–500; 500–1,000; 1,000–2,000; 2,000–3,000; 3,000–5,000; 5,000–10,000 ranges, up to and including sequences of about 12,001, 12,002, 13,001, 13,002 and the like.

It will also be understood that this invention is not limited to the particular nucleic acid and amino acid sequences of SEQ ID NO:2 and SEQ ID NO:3. Recombinant vectors and isolated DNA segments may therefore variously include the LTBP-2 coding regions themselves, coding regions bearing selected alterations or modifications in the basic coding region, or they may encode larger polypeptides that nevertheless include LTEP-2-coding regions or may encode biologically functional equivalent proteins or peptides that have variant amino acids sequences.

The DNA segments of the present invention encompass biologically functional equivalent LTBP-2 proteins and peptides. Such sequences may arise as a consequence of codon redundancy and functional equivalency that are known to occur naturally within nucleic acid sequences and the proteins thus encoded. Alternatively, functionally equivalent proteins or peptides may be created via the application of recombinant DNA technology, in which changes in the protein structure may be engineered, based on considerations of the properties of the amino acids being exchanged. Changes designed by man may be introduced through the application of site-directed mutagenesis techniques, e.g., to introduce improvements to the antigenicity of the protein or to test mutants in order to examine activity at the molecular level.

If desired, one may also prepare fusion proteins and peptides, e.g., where the LTBP-2 coding regions are aligned within the same expression unit with other proteins or peptides having desired functions, such as for purification or immunodetection purposes (e.g., proteins that may be purified by affinity chromatography and enzyme label coding regions, respectively).

Recombinant vectors form further aspects of the present invention. Particularly useful vectors are contemplated to be those vectors in which the coding portion of the DNA segment, whether encoding a full length protein or smaller peptide, is positioned under the control of a promoter. The promoter may be in the form of the promoter that is naturally associated with a LTBP-2 gene, as may be obtained by isolating the 5' non-coding sequences located upstream of the coding segment or exon, for example, using recombinant cloning and/or PCR technology, in connection with the compositions disclosed herein.

In other embodiments, it is contemplated that certain advantages will be gained by positioning the coding DNA segment under the control of a recombinant, or heterologous, promoter. As used herein, a recombinant or heterologous promoter is intended to refer to a promoter that is not normally associated with an LTBP-2 gene in its natural environment. Such promoters may include LTBP-2 promoters normally associated with other genes, and/or promoters isolated from any bacterial, viral, eukaryotic, or mammalian cell. Naturally, it will be important to employ a promoter that effectively directs the expression of the DNA segment in the cell type, organism, or even animal, chosen for expression. The use of promoter and cell type combinations for protein expression is generally known to those of skill in the art of molecular biology, for example, see Sambrook et al. (1989). The promoters employed may be constitutive, or inducible, and can be used under the appropriate conditions to direct high level expression of the introduced DNA segment, such as is advantageous in the large-scale production of recombinant proteins or peptides. Appropriate promoter systems contemplated for use in high-level expression include, but are not limited to, the Pichia expression vector system (Pharmacia LKB Biotechnology) (see Example XVI herein).

In connection with expression embodiments to prepare recombinant LTBP-2 proteins and peptides, it is contemplated that longer DNA segments will most often be used, with DNA segments encoding the entire LTBP-2 protein or functional domains, subunits, etc. being most preferred. However, it will be appreciated that the use of shorter DNA segments to direct the expression of LTBP-2 peptides or epitopic core regions, such as may be used to generate anti-LTBP-2 antibodies, also falls within the scope of the invention. DNA segments that encode peptide antigens from about 15 to about 50 amino acids in length, or more preferably, from about 15 to about 30 amino acids in length are contemplated to be particularly useful.

The LTBP-2 gene and DNA segments may also be used in connection with somatic expression in an animal or in the creation of a transgenic animal. Again, in such embodiments, the use of a recombinant vector that directs the expression of the full length or active LTBP-2 protein is particularly contemplated.

In addition to their use in directing the expression of the LTBP-2 protein, the nucleic acid sequences disclosed herein also have a variety of other uses. For example, they also have utility as probes or primers in nucleic acid hybridization embodiments. As such, it is contemplated that nucleic acid segments that comprise a sequence region that consists of at least a 14 nucleotide long contiguous sequence that has the same sequence as, or is complementary to, a 14 nucleotide long contiguous sequence of SEQ ID NO:2 will find particular utility. Longer contiguous identical or complementary sequences, e.g., those of about 20, 30, 40, 50, 100, 200, 500, 1000 (including all intermediate lengths) and even up to full length sequences will also be of use in certain embodiments.

The ability of such nucleic acid probes to specifically hybridize to LTBP-2-encoding sequences will enable them to be of use in detecting the presence of complementary sequences in a given sample. However, other uses are envisioned, including the use of the sequence information for the preparation of mutant species primers, or primers for use in preparing other genetic constructions.

Nucleic acid molecules having sequence regions consisting of contiguous nucleotide stretches of 10–14, 15–20, 30, 50, or even of 100–200 nucleotides or so, identical or complementary to SEQ ID NO:2, are particularly contemplated as hybridization probes for use in, e.g., Southern and Northern blotting. This would allow LTBP-2 structural or regulatory genes to be analyzed, both in diverse cell types and also in various mammalian cells. The total size of fragment, as well as the size of the complementary stretch (es), will ultimately depend on the intended use or application of the particular nucleic acid segment. Smaller fragments will generally find use in hybridization embodiments, wherein the length of the contiguous complementary region may be varied, such as between about 10–14 and about 100 nucleotides, but larger contiguous complementary stretches may be used, according to the length complementary sequences one wishes to detect.

The use of a hybridization probe of about 10–14 nucleotides in length allows the formation of a duplex molecule that is both stable and selective. Molecules having contiguous complementary sequences over stretches greater than 10 bases in length are generally preferred, though, in order to increase stability and selectivity of the hybrid, and thereby improve the quality and degree of specific hybrid molecules obtained. One will generally prefer to design nucleic acid molecules having gene-complementary stretches of 15 to 20 contiguous nucleotides, or even longer where desired.

Hybridization probes may be selected from any portion of any of the sequences disclosed herein. All that is required is to review the sequence set forth in SEQ ID NO:2 and to select any continuous portion of the sequence, from about 10–14 nucleotides in length up to and including the full length sequence, that one wishes to utilize as a probe or primer. The choice of probe and primer sequences may be governed by various factors, such as, by way of example only, one may wish to employ primers from towards the termini of the total sequence.

The process of selecting and preparing a nucleic acid segment that includes a contiguous sequence from within SEQ ID NO:2 may alternatively be described as preparing a nucleic acid fragment. Of course, fragments may also be obtained by other techniques such as, e.g., by mechanical shearing or by restriction enzyme digestion. Small nucleic acid segments or fragments may be readily prepared by, for example, directly synthesizing the fragment by chemical means, as is commonly practiced using an automated oligonucleotide synthesizer. Also, fragments may be obtained by application of nucleic acid reproduction technology, such as the PCR technology of U.S. Pat. No. 4,603,102 (incorporated herein by reference), by introducing selected sequences into recombinant vectors for recombinant production, and by other recombinant DNA techniques generally known to those of skill in the art of molecular biology.

Accordingly, the nucleotide sequences of the invention may be used for their ability to selectively form duplex molecules with complementary stretches of LTBP-2 genes or cDNAs. Depending on the application envisioned, one will desire to employ varying conditions of hybridization to achieve varying degrees of selectivity of probe towards target sequence. For applications requiring high selectivity, one will typically desire to employ relatively stringent conditions to form the hybrids, e.g., one will select relatively low salt and/or high temperature conditions, such as provided by 0.02M–0.15M NaCl at temperatures of 50° C. to 70° C. Such selective conditions tolerate little, if any, mismatch between the probe and the template or target strand, and would be particularly suitable for isolating LTBP-2 genes.

Of course, for some applications, for example, where one desires to prepare mutants employing a mutant primer strand hybridized to an underlying template or where one seeks to isolate LTBP-2-encoding sequences from related species, functional equivalents, or the like, less stringent hybridization conditions will typically be needed in order to allow formation of the heteroduplex. In these circumstances, one may desire to employ conditions such as 0.15M–0.9M salt, at temperatures ranging from 20° C. to 55° C. Cross-hybridizing species can thereby be readily identified as positively hybridizing signals with respect to control hybridizations. In any case, it is generally appreciated that conditions can be rendered more stringent by the addition of increasing amounts of formamide, which serves to destabilize the hybrid duplex in the same manner as increased temperature. Thus, hybridization conditions can be readily manipulated, and thus will generally be a method of choice depending on the desired results.

In certain embodiments, it will be advantageous to employ nucleic acid sequences of the present invention in combination with an appropriate means, such as a label, for determining hybridization. A wide variety of appropriate indicator means are known in the art, including fluorescent, radioactive, enzymatic or other ligands, such as avidin/biotin, which are capable of giving a detectable signal. In preferred embodiments, one will likely desire to employ a fluorescent label or an enzyme tag, such as urease, alkaline phosphatase or peroxidase, instead of radioactive or other environmental undesirable reagents. In the case of enzyme tags, calorimetric indicator substrates are known that can be employed to provide a means visible to the human eye or spectrophotometrically, to identify specific hybridization with complementary nucleic acid-containing samples.

In general, it is envisioned that the hybridization probes described herein will be useful both as reagents in solution hybridization as well as in embodiments employing a solid phase. In embodiments involving a solid phase, the test DNA (or RNA) is adsorbed or otherwise affixed to a selected matrix or surface. This fixed, single-stranded nucleic acid is then subjected to specific hybridization with selected probes under desired conditions. The selected conditions will depend on the particular circumstances based on the particular criteria required (depending, for example, on the G+C contents, type of target nucleic acid, source of nucleic acid, size of hybridization probe, etc.). Following washing of the hybridized surface so as to remove nonspecifically bound probe molecules, specific hybridization is detected, or even quantified, by means of the label.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE I

Animal Model for Assessing New Bone Formation

As various animal models were not suitable for studying the effects of nucleic acid transfer on bone formation, the inventors employed the following model system. The important features of the rat osteotomy model are as described in the following protocol (which is generally completed in 25–35 minutes).

The osteotomy was performed on one femur per animal. Right to left differences have not been apparent, but such differences are monitored in these studies, since the limb receiving the osteotomy is randomized.

After pre-operative preparation (i.e. shaving and betadine scrub), adult male Sprague Dawley rats (~500 gm, retired male breeders) were anesthetized using a 3%. halothane 97% oxygen mixture (700 ml/min. flow rate). A lateral approach to the femur was made on one limb. Utilizing specially designed surgical guides, four 1.2 mm diameter pins were screwed into the diaphysis after pre-drilling with a high speed precision bit. A surgical template ensured precise and parallel placement of the pins. The order of pin placement was always the same: outer proximal first and then outer distal, inner proximal and inner distal (with "outer" and "inner" referring to the distance from the hip joint). Pin placement in the center of the femur was ensured by fluoroscopic imaging during pin placement. The external fixator was secured on the pins and a t mm or 2 mm segmental defect was created in the central diaphysis through an incision using a Hall Micro 100 Oscillating saw (#5053-60 Hall surgical blades) under constant irrigation. Other than the size of the segmental defect, there is no difference between the 5 mm and 2 mm osteotomy protocols (FIG. 1).

The contents of the osteotomy site were irrigated with sterile saline and the fibrous collagen implant material, previously soaked in a solution of plasmid DNA or other DNA construct, if appropriate, was placed in situ. The wound was then closed in layers. Since the fixator provided the necessary stability no limitations on animal ambulation existed, and other supports were not required. The surgical protocol has been successfully performed on 21/21 animals to date. None of these animals have died and no significant adverse effects have been observed, other than complications that might be associated with surgical fracture repair. Minor complications that were experienced include 1 animal that developed a post-operative osteomyelitis and 1 animal in which 2/4 pins loosened as a consequence of bone fracture.

EXAMPLE II

Implant Material for use in Bone Gene Transfer

Various implant materials may be used for transferring genes into the site of bone repair and/or regeneration in vivo. These materials are soaked in a solution containing the DNA or gene that is to be transferred to the bone regrowth site.

One particular example of a suitable material is fibrous collagen, which may be lyophilized following extraction and partial purification from tissue and then sterilized. A particularly preferred collagen is the fibrous collagen implant material termed UltraFiber™, as may be obtained from Norian Corp., (1025 Terra Bella Ave., Mountain View, Calif., 94043). Detailed descriptions of the composition and use of UltraFiber™ are provided in Gunasekaran et al. (1993a,b; each incorporated herein by reference).

A more particularly preferred collagen is type II collagen, with most particularly preferred collagen being either recombinant type II collagen, or mineralized type II collagen.

Prior to placement in osteotomy sites, implant materials are soaked in solutions of DNA (or virus) under sterile conditions. The soaking may be for any appropriate and convenient period, e.g., from 6 minutes to over-night. The DNA (e.g., plasmid) solution will be a sterile aqueous solution, such as sterile water or an acceptable buffer, with the concentration generally being about 0.5–1.0 mg/ml. Currently preferred plasmids are those such as pGL2 (Promega), pSV40β-gal, pAd.CMVlacZ, and pLJ.

EXAMPLE III

Parathyroid Hormone Gene Constructs

The active fragment of the human parathyroid hormone gene (hPTH1-34) was chosen as the first of the osteotropic genes to be incorporated into an expression vector for use in gene transfer to promote new bone formation in the rat osteotomy model.

Figure 2:
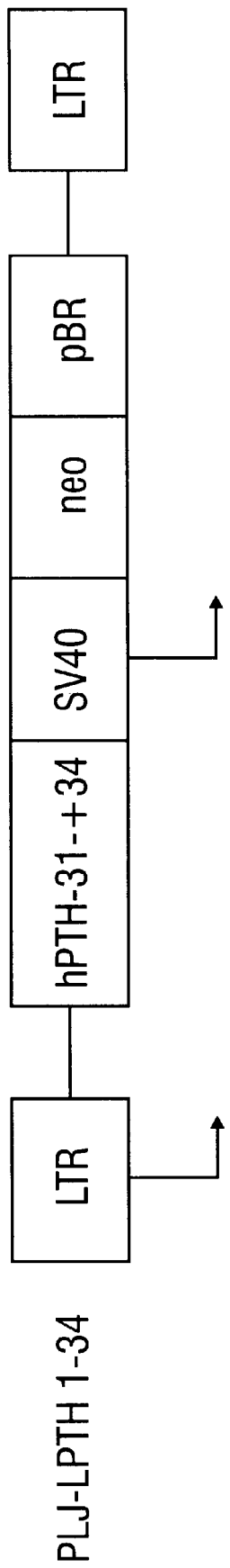
FIG. 2. PLJ-HPTH1-34 expression construct. A cDNA fragment coding for a prepro-hPTH1-34 peptide was generated by PCR (Hendy et al., 1981) and then ligated into a BamHI cloning site in the PLJ retroviral expression vector (Wilson et al., 1992). Several independent clones with the insert in the coding orientation were isolated and characterized.

The inventors chose to construct the hPTH1-34 transgene in the PLJ expression vector (FIG. 2), since this vector was appropriate for studies of transgene function both in vitro and in vivo. A schematic of the PLJ-hPTH1-34 transgene is shown in FIG. 2. The DNA and amino acid sequences of the hPTH1-34 are well known, e.g., see Hendy et al. (1981, incorporated herein by reference). To insert the transgene into the PLJ expression vector PCR of a full-length PTH recombinant clone was employed, followed by standard molecular biological manipulation.

A retroviral stock was then generated following $CaPO_4$-mediated transfection of psi crip cells with the PLJ-hPTH1-34 construct, all according to standard protocols (Sambrook et al., 1989). Independent transduced Rat-1 clones were obtained by standard infection and selection procedures (Sambrook et al., 1989).

Figure 3:
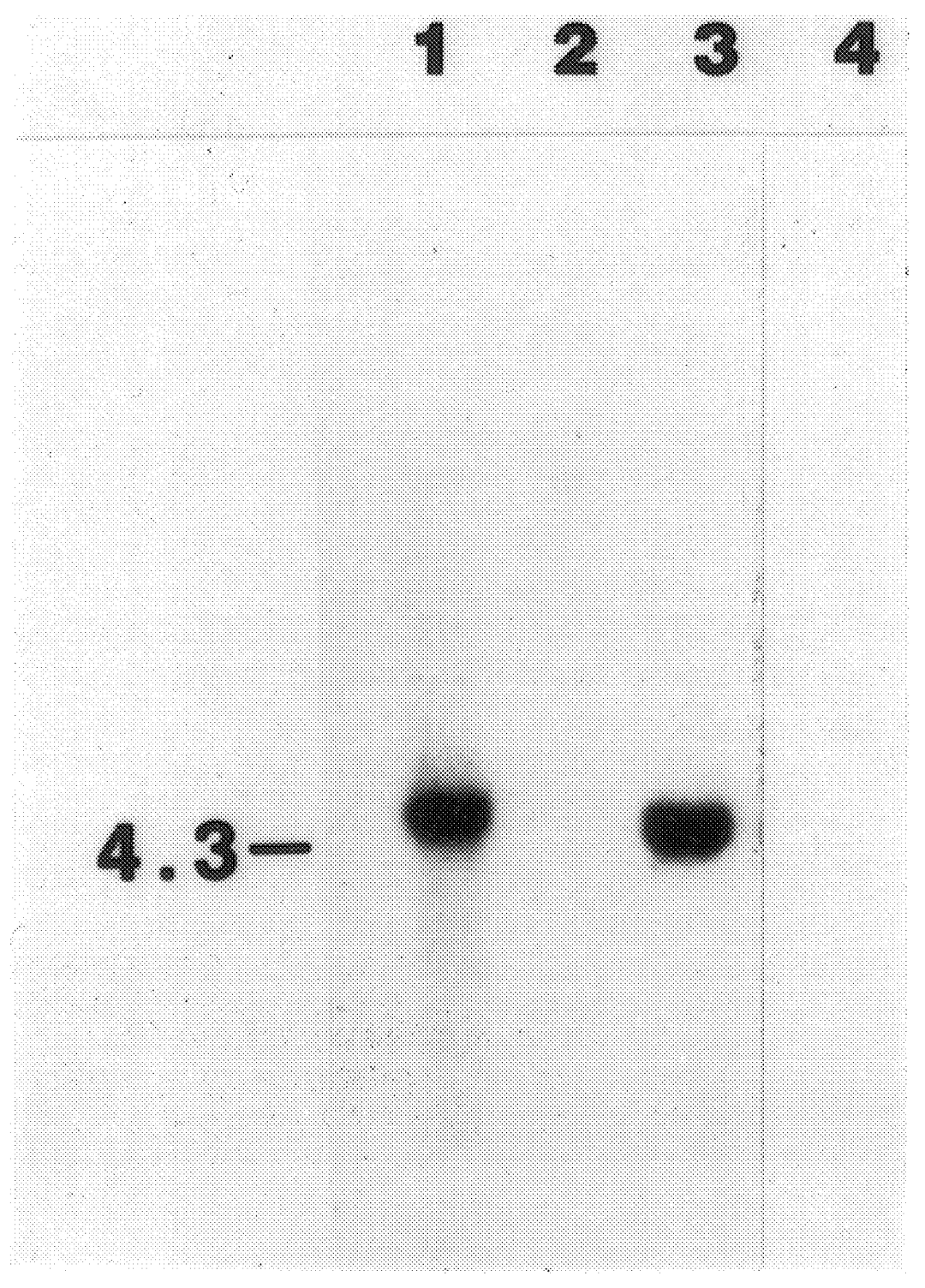

One clone (YZ-15) was analyzed by Southern analysis, demonstrating that the PLJ-hPTH1-34 transgene had stably integrated into the Rat-1 genome (FIG. 3). A Northern analysis was next performed to show that the YZ-15 clone expressed the PLJ-hPTH1-34 transgene, as evidenced by the presence of specific PLJ-hPTH1-34 transcripts (FIG. 4A).

EXAMPLE IV

Parathyroid Hormone Polypeptide Expression and Activity

A sensitive and specific radioimmunoassay was performed to demonstrate that the YZ-15 cells expressed and secreted a recombinant hPTH1-34 molecule (Table 2). The radioimmunoassay was performed on media from transduced Rat-1 clones. To quantify secretion of the recombinant hPTH-1–34 peptide produced by YZ-15 cells, the culture medium from one 100 mm confluent dish was collected over a 24 hour period and assayed with the NH2-terminal hPTH RIA kit (Nichols Institute Diagnostics) according to the manufacturer's protocol. PLJ-hPTH1-87 cells and BAG cells served as positive and negative controls, respectively.

Protein concentrations in Table 2 are expressed as the average of three assays plus the standard deviation (in parenthesis). The concentration of the 1–34 and full length (1–84) peptides was determined relative to a standard curve generated with commercially available reagents (Nichols Institute Diagnostics).

TABLE 2

| CELL LINES | PTH (pg/ml) |
| --- | --- |
| YZ-15 | 247 (±38) |
| PLJ-hPTH1-84 | 2616 (±372) |
| BAG | 13 (±3) |

As shown in Table 2, PTH expression was detected in both YZ-15 cells and PLJ-hPTH1-84 cells. BAG cells produced no detectable PTH and served as a baseline for the RIA. These results demonstrate that YZ-15 cells expressed recombinant hPTH1-34 protein.

The recombinant hPTH1-34 molecule was added to rat osteosarcoma cells and a cAMP response assay conducted in order to determine whether the secreted molecule had biological activity. Unconcentrated media was collected from YZ-15 cells, PLJ-hPTH1-84 cells, and BAG cells and was used to treat ROS17/2.8 cells for 10 minutes, as described (Majmudar et al., 1991). cAMP was then extracted from treated cells and quantified by RIA (Table 3). The amount of cAMP shown is the average of three assays. The standard deviation of the mean is shown in parenthesis.

TABLE 3

| CELL LINES | cAMP (pmol) |
| --- | --- |
| YZ-15 | 20.3 (±0.25) |
| PLJ-hPTH184 | 88.5 (±4.50) |
| BAG | 7.6 (±0.30) |

A cAMP response was induced by the recombinant PTH secreted by the YZ-15 cells and by PLJ-hPTH1-84 cells. BAG cells produced no PTH and served as the baseline for the cAMP assay. These results provide direct in vitro evidence that the PLJ-hPTH1-34 transgene directs the expression and secretion of a functional osteotropic agent.

EXAMPLE V

Bone Morphogenetic Protein (BMP) Gene Constructs

The mouse bone morphogenetic protein-4 (BMP-4) was chosen as the next of the osteotropic genes to be incorporated into an expression vector for use in promoting bone repair and regeneration.

A full length mouse BMP-4 cDNA was generated by screening a mouse 3%3 cell CDNA library (Stratagene). The human sequence for BMP-4 is well known to those of skill in the art and has been deposited in Genbank. Degenerate oligos were prepared and employed in standard PCR to obtain a murine cDNA sequence.

The ends of the CDNA clone were further modified using the polymerase chain reaction so that the full length cDNA (5'→3' direction) codes for: the natural mouse initiator Met codon, the full length mouse coding sequence, a 9 amino acid tag (known as the HA epitope), and the natural mouse stop codon. The amino acid sequence encoded by the mouse BMP-4 transgene is shown in FIG. 9; this entire sequence, including the tag, is represented by SEQ ID NO:1. As of the filing of this application, the precise nucleic acid sequence has not yet been determined, and various "wobble position" bases remain unknown.

Placement of the HA epitope at the extreme carboxy terminus should not interfere with the function of the recombinant molecule sequence in vitro or in vivo. The advantage of the epitope is for utilization in immunohistochemical methods to specifically identify the recombinant mouse BMP-4 molecule in osteotomy tissues in vivo, e.g., the epitope can be identified using a commercially available monoclonal antibody (Boehringer-Mannheim), as described herein.

Studies to demonstrate that the mouse BMP-4 transgene codes for a functional osteotropic agent include, for example, (a) transfection of COS cells and immunoprecipitation of a protein band of the correct size using a monoclonal anti-HA antibody (Boehringer-Mannheim); and (b) a quantitative in vivo bone induction bioassay (Sampath & Reddi, 1981) that involves implanting proteins from the medium of transfected COS cells beneath the skin of male rats and scoring for new bone formation in the ectopic site.

EXAMPLE VI

Detection of mRNA by Tissue in situ Hybridization

The following technique describes the detection of mRNA in tissue obtained from the site of bone regeneration. This may be useful for detecting expression of the transgene mRNA itself, and also in detecting expression of hormone or growth factor receptors or other molecules. This method may be used in place of, or in addition to, Northern analyses, such as those described in FIG. 7.

DNA from a plasmid containing the gene for which mRNA is to be detected is linearized, extracted, and precipitated with ethanol. Sense and antisense transcripts are generated from 1 mg template with T3 and T7 polymerases, e.g., in the presence of [$^{35}$S] UTP at >6 mCi/ml (Amersham Corp., >1200 Ci/mmol) and 1.6 U/ml RNasin (Promega), with the remaining in vitro transcription reagents provided in a kit (SureSite, Novagen Inc.). After transcription at 37° C. for 1 hour, DNA templates are removed by a 15 minute digestion at 37° C. with 0.5 U/ml RNase-free DNase I, extracted, and precipitated with ethanol. Riboprobes are hydrolyzed to an average final length of 150 bp by incubating in 40 mM NaHCO$_3$, 60 mM Na$_2$CO$_3$, 80 mM DTT at 60° C., according to previously determined formula. Hydrolysis is terminated by addition of sodium acetate, pH 6.0, and glacial acetic acid to 0.09M and 0.005% (v/v), respectively, and the probes are then ethanol precipitated, dissolved in 0.1M DTT, counted, and stored at -20° C. until use.

RNase precautions are taken in all stages of slide preparation. Bouins fixed, paraffin embedded tissue sections are heated to 65° C. for 10 minutes, deparaffinized in 3 changes of xylene for 5 minutes, and rehydrated in a descending ethanol series, ending in phosphate-buffered saline (PBS). Slides will be soaked in 0.2 N HCl for 5 min., rinsed in PBS, digested with 0.0002% proteinase K in PBS for 30 minutes at 37° C. and rinsed briefly with DEPC-treated water. After equilibrating for 3 minutes in 0.1M triethanolamine-HCl (TEA-HCl), pH 8.0, sections are acetylated in 0.25% (v/v) acetic anhydride in 0.1M TEA-HCl for 10 minutes at room temperature, rinsed in PBS, and dehydrated in an ascending ethanol series. Each section receives 100–200 ml prehybridization solution (0.5 mg/ml denatured RNase-free tRNA (Boehringer-Mannheim), 10 mM DTT, 5 mg/ml denatured, sulfurylated salmon sperm DNA, 50% formamide, 10% dextran sulfate, 300 mM NaCl, 1x RNase-free Denhardt's solution (made with RNase-free bovine serum albumin, Sigma), 10 mM Tris-HCl, pH 7.4, 1 mM EDTA) and then incubate on a 50° C. slide warmer in a humidified enclosure for 2 hours. The sulfurylated salmon-sperm DNA blocking reagent is used in both prehybridization and hybridization solutions to help reduce nonspecific binding to tissue by $^{35}$SH groups on the probe. It is prepared by labeling RNase-free salmon sperm DNA (Sigma) with non-radioactive α-thio-dCTP and α-thio-dATP (Amersham) in a standard random oligonucleotide-primed DNA labeling reaction. Excess prehybridization solution is removed with a brief rinse in 4x SSC before application of probe.

Riboprobes, fresh tRNA and sulfurylated salmon sperm DNA will be denatured for 10 minutes at 70° C., and chilled on ice. Hybridization solution, identical to prehybridization solution except with denatured probe added to 5×10$^6$CPM/ml, is applied and slides incubated at 50° C. overnight in sealed humidified chambers on a slide warmer. Sense and antisense probes are applied to serial sections. Slides are rinsed 3 times in 4x SSC, washed with 2x SSC, 1 mM DTT for 30 min. at 50° C., digested with RNase A (20 mg/ml RNase A, 0.5M NaCl, 10 mM Tris, pH 8.0, 1 mM EDTA, pH 8.0) for 30 min. at 37° C., and rinsed briefly with 2x SSC, 1 mM DTT. Three additional washes are performed, each at 50° C. for 30 minutes: once in 2x SSC, 50% formamide, 1 mM DTT, and twice in 1x SSC, 0.13% (w/v) sodium pyrophosphate, 1 mM DTT.

Slides are dehydrated in an ascending ethanol series (with supplementation of the dilute ethanols (50% and 70%) with SSC and DTT to 0.1x and 1 mM, respectively). Slides are exposed to X-ray film for 20–60 hours to visualize overall hybridization patterns, dipped in autoradiographic emulsion (Kodak NTB-2, diluted to 50% with 0.3M ammonium acetate), slowly dried for 2 hours, and exposed (4° C.) for periods ranging from 8 days to 8 weeks. After developing emulsion, sections are counter strained with hematoxylin and eosin, dehydrated, and mounted with xylene-based medium. The hybridization signal is visualized under darkfield microscopy.

The above in situ hybridization protocol may be used, for example, in detecting the temporal and spatial pattern of PTH/PTHrP receptor expression. A suitable rat PTH/PTHrP receptor cDNA probe (R15B) is one that consists of a 1810 bp region encoding the full length rat bone PTH/PTHrP receptor (Abou-Samra et al., 1992). The cDNA fragment is subcloned into pcDNA 1 (Invitrogen Corp., San Diego, Calif.) and is cut out using XbaI and BamHI. This probe has provided positive signals for northern blot analysis of rat, murine, and human osteoblastic cell lines, rat primary calvarial cells, and murine bone tissue. The pcDNA I plasmid contains a T7 and SP6 promoter that facilitate the generation of cRNA probes for in situ hybridization. The full length transcript has been used to detect PTH/PTHrP receptor in sections of bone (Lee et al., 1994). The PTHrP cDNA probe (Yasuda et al., 1989) is a 400 bp subcloned fragment in pBluescript 1 KS (Stratagene). This probe has been used for in situ hybridization, generating an antisense cRNA probe using BamHI cleavage and the T3 primer and a sense cRNA probe using EcoRI cleavage and the T7 primer.

EXAMPLE VII

In vivo Protein Detection following Transgene Expression

1. β-galactosidase Transgene

Bacterial β-galactosidase is detected immunohistochemically and by substrate utilization assays. Osteotomy tissue specimens are fixed in Bouins fixative, demineralized, and then split in half along the longitudinal plane. One-half of each specimen is embedded in paraffin for subsequent immunohistochemical identification of the bacterial β-galactosidase protein.

For immunohistochemistry, cross-Sections (2–3 mm thick) were transferred to poly-L-Lysine coated microscope slides and fixed in acetone at 0° C. for at least 20 min. Sections were rehydrated in PBS. Endogenous peroxidase activity was quenched by immersion of tissue sections in 0.1% hydrogen peroxide (in 95% methanol) at room temperature for 10 min, and quenched sections were washed 3× in PBS. In some cases, sectioned calvariae were demineralized by immersion in 4% EDTA, 5% polyvinyl pyrrolidone, and 7% sucrose, pH 7.4, for 24 h at 4° C. Demineralized sections were washed 3× before application for antibodies. Primary antibodies were used without dilution in the form of hybridoma supernatant. Purified antibodies were applied to tissue sections at a concentration of 5 mg/ml. Primary antibodies were detected with biotinylated rabbit antimouse IgG and peroxidase conjugated streptavidin (Zymed Histostain-SPkit). After peroxidase staining, sections were counterstained with hematoxylin.

Substrate utilization assays (for both β-gal and luciferase) are conducted using commercially available kits (e.g., Promega) according to the manufacturers' instructions.

2. PTH Transgenes

Recombinant PTH, such as hPTH1-34 peptide, is assayed in homogenates of osteotomy gap tissue, for example, using two commercially available radioimmunoassay kits according to the manufacturer's protocols (Nichols Institute Diagnostics, San Juan Capistrano, Calif.).

One kit is the Intact PTH-Parathyroid Hormone 100T Kit. This radioimmunoassay utilizes an antibody to the carboxy terminus of the intact hormone, and thus is used to measure endogenous levels of hormone in gap osteotomy tissue. This assay may be used to establish a baseline value PTH expression in the rat osteotomy model.

The second kit is a two-site immunoradiometric kit for the measurement of rat PTH. This kit uses affinity purified antibodies specific for the amino terminus of the intact rat hormone (PTH1-34) and thus will measure endogenous PTH production as well as the recombinant protein. Previous studies have shown that these antibodies cross-react with human PTH and thus are able to recognize recombinant molecules in vivo.

Values obtained with kit #1 (antibody to the carboxy terminus) are subtracted from values obtained with kit #2 (antibody to the amino terminus) to obtain an accurate and sensitive measurements. The level of recombinant peptide is thus correlated with the degree of new bone formation.

3. BMP Transgene

Preferably, BMP proteins, such as the mouse BMP-4 transgene peptide product, are detected immunohistochemically using a specific antibody that recognizes the HA epitope (Majmudar et al., 1991), such as the monoclonal antibody available from Boehringer-Mannheim. Antibodies to BMP proteins themselves may also be used. Such antibodies, along with various immunoassay methods, are described in U.S. Pat. No. 4,857,456, incorporated herein by reference.

Osteotomy tissue specimens are fixed in Bouins fixative, demineralized, and then split in half along the longitudinal plane. One-half of each specimen is embedded in paraffin for subsequent immunohistochemical identification of the recombinant mouse BMP-4 molecule.

EXAMPLE VIII

Direct Gene Transfer into Regenerating Bone In Vivo

To assess the feasibility of direct gene transfer into regenerating bone in vivo, marker gene transfer into cells in the rat osteotomy model was employed. These studies involved two marker genes: bacterial β-galactosidase and insect luciferase.

Aliquots of a fibrous collagen implant material were soaked in solutions of pure marker gene DNA. The implant materials were then placed in the osteotomy site, and their expression determined as described above.

Figure 5:
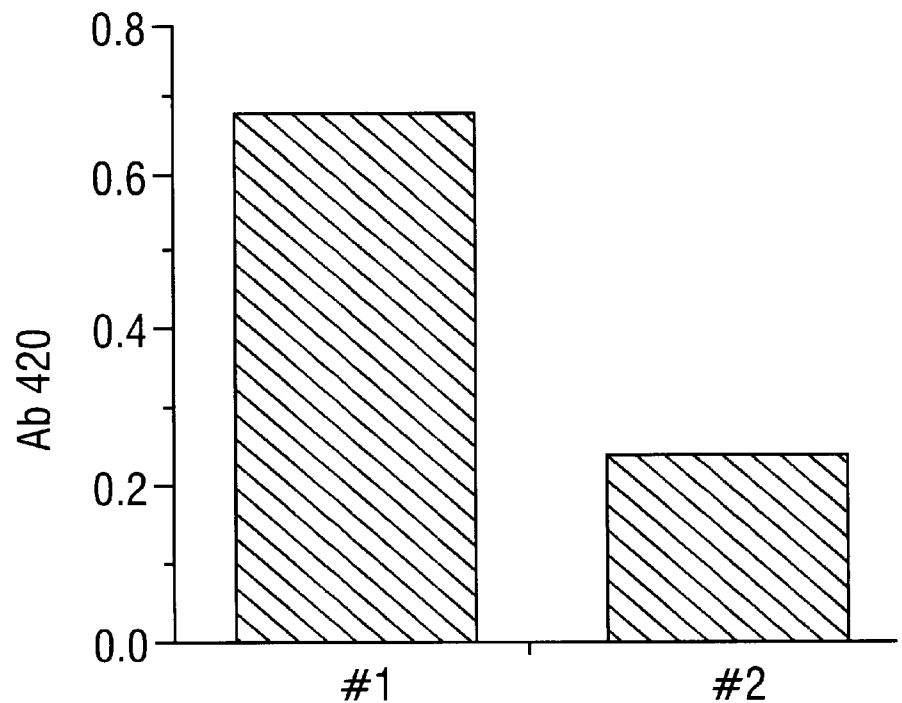
FIG. 5. Direct DNA transfer into regenerating bone: β-gal activity. The figure compares β-galactosidase activity in homogenates of osteotomy gap tissue from two Sprague-Dawley rats. In animal #1, the UltraFiber™ implant material was soaked in a solution of pSV40β-gal DNA, Promega) encoding bacterial β-galactosidase. In animal #2, the implant material was soaked in a pure solution of pGL2-Promoter Vector DNA (Promega) encoding insect luciferase. Enzyme activity was determined using substrate assay kits (β-galactosidase and Luciferase Assay Systems, Promega). Note that significant β-galactosidase activity was found only in the homogenate prepared from animal #1.
Figure 6:
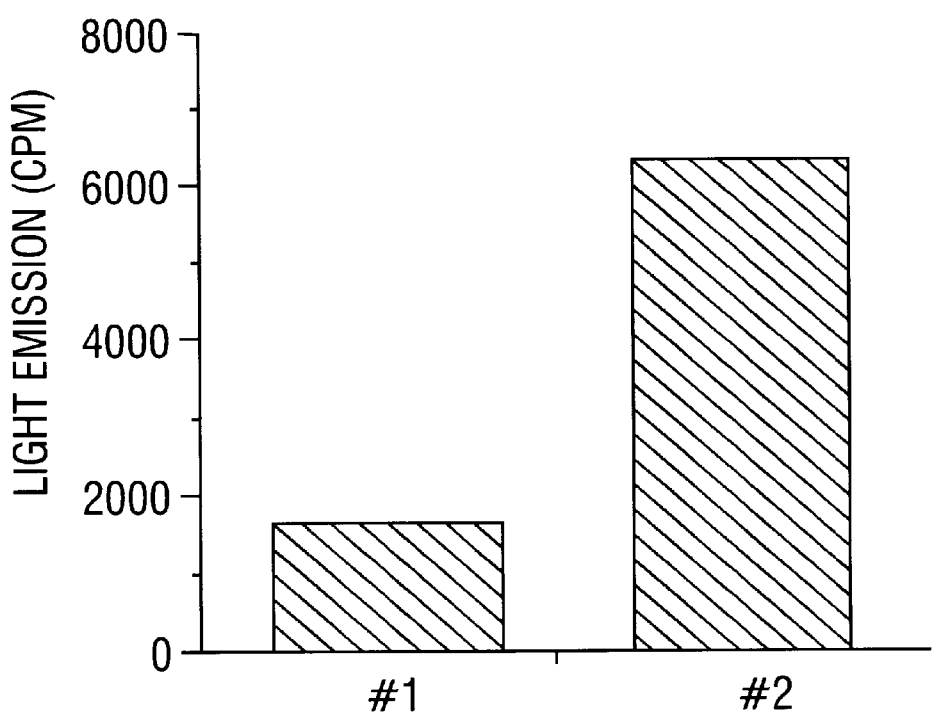
FIG. 6. Direct DNA transfer into regenerating bone: luciferase activity. The figure compares luciferase activity in aliquots of the homogenates described in FIG. 5. Luciferase activity was determined using the commercial reagents and protocols (Promega) described in FIG. 5. Note that significant luciferase activity is found only in the homogenate prepared from animal #2.

It was found that bot marker genes were successfully transferred and expressed, without any failures, as demonstrated by substrate utilization assays (FIG. 5 and FIG. 6). Since mammalian cells do not normally synthesize either marker gene product, this provides direct evidence that osteotomy repair cells were transfected in vivo and then expressed the β-galactosidase and luciferase transgenes as a functional enzymes.

EXAMPLE IX

Adenoviral Gene Transfer into Regenerating Bone in vivo

One of the alternative methods to achieve in vivo gene transfer into regenerating bone is to utilize an adenovirus-mediated transfer event. Successful adenoviral gene transfer of a marker gene construct into bone repair cells in the rat osteotomy model has been achieved.

The inventors employed the adenoviral vector pAd.CMVlacZ, which is an example of a replication-defective adenoviral vector which can replicate in permissive cells (Stratford-Perricaudet et al., 1992). In pAd.CMVlacZ, the early enhancer/promoter of the cytomegalovirus (CMV) is used to drive transcription of lacZ with an SV40 polyadenylation sequence cloned downstream from this reporter (Davidson et al., 1993).

The vector pAd.RSV4 is also utilized by the inventors. This vector essentially has the same backbone as pAdCMVlacZ, however the CMV promoter and the single BglII cloning site have been replaced in a cassette-like fashion with BglII fragment that consists of an RSV promoter, a multiple cloning site, and a poly($A^+$) site. The greater flexibility of this vector is contemplated to be useful in subcloning osteotropic genes, such as the hPTH1-34 cDNA fragment, for use in further studies.

To generate recombinant PTH adenovirus, a 100 mm dish of 293 cells is transfected using calcium phosphate with 20 mg of a plasmid construct, e.g., the plasmid containing the hPTH1-34 insert linearized with NheI, plus 2 mg of wild type adenovirus DNA digested with XbaI and ClaI. The adenovirus DNA is derived from adenovirus type 5, which contains only a single XbaI and ClaI sites and has a partial deletion of the E3 region. Approximately 7 days post-transfection, cells and media are harvested and a lysate prepared by repeated freeze-thaw cycles. This lysate is diluted and used to infect 60 mm dishes of confluent 293 cells for 1 hour. The cells are then overlaid with 0.8% agar/1× MEM/2% calf serum/12.5 mM $MgCl_2$. Ten days post-infection, individual plaques are to be picked and used to infect 60 mm dishes of 293 cells to expand the amount of virus. Positive plaques are selected for further purification and the generation of adenoviral stocks.

To purify recombinant adenovirus, 150 mm dishes of 75–90% confluent 293 cells are infected with 2–5 PFU/cell, a titer that avoids the potential cytotoxic effects of adenovirus. Thirty hours post-infection, the cells are rinsed, removed from the dishes, pelleted, and resuspended in 10 mM Tris-HCl, pH 8.1. A viral lysate is generated by three freeze-thaw cycles, cell debris is removed by centrifugation for 10 min. at 2,000 rpm, and the adenovirus is purified by density gradient centrifugation. The adenovirus band is stored at −20° C. in sterile glycerol/BSA until needed.

Figure 10A:
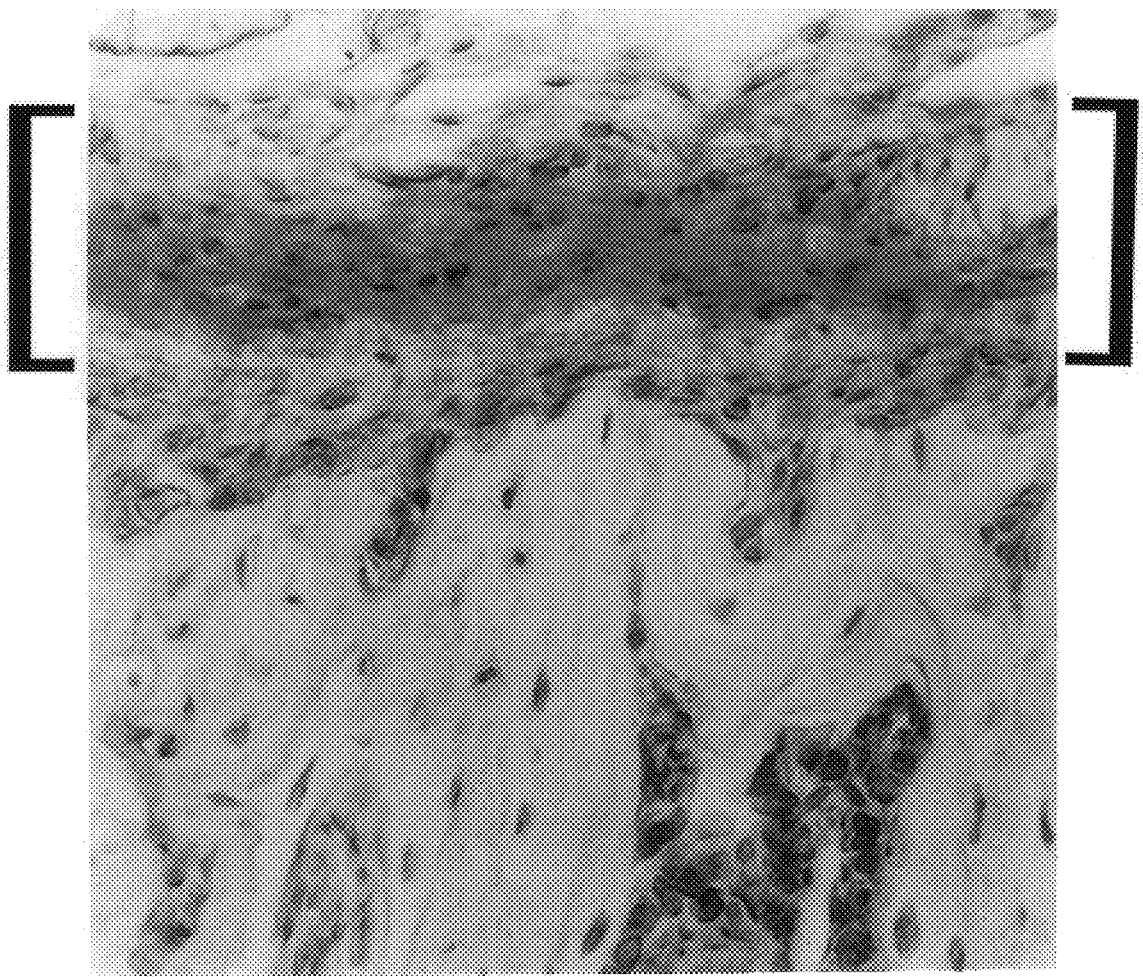
FIG. 10A, FIG. 10B and FIG. 10C. Adenovirus-mediated gene transfer into bone repair/regeneration cells in vivo. The UltraFiber™ implant was soaked for 6 min. in a solution of the AdCMVlacZ virus ($10^{10}$–$10^{11}$ plaque forming units or PFU/ml) and then implanted into the osteotomy site. The defect was allowed to heal for 3 weeks, during which time the progress of the wound healing response was monitored by weekly radiographic examination. By 3 weeks, it was estimated that 40% of the defect was filled with callus tissue. The animal was sacrificed and tissues were fixed in Bouins fixation and then demineralized for 6–8 days using standard formic acid solutions. Photomicrographs were taken from transverse sections of new bone (callus) that formed in the osteotomy site 3 weeks after surgery.
Figure 10B:
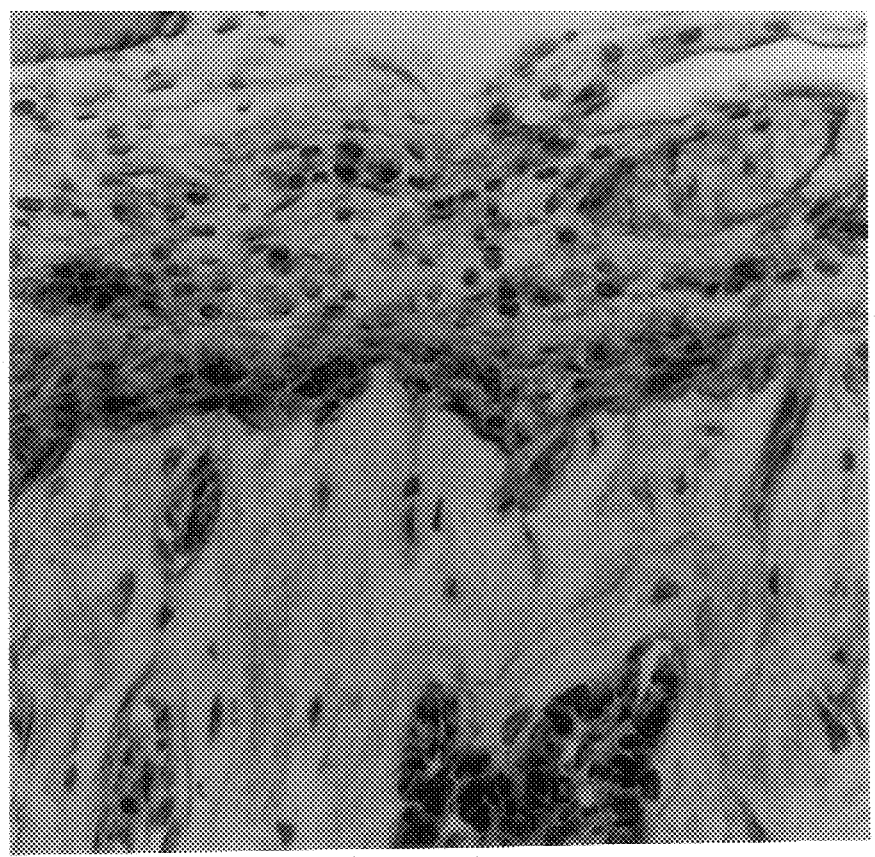
Figure 10C:
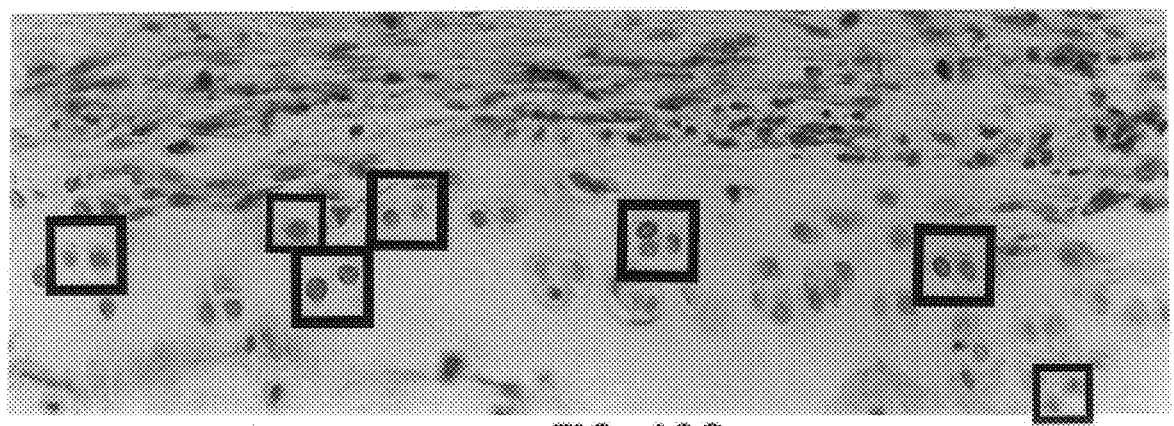

The solution of virus particles was sterilized and incubated with the implant material (from 6 mins to overnight), and the virus-impregnated material was implanted into the osteotomy gap, where viral infection of cells clearly occurred. The results obtained clearly demonstrated the exquisite specificity of the anti-β-gal antibody (Sambrook et al., 1989), and conclusively demonstrated expression of the marker gene product in chondrocyte-like cells of the osteotomy gap (FIG. 10A and FIG. 10C). The nuclear-targeted signal has also been observed in pre-osteoblasts.

EXAMPLE X

Transfer of an Osteotropic Gene Stimulates Bone Regeneration/Repair In Vivo

In order for a parathyroid hormone (PTH) transgene to function as an osteotropic agent, it is likely that there is a requirement for the PTH/PTHrP receptor to be expressed in the bone repair tissue itself. Therefore, the inventors investigated PTH/PTHrP receptor expression in the rat osteotomy model.

Figure 7:
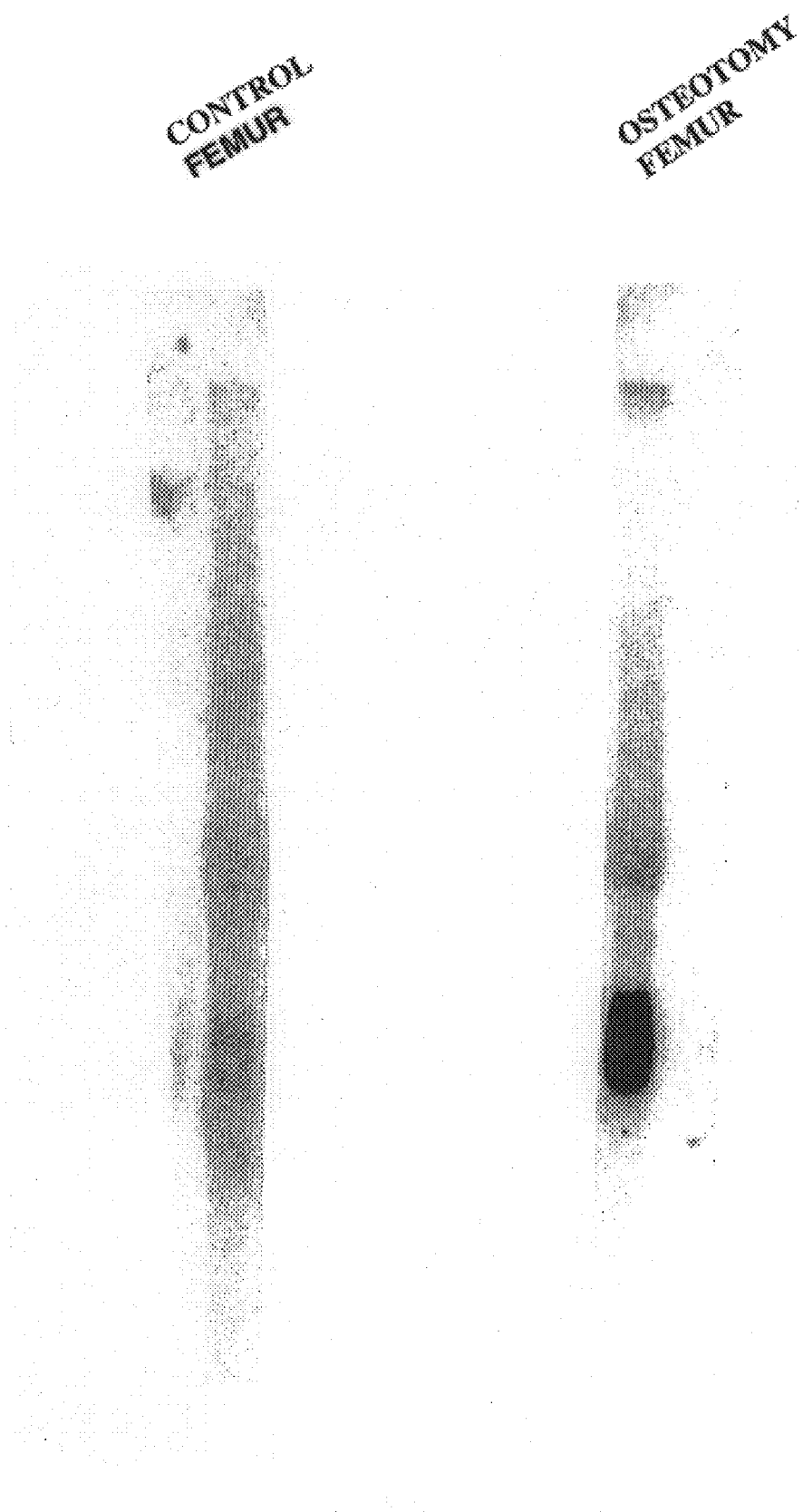
FIG. 7. Northern analysis of poly-A($^+$) RNA demonstrating expression of the PTH/PTHrP receptor in osteotomy repair tissue.

A Northern analysis of poly-A($^+$) RNA was conducted which demonstrated that the PTH/PHTrP receptor was expression in osteotomy repair tissue (FIG. 7).

The inventors next investigated whether gene transfer could be employed to create transfected cells that constitutively express recombinant hPTH1-34 in vivo, and whether this transgene can stimulate bone formation. The rate of new bone formation is analyzed as follows. At necropsy the osteotomy site is carefully dissected for histomorphometric analysis. The A-P and M-L dimensions of the callus tissue are measured using calipers. Specimens are then immersion fixed in Bouins fixative, washed in ethanol, and demineralized in buffered formic acid. Plastic embedding of decalcified materials is used because of the superior dimensional stability of methacrylate during sample preparation and sectioning.

Tissue blocks are dehydrated in increasing alcohol concentrations and embedded. 5 mm thick sections are cut in the coronal plane using a Reichert Polycut microtome. Sections are prepared from midway through the width of the marrow cavity to guard against a sampling bias. Sections for light microscopy are stained using a modified Goldner's trichrome stain, to differentiate bone, osteoid, cartilage, and fibrous tissue. Sections are cover-slipped using Eukitt's mounting medium (Calibrated Instruments, Ardsley, N.Y.). Histomorphometric analyses are performed under brightfield using a Nikon Optiphot Research microscope. Standard point count stereology techniques using a 10 mm×10 mm eyepiece grid reticular are used.

Total callus area is measured at 125× magnification as an index of the overall intensity of the healing reaction. Area fractions of bone, cartilage, and fibrous tissue are measured at 250× magnification to examine the relative contribution of each tissue to callus formation. Since the dimensions of the oste6tomy gap reflect the baseline (time 0), a measurement of bone area at subsequent time intervals is used to indicate the rate of bone infill. Statistical significance is assessed using analysis of variance, with post-hoc comparisons between groups conducted using Tukey's studentized range t test.

Figure 8A:
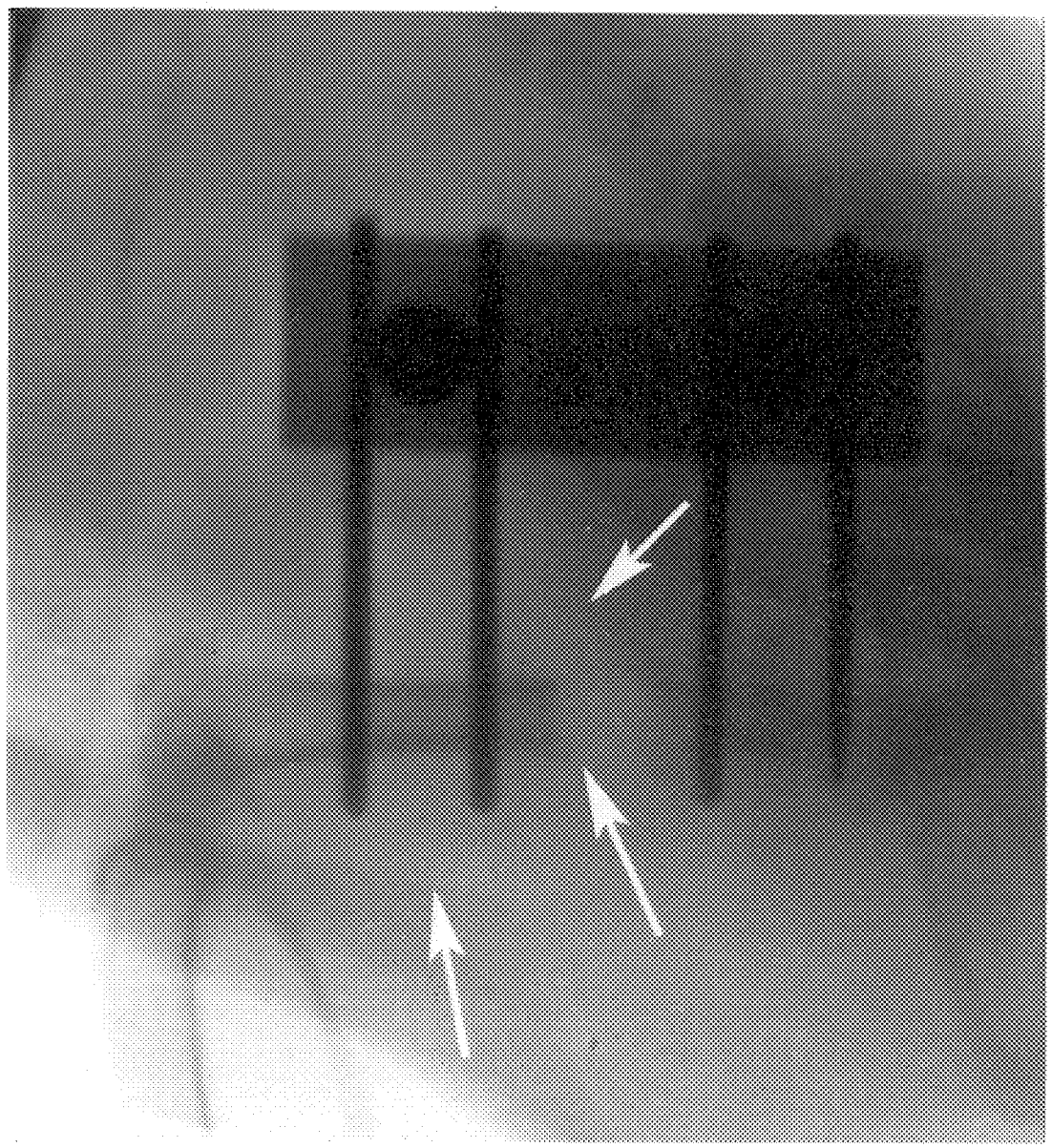
FIG. 8A. Transgene expression is capable of stimulating bone regeneration/repair in vivo.
Figure 8B:
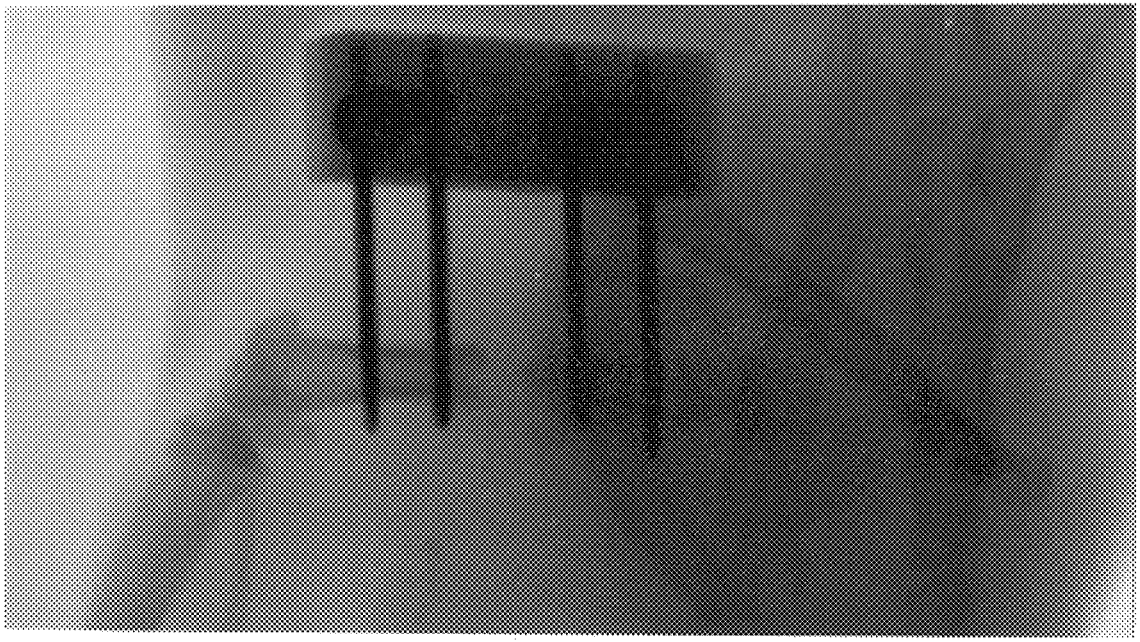
FIG. 8B. Control transgene expression is not capable of stimulating bone regeneration/repair in vivo.

In the 5 mm rat osteotomy model described above, it was found that PTH transgene expression can stimulate bone regeneration/repair in live animals (FIG. 8A and FIG. 8B). This is a particularly important finding as it is known that hPTH1-34 is a more powerful anabolic agent when given intermittently as opposed to continuously, and it is the continuous-type delivery that results from the gene transfer methods used here.

Although the present inventors have already demonstrated success of direct gene transfer into regenerating bone in vivo, the use of ex vivo treatment protocols is also contemplated. In such embodiments, bone progenitor cells would be isolated from a particular animal or human subject and maintained in an in vitro environment. Suitable areas of the body from which to obtain bone progenitor cells are areas such as the bone tissue and fluid surrounding a fracture or other skeletal defect (whether or not this is an artificially created site) and from the bone marrow. Isolated cells would then be contacted with the DNA (or recombinant viral) composition, with, or preferably without, a matrix, when the cells would take up the DNA (or be infected by the recombinant virus). The stimulated cells would then be returned to the site in the animal or patient where bone repair is to be stimulated.

EXAMPLE XI

Transfer of Genes to Achilles' Tendon and to Cruciate Ligament In Vivo

The studies on regenerating bone described above complement others by the inventors in which gene transfer was successfully employed to introduce genes into Achilles' tendon and cruciate ligament.

The Achilles' tendon consist of cells and extracellular matrix organized in a characteristic tissue architecture. Tissue wounding can disrupt this architecture and stimulate a wound healing response. The wounded tendon will regenerate, as opposed to scar, if its connective tissue elements remain approximately intact. Regeneration is advantageous because scar tissue is not optimally designed to support normal mechanical function. Segmental defects in tendon due to traumatic injury may be treated with biological or synthetic implants that encourage neo-tendon formation. This strategy is limited, however, by the availability of effective (autologous) biological grafts, the long term stability and compatibility of synthetic prostheses, and the slow rate of incorporation often observed with both types of implants.

The inventors hypothesized that the effectiveness of biological grafts may be enhanced by the over-expression of molecules that regulate the tissue regeneration response. Toward this end, they developed a model system in which segmental defects in Achilles' tendon are created and a novel biomaterial, small intestinal submucosa or SIS, is used as a tendon implant/molecular delivery agent. In the present example, the ability to deliver and express marker gene constructs into regenerating tendon tissue using the SIS graft is demonstrated.

Plasmid (pSVβgal, Promega) stock solutions were prepared according to standard protocols (Sambrook et al., 1989). SIS graft material was prepared from a segment of jejunum of adult pigs (Badylak et al., 1989). At harvest, mesenteric tissues were removed, the segment was inverted, and the mucosa and superficial submucosa were removed by a mechanical abrasion technique. After returning the segment to its original orientation, the serosa and muscle layers were rinsed, sterilized by treatment with dilute peracetic acid, and stored at 4° C. until use.

Mongrel dogs (all studies) were anesthetized, intubated, placed in right-lateral recumbency upon a heating pad, and maintained with inhalant anesthesia. A lateral incision from the musculotendinous junction to the plantar fascia was used to expose the Achilles' tendon. A double thickness sheet of SIS was wrapped around a central portion of the tendon, both ends were sutured, a 1.5 cm segment of the tendon was removed through a lateral opening in the graft material, and the graft and surgical site were closed. The leg was immobilized for 6 weeks and then used freely for 6 weeks. Graft tissues were harvested at time points indicated below, fixed in Bouins solution, and embedded in paraffin. Tissue sections (8 μm) were cut and used for immunohistochemistry.

In an initial study, SIS material alone (SIS-alone graft) engrafted and promoted the regeneration of Achilles' tendon following the creation of a segmental defect in mongrel dogs as long as 6 months post surgery. The remodeling process involved the rapid formation of granulation tissue and eventual degradation of the graft. Scar tissue did not form, and evidence of immune-mediated rejection was not observed.

In a second study, SIS was soaked in a plasmid DNA solution (SIS+plasmid graft) and subsequently implanted as an Achilles' tendon graft (n=2 dogs) or a cruciate ligament graft (n=2 dogs) in normal mongrel dogs. A pSVβgal plasmid that employs simian virus 40 regulatory sequences to drive β-galactosidase (β-gal) activity was detectable by immunohistochemistry using a specific antibody in 4/4 animals. As a negative control, β-gal activity was not detected in the unoperated Achilles' tendon and cruciate ligament of these animals. It appeared, therefore, that SIS facilitated the uptake and subsequent expression of plasmid DNA by wound healing cells in both tendon and ligament.1

Figure 11A:
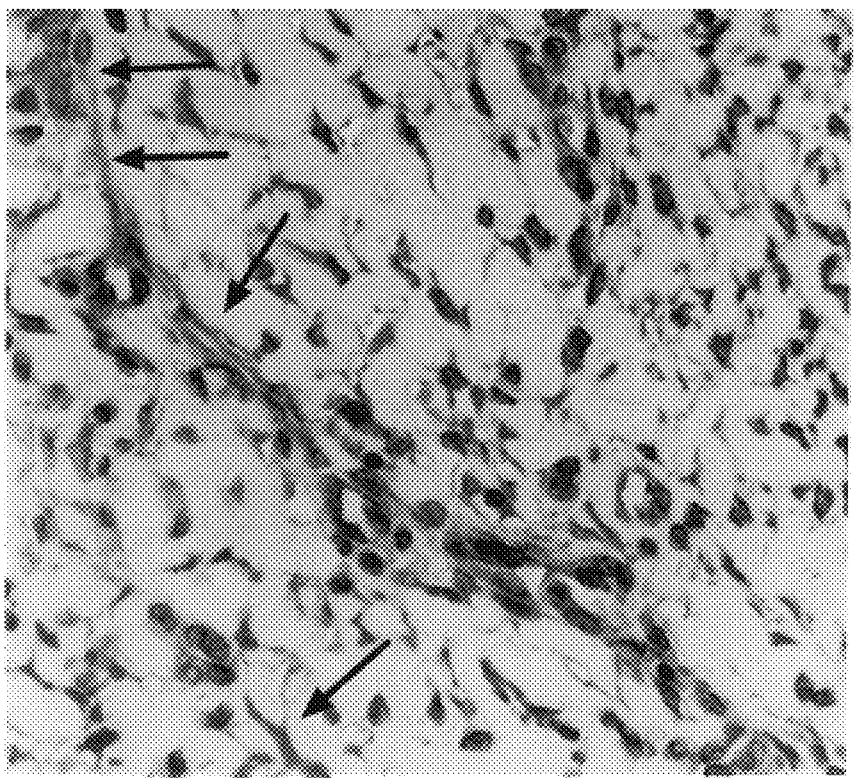
FIG. 11A and FIG. 11B. Direct bacterial βgalactosidase gene transfer into regenerating Achilles' tendon. Cross-section (8 μm) of Bouins fixed, paraffin embedded tissue were cut and mounted on ProbeOn Plus slides (Fisher). Immunohistochemistry was performed according to the protocol provided with the Histostain-SP kit (Zymed).
Figure 11B:
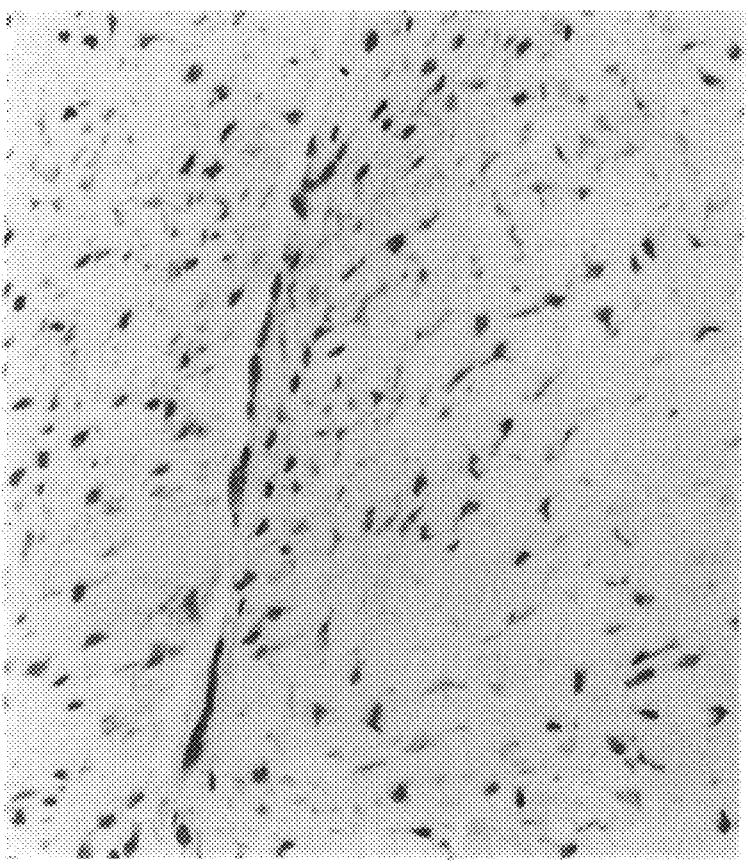

A third study was designed to evaluate the time course of β-gal transgene expression. SIS+plasmid grafts were implanted for 3, 6, 9, and 12 weeks (n=2 dogs pr time point) and transgene expression was assayed by immunohistochemistry (FIG. 11A and FIG. 11B) and by in situ hybridization. Cross-sections (8 μm) of Bouins fixed, paraffin embedded tissue were cut and mounted on ProbeOn Plus slides (Fisher). Immunohistochemistry was performed according to the protocol provided with the Histostain-SP kit (Zymed). In brief, slides were incubated with a well characterized anti-β-galactosidase antibody (1:200 dilution, 5 Prime→3 Prime), washed in PBS, incubated with a biotinylated second antibody, washed, stained with the enzyme conjugate plus a substrate-chromogen mixture, and then counterstained with hematoxylin and eosin.

Bacterial β-gal activity was detected in tendons that received the SIS+plasmid graft (8/8 animals). Although not rigorously quantitative, transgene expression appeared to peak at 9–12 weeks. Bacterial β-gal gene expression was not detected in animals that received SIS-alone grafts (N=2, 3 weeks and 12 weeks). Again, scar tissue did not form and evidence of immune-mediated rejection was not observed.

This study has demonstrated that (i) a novel biomaterial, SIS, can effectively function as an autologous graft which promotes the regeneration of tissues such as Achilles' tendon and anterior cruciate ligament, and (ii) SIS can be used to deliver a marker gene construct to regenerating tissue.

EXAMPLE XIII

Mechanical Properties of New Bone Formation

The mechanical properties of new bone formed during gene transfer may be measured using, e.g., whole bone torsion tests which create a stress state in which the maximum tensile stresses will occur on planes that lie obliquely to the bone's longitudinal axis. Such tests may provide important inferences about the mechanical anisotropy of callus tissue and the degree of osseous integration of new bone tissue. These tests are particularly advantageous in the evaluation of fracture specimens, e.g., the irregular shape of callus tissue typically precludes the use of whole bone 4-point bending tests because it is impossible to reproducibly align the points from specimen to specimen.

Femurs are tested on an MTS Servohydraulic Testing Machine while moist and at room temperature. A torque sensor and rotary variable displacement transduces provides data for torque-angular displacement curves. Specially designed fixtures support each bone near the metaphyseal-diaphyseal junctions, and apply a 2-point load to the diaphysis. Tests are conducted at a constant rate of displacement equal to 20 degrees/sec. A 250 inch-ounce load cell measures the total applied force. All bones are tested while moist and room temperature. Torque and angular displacement data are acquired using an analog-to-digital converter and a Macintosh computer and software. From this data, the following variables are calculated: a) maximum torque, b) torsional stiffness, the slope of the pre-yield portion of the curve determined from a linear regression of the data, c) energy to failure, the area under the torque-angular displacement curve to the point of failure, and d) the angular displacement ratio, the ratio of displacement at failure to displacement at yield. Statistical significance is determined Analysis of Variance followed by multiple comparisons with appropriate corrections (e.g., Bonferroni).

This invention also provides a means of using osteotropic gene transfer in connection with reconstructive surgery and various bone remodelling procedures. The techniques described herein may thus be employed in connection with the technology described by Yasko et al., (1992), Chen et al., (1991) and Beck et al. (1991), each incorporated herein by reference.

EXAMPLE XIV

Identification of Further Osteotropic Genes: Isolation of a Novel Latent TGF-β Binding Protein-Like Gene The extracellular matrix contains a heterogenous population of 3–20 nm filaments termed microfibrils. The inventors recently isolated and characterized the mouse and human genes for several microfibril components and characterized their expression pattern during mouse development. This example concerns the isolation and characterization of a new member of the fibrillin gene family.

A. Methods 1. cDNA Cloning

Aliquots (typically 40–50,000 PFU) of phage particles from a CDNA library in the λZAP II vector made from 3T3 cell mRNA (Stratagene) and fresh overnight XL1-blue cells (grown in Luria broth supplemented with 0.4% maltose in 10 mM MgSO$_4$) were mixed, incubated for 15 min. at 37° C., mixed again with 9 ml of liquid (50° C.) top layer agarose (NZY broth plus 0.75% agarose), and then spread evenly onto a freshly poured 150 mm NZY-agar plate. Standard methods were used for the preparation of plaque-lifts and filter hybridization (42° C., in buffer containing 50% formamide, 5× SSPE, 1× Denhardt's, 0.1% SDS, 100 mg/ml salmon sperm DNA, 100 mg/ml heparin). cDNA probes were radiolabeled by the nick translation method (Sambrook et al., 1989). Purified phage clones were converted to pBluescript plasmid clones, which were sequenced using Sequenase™ (version 2.0) as described (Chen et al., 1993).

2. Polymerase Chain Reaction

Poly($A^+$) RNA was prepared from mouse embryo and rat tissues as indicated using commercially available reagents (Fast Track™, Invitrogen). cDNA synthesis was performed as described (cDNA Synthesis System Plus kit protocol, Amersham), except that the reverse transcriptase enzyme was purchased separately (Seikagaku). Aliquots of cDNA (~10%) were PCR™ amplified using commercially available reagents (Perkin Elmer-Cetus). Amplification proceeded through 30 cycles of denaturation, annealing, and elongation. The annealing temperature of the reaction was determined by the equation $4(G+C)+2(A+T)-6=T_A$ (Chen et al., 1993).

3. Northern Analysis

Poly($A^+$) RNA (2–10 μg aliquots) was electrophoresed on a 1.25% agarose/2.2M formaldehyde gel and then transferred to a nylon membrane (Hybond-N, Amersham). The RNA was cross-linked to the membrane by exposure to a UV light source ($1.2 \times 10^6$ mJ/cm$^2$, UV Stratalinker 2400, Stratagene) and then prehybridized for >15 min. at 65° C. in Rapid-Hyb buffer (Amersham, Inc.). Specific CDNA probes were $^{32}$P-labeled by random priming and used for hybridization (2 h at 65° C.). Blots were washed progressively to high stringency (0.1× SSC/0.1% SDS, 65° C.), and then placed against x-ray film with intensifying screens (X-OMAT XAR, Eastman Kodak, Inc.) at −86° C.

4. Isolation and Sequencing of a Mouse Genomic Clone

A genomic library in the Lambda Fix II vector (made from mouse strain SV129 liver DNA, Stratagene, Inc.) was plated at ~60,000 plaques/plate, and nitrocellulose replicas were screened at high stringency (42° C., in buffer containing 50% formamide, 5× SSPE, 1× Denhardt's, 0.1% SDS, 100 mg/ml salmon sperm DNA, 100 mg/ml heparin) using a 2770 bp cDNA fragment as the probe (derived from clone "#18",). Filters were washed in 0.1× SSPE+0.1% SDS at 42° C. and autoradiographed. Duplicate positive plaques from one independent clone (WY-G-1-1) were re-screened until purified, and DNA was prepared as described in the Magic Lambda Prep kit protocol (Promega, Inc.). The insert consisted of >10 kb of genomic DNA. BamHI digestion of the phage clone yielded several DNA fragments that could be resolved by agarose gel electrophoresis, and all of these were subcloned into BamHI-digested pGEM3Z (Promega, Inc.). Selected regions of the subcloned insert were sequenced as described above to verify the nature of the clone.

5. Isolation and Sequencing of a Human Genomic Clone

A human genomic library (Lambda EMBL3 EcoRI) was plated at ~40,000 plaques/plate, and nitrocellulose replicas were screened at moderate stringency (as described above) using a 3.8 kb mouse cDNA fragment as the probe (clone "#18",). Filters were washed in 1× SSC+0.1% SDS at 48° C. and autoradiographed. Duplicate positive plaques from one independent clone (ES-C) were re-screened until purified, and DNA was prepared as described in the Magic Lambda Prep kit protocol (Promega). BamHI digestion of the purified phage clone yielded a single 4.0 kb DNA fragment that could be resolved by Southern analysis. This fragment was then cut with SmaI, a 872 bp BamHI-SmaI fragment was subcloned into pGEM7Z (Promega), and selected regions of the subcloned insert were sequenced as described above to verify the nature of the clone.

6. Tissue In Situ Hybridization

To prepare sense and antisense probes, a 382 bp fragment from the 3' untranslated region (+3753 to +4134, counting the "A" of the initiator Met codon as +1; see FIG. 14, clone "ish") was subcloned into the pBluescript KS+ plasmid (Stratagene, Inc.). Template DNA was linearized with either EcoRI or BamHI, extracted, and precipitated with ethanol. Sense and antisense transcripts were generated from 1 μg template with T3 and T7 polymerases in the presence of [$^{35}$S]UTP at >6 mCi/ml (Amersham, >1200 Ci/mmol) and 1.6 U/ml RNasin (Promega), with the remaining in vitro transcription reagents provided in a kit (SureSite, Novagen, Inc.). After transcription at 37° C. for 1 h, DNA templates were removed by a 15 min. digest at 37° C. with 0.5 U/ml RNase-free DNase I, extracted, and precipitated with ethanol. Riboprobes were hydrolyzed to an average final length of 150 bp by incubating in 40 mM NaHCO$_3$, 60 mM Na$_2$CO$_3$, 80 mM DTT for 40 min. at 60° C. Hydrolysis was terminated by addition of sodium acetate, pH 6.0, and glacial acetic acid to 0.09M and 0.56% (vol./vol.), respectively, and the probes were then ethanol precipitated, dissolved in 0.1M DTT, counted, and stored at 20° C. until use. Day 8.5–9.0, day 13.5, and day 16.5 mouse embryo tissue sections (Novagen) and the in situ hybridization protocol were employed as described (Chen et al., 1993).

B. Results

Microfibrils 10 nm in diameter assist in elastic fiber assembly, serve an anchoring function in non-elastic tissues, and play a role in tissue remodeling. Consistent with a possible role in wound healing, it was found that the new fibrillin gene is expressed as alternatively spliced transcripts in fracture tissue.

Figure 12A:
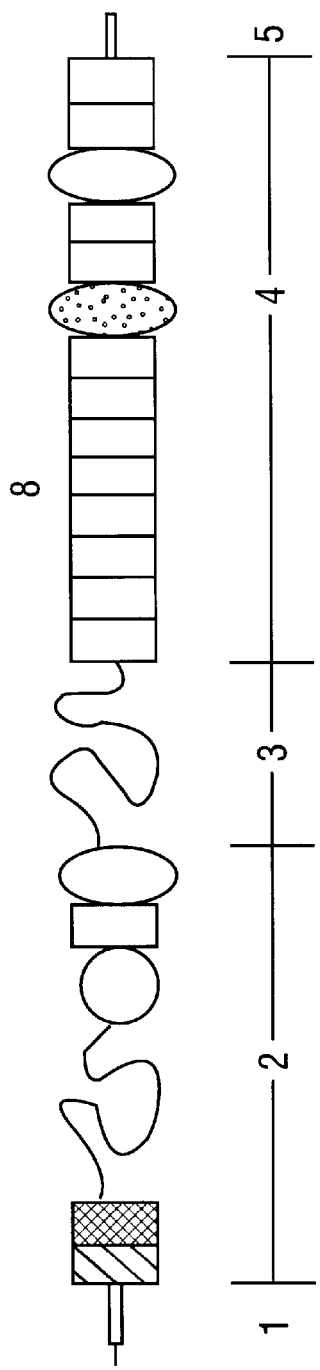
FIG. 12A. A schematic showing the structure of the mouse LTBP-like molecule. Domains #1–5 are denoted below the diagram. Symbols designate the following structural elements: EGF-CB repeats—open rectangles; TGF-bp repeats—open ovals; Fib motif—open circle; TGF-bp-like repeat—patterned oval; cysteine-rich sequences—patterned rectangles; proline/glycine-rich region—thick curved line, domain #2; proline-rich region—thick curved line, domain #3. Note that symbols designating the signal peptide have been deleted for simplicity. Additionally, the schematic assumes that EGF-like and EGF-CB repeats may extend for several amino acids beyond the $C_6$ position.

In this study, the inventors isolated and characterized a novel mouse fibrillin-like cDNA. It provides a unique mRNA of 4,314 nucleotides, with an open reading frame of 3,756 nucleotides (SEQ ID NO:2). The deduced molecule is a unique polypeptide of 1,252 amino acids (SEQ ID NO:3). Excluding the signal peptide (est. 18 amino acids), the novel fibrillin-like molecule consists of five structurally distinct regions (A–E), a schematic representation of the domain structure of the new sequence is shown in FIG. 12A. The largest region (region D) extends for 635 amino acids and comprises an uninterrupted series of 12 cysteine-rich repeats. Based on structural homologies, this sequence includes ten epidermal growth factor-calcium binding repeats and two transforming growth factor-β1-binding protein repeats.

Figure 12B:
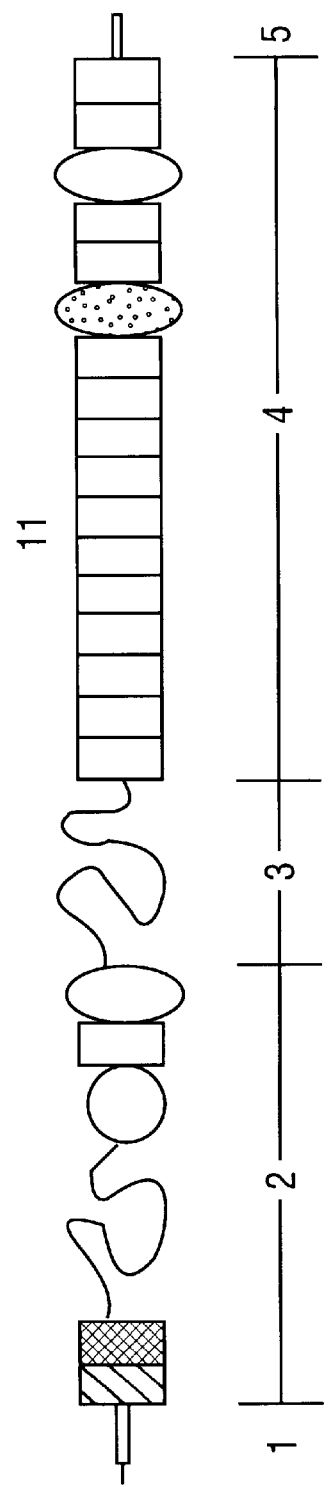
FIG. 12B. A schematic showing the structure of human LTBP (B). Domains #1–5 are denoted below the diagram. The symbols designating the structural elements are defined in the legend to FIG. 12A.
Figure 13A:
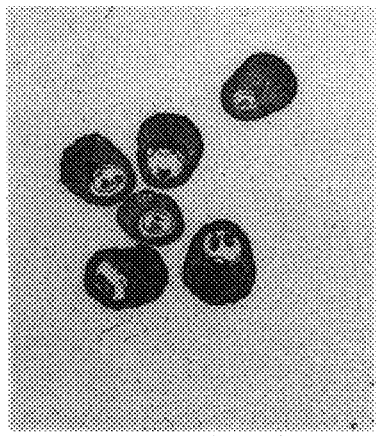
FIG. 13A, FIG. 13B, FIG. 13C, FIG. 13D, FIG. 13E and FIG. 13F, Overview of expression of the new LTBP-like gene during murine development as determined by tissue in situ hybridization.
Figure 13B:
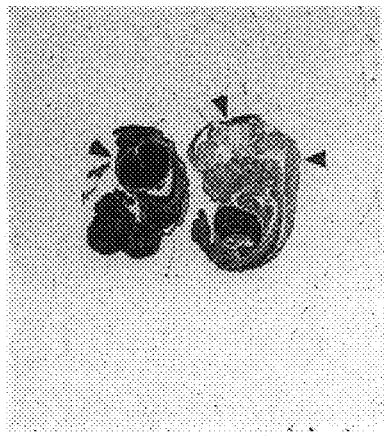
Figure 13C:
Figure 13D:
Figure 13E:
Figure 13F:

A second cysteine-rich region (region B), more near the amino terminus, spans 392 amino acids. Between the two cysteine-rich regions is a 154 amino acid segment (region C) that has a high proline content (21%). The last two predicted regions of the novel fibrillin are a 22 amino acid carboxy-terminus (region E) and a 31 amino acid stretch at the amino-terminus (region A). Northern blot analysis of mouse embryo RNA agrees with the deduced size of the transcript, showing a single band of 4.5–5.0 kb. The corresponding schematic of the human LTBP is shown in FIG. 12B.

The first indication of alternative splicing came from molecular cloning studies in the mouse, in which independent cDNA clones were isolated with a deletion of 51 bp from the coding sequence. PCR/Southern blot analysis provided additional evidence that the homologous 51 bp sequence was alternatively spliced in normal mouse embryo tissues.

Northern blot analysis demonstrated that the novel fibrillin gene was also expressed in rat callus three weeks after osteotomy, after mineralization has begun. Gene expression in normal adult rat bone tissue was insignificant, which suggests that microfibrils are an important part of the bone fracture healing response. The novel fibrillin-like gene was expressed in callus as a pair of alternatively spliced transcripts. This result has been independently reproduced on three occasions. Molecular cloning of the novel fibrillin gene in both mouse and rat has identified potential splice junction sites for the alternative splicing event.

This new fibrillin-like gene is present in both the mouse and rat, and is expressed in callus tissue as a pair of alternatively spliced transcripts. This is the first evidence that fibrillin-associated microfibrils are present in the extracellular matrix of callus.

This new fibrillin gene is expressed during mouse development. The transcript is widely expressed in connective tissue and mesenchyme (FIG. 13A, FIG. 13B, FIG. 13C, FIG. 13D, FIG. 13E and FIG. 13F.), it is also expressed in liver, heart and CNS tissues.

As part of a study designed to clone the mouse fibrillin-1 gene, cDNA from a 3T3 cell cDNA library was amplified using human fibrillin-1 PCR™ primers under low stringency conditions (i.e. annealing at 37° C. initially for 10 cycles, followed by annealing at 60° C. for 30 cycles). The initial results were surprising in that a mouse DNA fragment of unexpectedly low homology (~50%) to human fibrillin-1 was obtained. Molecular cloning of the authentic mouse fibrillin-1 transcript was eventually completed, and this study confirmed that the human and mouse fibrillin-1 coding sequences share >95% sequence identity (Yin et al., submitted for publication). The mouse fibrillin-1 and PCR™ sequences were different, which suggested that the PCR™ product may have been derived from a related, fibrillin-like cDNA. The 3T3 cell CDNA library was screened at high stringency using the mouse PCR™ product as the probe in order to test this hypothesis. A cDNA walking strategy eventually yielded seven overlapping cDNA clones (clone no. 3 extending from −156 to +1,055; clone no. 19 extending from +200 to +1643; clone no. 18–5 extending from +200 to +3195; clone no. B extending from +1759 to +3236; clone no. A extending from +3231 to +4035; clone ish extending from +3973 to +4314; clone no. 18 extending from +498 to +4289; the numbering system assumes that the "A" of the initiator Met codon is nucleotide No. 1.) which coded a unique transcript of 4.6 kb (SEQ ID NO:2) and a polypeptide of 1,252 amino acids (SEQ ID NO:3).

Sequence analysis of these clones revealed an open reading frame of 3,753 nt. A methionine codon in a favorable context for translation initiation was provisionally designated +1. The initiator methionine was followed by a characteristic signal sequence of 21 amino acids (von Heijne, 1986). Beyond this, the conceptual amino acid sequence appeared to be organized into five structurally distinct domains (#–5). Domain #1 is a 28 amino acid segment with a net basic charge (est. pI, 12.36) that may allow for binding acidic molecules in the extracellular matrix (e.g., acidic proteoglycans). Sequences rich in basic amino acids may also function as endoproteolytic processing signals (Barr, 1991; Steiner et al., 1992), which suggests that the $NH_2$-terminus may be proteolytically processed. Domain #2 extends for of 390 amino acids, consisting of an EGF-like repeat, a 135 amino acid segment that was proline-rich (20.7%) and glycine-rich (11.8%) but not cysteine-rich, a Fibmotif (Pereira et al., 1993), an EGF-CB repeat, and a TGF-bp repeat. Domain #3 is a 113 amino acid segment characterized by its high proline content (21%). Domain #4 extends for 678 amino acids and consists of 14 consecutive cysteine-rich repeats. Based on structural homologies, 12/14 repeats were epidermal growth factor-calcium binding (EGF-CB) motifs (Handford et al., 1991), whereas 2/14 were transforming growth factor-β-binding protein (TGF-bp) motifs (Kanzaki et al., 1990). Finally, domain #5 is a 22 amino acid segment at the carboxy-terminus.

The conceptual amino acid sequence encoded by the open reading frame consisted of 1,252 amino acids (FIG. 12A) with an estimated pI of 5.92, a predicted molecular mass of 134,710 Da, and five potential N-linked glycosylation sites. No RGD sequence was present. Northern blot analysis of mouse embryo RNA using a 3' untranslated region probe identified a transcript band of ~4.6 kb. In this regard, 4,310 nt have been isolated by cDNA cloning, including a 3' untranslated region of 401 nt and a 5' upstream sequence of 156 not. The apparent discrepancy between the Northern analysis result and the cDNA sequence analysis suggested that the t' upstream sequence may include ~300 nt of additional upstream sequence. This estimate was consistent with preliminary primer extension mapping studies indicating that the 5' upstream sequence is 400–500 nt in length.

A total of 19 cysteine-rich repeats were found in domains #2 and #4 of the mouse LTBP-like polypeptide. Thirteen were EGF-like and 11/13 contained the calcium binding consensus sequence. This consensus was derived from an analysis of 154 EGF-CB repeats in 23 different proteins and from structural analyses of the EGF-CB repeat, both bound and unbound to calcium ion (Selander-Sunnerhagen et al., 1992). Variations on the consensus have been noted previously and one of these, $D-L-N/D-E-C_1$, was identified in the third EGF-like repeat of domain #4. In addition, a potential calcium binding sequence which has not previously been reported ($E-T-N/D-E-C_1$) was identified in the first EGF-like repeat of domain #4. Ten of thirteen EGF-CB repeats also contained a second consensus sequence which represents a recognition sequence for an Asp/Asn hydroxylase that co-and posttranslationally modifies D/N residues (Stenflo et al., 1987; Gronke et al., 1989).

Although about one-half the size, the deduced polypeptide was organized like fibrillin-1 in that it consisted of a signal peptide followed by 5 structurally distinct domains, i.e. two domains with numerous EGF-like, EGF-CB and Fib repeats and a third with a proline-rich sequence (Pereira et al., 1993). However, comparison of each of these domains using the GAP and BESTFIT programs (Genetics Computer Group) has revealed a low level of amino acid homology of only 27% over the five structural domains shared by the deduced mouse polypeptide and human fibrillin-2. These values are low for a putative fibrillin family member because fibrillin-1 and fibrillin-2 share ~50% identity (zhang et al., 1994).

A search of available databases revealed that the deduced mouse polypeptide was most similar to the human and rat latent TGF-β binding proteins (Kanzaki et al., 1990; Tsuji et al., 1990). In this regard LTBP was found to be similar to fibrillin in that it could also be divided into five structurally distinct domains (FIG. 12A and FIG. 12B). These include a relatively short domain downstream of the signal peptide with a net basic charge (amino acids 21–33, est. pI, 11.14); a domain consisting of EGF-like, EGF-CB, TGF-bp, and Fib motifs plus a proline-rich and glycine-rich sequence (amino acids 34–407); a proline-rich domain (amino acids 408–545); a large, domain consisting of EGF-CB, TGF-bp, and TGF-bp-like repeat motifs (amino acids 546–1379); and a relatively short domain at the carboxy terminus (amino acids 1380–1394). Amino acid sequence comparison of the deduced mouse and human polypeptides shows 60% identity for domain #1, 52% identity for domain #2, 30% identity for domain #3, 43% identity for domain #4, and 7% identity for domain #5. The average identity over the five domains shared by the mouse polypeptide and human LTBP was 38.4%. Significantly, cysteine residues in both polypeptide sequences were highly conserved.

The fibrillins are exclusively expressed by connective cells in developing tissues (zhang et al., 1994), whereas LTBP should be expressed along with TGF-β by both epithelial and connective cells (Tsuji et al., 1990). The structural homology data therefore predict that the mouse gene shown in FIG. 12A should be expressed by both epithelial and connective tissue cells. Tissue in situ hybridization was used to test this hypothesis.

An overview of the expression pattern as determined by tissue in situ hybridization is presented in FIG. 13A, FIG. 13B, FIG. 13C, FIG. 13D, FIG. 13E and FIG. 13F. Approximate mid-sagittal sections of normal mouse embryos at days 8.5–9.0, 13.5 and 16.5 p.c. of development were hybridized with a $^{35}$S-labeled single stranded normal sense riboprobe from the same cDNA construct was used. At day 8.5–9.0 of development, intense gene expression was observed in the mesometrial and antimesometrial uterine tissues, ectoplacental cone, placenta, placental membranes. The transcript appeared to be widely expressed in mouse embryo mesenchymal/connective tissue compartments, including the facial mesenchyme, at days 8.5–9.0, 13.5 and 16.5 of development. Particularly intense expression of the transcript was noted in the liver.

Microscopy of day 8.5–9.0 embryos confirmed the widespread expression of the mouse gene by mesenchymal cells. Significant expression of the transcript by cells of the developing central nervous system, somites and cardiovascular tissue (myocardium plus endocardium) was also observed.

Microscopy of day 13.5 and day 16.5 embryos demonstrated expression of the mouse gene by skeletal muscle cells and by cells involved in intramembranous and endochondral bone formation. The transcript was expressed by osteoblasts and by periosteal cells of the calvarium, mandible and maxilla. The transcript was also identified in both cartilage and bone of the lower extremity. A positive signal was detected in perichondrial cells and chondrocytes (proliferating>mature>hypertrophic) of articular cartilage, the presumptive growth plate, and the cartilage model within the central canal. The positive signal was also expressed by blood vessel endothelial cells within the mid-diaphysis.

Respiratory epithelial cells lining developing small airways and connective tissue cells in the pulmonary interstitium expressed the mouse transcript, as did myocardial cells (atria and ventricles) and endocardial cushion tissue. Cells within the walls of large arteries also expressed the transcript. Expression of the mouse gene was identified in several organs of the alimentary system, including the tongue, esophagus, stomach, small and large intestine, pancreas and liver. Mucosal epithelial cells lining the upper and lower digestive tract plus the smooth muscle and connective tissue cells found in the submucosa expressed the transcript, as did acinar cells of the exocrine pancreas. Despite the high level of transcript expression in the liver, these results suggest both cell populations express the LTBP-like transcript.

In the kidney, expression above the basal level was observed in cells of developing nephrons, the ureteric bud, kidney blastema and the kidney interstitium. In the skin, epidermal and adnexal keratinocytes, dermal connective tissue cells, and brown fat cells within the dorsal subcutis expressed the mouse transcript. In the central and peripheral nervous systems, ganglion cells within the cerebrum, brainstem, spinal cord, and peripheral nerves expressed the mouse transcript. The transcript was also intensely expressed by cells of the developing mouse retina.

Thus, the mouse gene is widely expressed by both epithelial and connective tissue cells, a pattern that would be expected for a latent TGF-β binding protein. Three final observations argue that the LTBP-like sequence presented in FIG. 12A is not simply the mouse homologue of human LTBP. First, domain #4 of the mouse LTBP-like sequence has a smaller number of EGF-like repeat motifs than human and rat LTBP (8 versus 11). Second, portions of the human and rat LTBP-like coding sequence were characterized and found to share ~90% identity with human and rat LTBP but only 65% identity with the mouse LTBP-like gene. The first and second observations came from studies using oligonucleotide primers from rat LTBP to amplify mouse embryo cDNA to generate a single 311 bp PCR™ product. Primer sequences were as follows:

(upstream, outer), ATGCCTAAACTCTACCAGCACG (SEQ ID NO: 7);
(upstream, inner) GAGTCACGTCATCCATTCCACA (SEQ ID NO: 8);
(downstream), CGTCCAAGTTGTGTCTTAGCAG (SEQ ID NO: 9); and the fragment of mouse LTBP was generated by PCRTM as described previously. Third, the human LTBP and LTBP-like genes are localized to separate chromosomes. Human LTBP was assigned to human chromosome 2 based on the analysis of human x rodent somatic cell hybrid lines (Stenman et al., 1994). To our knowledge, no LTBP gene has been mapped in the mouse. The human LTBP-like genes was recently localized to chromosome 11 band q12, while the mouse gene was mapped to mouse chromosome 19, band B (a region of conserved synteny), using several independent approaches.

C. Discussion

This study reports the molecular cloning of a novel LTBP-like gene that contains numerous EGF-like repeats. Northern analysis indicates that the gene encodes a single transcript of ~4.6 kb in mouse embryo tissues. The deduced amino acid sequence of the mouse gene product appears to be a secreted polypeptide of 1,251 amino acids. Although it is similar to fibrillin, the overall structural organization and expression pattern of this gene product most resembles LTBP, a latent TGF-β binding protein that was originally isolated and characterized by Heldin and co-workers (see Kanzaki et al., 1990). Several observations strongly suggest that LTBP and the mouse LTBP-like gene product are therefore derived from related but distinct genetic loci. First, LTBP and the LTBP-like coding sequence share ~40% identity and differences exist in the number of EGF-CB repeats in the deduced polypeptide sequence of the two molecules. Second, a portion of the mouse LTBP gene has been cloned and shown to share ~90% identity with human and rat LTBP. Conversely, portions of the human and rat LTBP-like genes have been cloned and shown to share ~90% identity with the mouse LTBP-like gene. Third, LTBP and the LTBP-like gene reside on different human chromosomes (Stenman et al., 1994). Taken together, these data suggest that a family of at least two LTBP genes exists.

Similarities in the structural organization of LTBP-1 and the fibrillin-1 and fibrillin-2 polypeptides have been noted previously (Pereira et al., 1993; Zhang et al., 1994; Taipale et al., 1994). For example, LTBP-1 and the fibrillins are all secreted extracellular matrix constituents. Moreover, each polypeptide can be organized into five domains, two of which consists predominantly of EGF-CB and TGF-bp repeat motifs. LTBP-1 and fibrillin-1 also share a domain that is proline-rich, and LTBP possesses an 8-cysteine repeat previously referred to as the "Fib motif" because it was assumed to be unique to fibrillin (Pereira et al., 1993). These similarities likely explain the initial isolation and cloning of the LTBP-2 PCR™ product, especially since the human oligonucleotide primers used to initially amplify mouse cDNA were designed to direct the synthesis of an EGF-CB repeat in domain #4.

Another point of distinction between LTBP-2 and fibrillin concerns the spacing of conserved cysteines C4 and C5 in EGF-like repeats. Fibrillin-1 and fibrillin-2 each contain >50 such repeats, and in every one the spacing is $C_4$-X-$C_5$. While this pattern is repeated in a majority of the EGF-like repeats in LTBP-1 and LTBP-2, both genes also contain repeats with the spacing $C_4$-X-X-$C_5$. Although the significance of this observation is unclear, variation in the number of amino acids between $C_4$ and $C_5$ would not be expected to alter the function of the EGF-like repeat. Mature EGF is a 48 amino acid secreted polypeptide consisting of two subdomains that have few interdomain contacts (Engel, 1989; Davis, 1990). The larger $NH_2$-terminal subdomain consists of residues 1–32 and is stabilized by a pair of disulfide bonds ($C_1$–$C_3$ and $C_2$–$C_4$), whereas the smaller COOH-terminal subdomain (amino acids 33–48) is stabilized by a single disulfide bond ($C_5$–$C_6$). The COOH-terminal subdomain has a highly conserved conformation that only is possible if certain residues and the distances between them are well conserved, while conformation-sequence requirements for the NH2-terminal subdomain are relatively relaxed. Variation in $C_4$–$C_5$ spacing would not be expected to alter conformation because these residues do not normally form a disulfide bond and the spacing variation occurs at the interface of subdomains that would not be predicted to interact. The cloning of additional genes will decide whether variation in $C_4$–$C_5$ spacing is a reliable discriminator between members of the LTBP and fibrillin gene families.

The LTBP-2 gene is expressed more widely during development than fibrillin-1 or fibrillin-2. Studies in developing mouse tissues have shown that the Fbn-1 gene is expressed by mesenchymal cells of developing connective tissue, whereas the mouse LTBP-like gene is intensely expressed by epithelial, parenchymal and stromal cells. Earlier reports have suggested that TGF-β plays a role in differentiation and morphogenesis during mouse development (Lyons and Moses, 1990), when TGF-β is produced by epithelial, parenchymal and stromal cells. Tsuji et al. (1990) and others have suggested that the expression of TGF-β binding proteins should mirror that of TGF-β0 itself; the expression pattern of the LTBP-2 gene over the course of murine development is consistent with this expectation. However, the LTBP-2 gene may not be completely co-regulated with TGF-β. TGF-β gene and protein expression during mouse development has been surveyed extensively (Heine et al., 1987; Lehnert and Akhurst, 1988; Pelton et al., 1989; Pelton et al., 1990a and b; Millan et al., 1991); these studies have not identified expression by skeletal muscle cells, chondrocytes, hepatocytes, ganglion cells, mucosal cells lining the gut, and epithelial cells of developing nephrons. It is conceivable that the LTBP-2 molecule has an additional function in certain connective tissues besides targeting TGF-β.

The binding properties of the LTBP-2 gene product are under investigation. Formally, the LTBP-2 polypeptide may bind a specific TGF-β isoform, another member of the TGF-β superfamily (e.g., a bone morphogenetic protein, inhibin, activin, or Mullerian inhibiting factor), or a growth factor unrelated to TGF-β. Anti-peptide antibodies to the mouse LTBP-2 polypeptide have been generated and osteoblast cell lines that express the molecule at relatively high levels have been identified. Studies with these reagents suggest that LTBP-2 assembles intracellularly into large latent complexes with a growth factor that is being characterized by immunological methods.

The presence of dibasic amino acids in the LTBP-2 sequence suggests that it may undergo cell- and tissue-specific proteolysis. TGF-β regulates extracellular matrix production by suppressing matrix degradation (through a decrease in the expression of proteases such as collagenase, plasminogen activator, and stromelysin plus an increase in the expression of proteinase inhibitors such as plasminogen activator inhibitor-1 and tissue inhibitor of metalloproteinase-1) and by stimulating matrix macromolecule synthesis (for recent review, see Lyons and Moses, 1990; Massague, 1990; Laiho and Keski-Oja, 1992; and Miyazono et al., 1993). Conversely, production of extracellular matrix has been shown to down regulate TGF-β gene expression (Streuli et al., 1993). TGF-β may therefore regulate extracellular matrix production through a sophisticated feedback loop that influences the expression of a relatively large number of genes. LTBP-1 and LTBP-2 may contribute to this regulation by facilitating the assembly and secretion of large latent growth factor complexes and then targeting the complex to specific connective tissues (Taipale et al., 1994).

EXAMPLE XV

Type II Collagen Promotes New Bone Growth

Certain matrix materials are capable of stimulating at least some new growth in their own right, i.e., are "osteoconductive materials". Potential examples of such materials are well known in the field of orthopedic research and include preparations of hydroxyapatite; preparations of crushed bone and mineralized collagen; polymers of polylactic acid and polyannhydride. The ability of these materials to stimulate new bone formation distinguishes them from inert implant materials such as methylcellulose, which have in the past been used to deliver BMPs to sites of fracture repair.

This Example relates to a study using the rat osteotomy model with implants made of collagen type I (Sigma), collagen type II (Sigma), SIS (small intestinal submucosa), and UltraFiber™ (Norian Corp.). These materials have been placed in situ without DNA of any type. Five animals received an osteotomy with 10 mg of a type II collagen implant alone (10 mg refers to the original quantity of lyophilized collagen). Five of five control animals received an osteotomy with 10 mg of a type I collagen implant alone. Animals were housed for three weeks after surgery and then sacrificed.

The results of these studies were that SIS appeared to retard new bone formation; type I collagen incited a moderately intense inflammatory response; and UltraFiber™ acted as an osteoconductive agent. The type II collagen implant studies yielded surprising results in that 10 mg of this collagen was found to promote new bone formation in the 5 mm osteotomy model. New bone—bridging the osteotomy gap—was identified three weeks after surgery in 5/5 animals that received a type II collagen implant alone (i.e. minus DNA of any type). In contrast, fibrous granulation tissue, but no evidence of new bone formation, was obtained in 5/5 animals receiving a type I collagen implant alone.

Radiographic analysis demonstrated conclusively that all animals receiving an osteotomy with a type II collagen implant without exception showed radio-dense material in the osteotomy gap. In sharp contrast, radiographic analysis of all animals receiving a type I collagen implant revealed no radio-dense material forming in the osteotomy gap. New bone growth is formed in the osteotomy gap of type II collagen implanted-animals. No such new bone growth was observed in the animals receiving type I collagen implants (all animals were examined three weeks after surgery).

The results of the ostetomy with a type II collagen implant resulted in areas of new bone formed in the osteotomy gap using histological analysis. In contrast, only fibrous granulation tissue was identified in the type I collagen gap.

Previous studies have suggested that type II collagen plays only a structural role in the extracellular matrix. The results of the type II collagen implant studies are interesting because they demonstrate a novel and osteoconductive role for type II collagen during endochondral bone repair. To further optimize the osteoconductive potential of type II collagen, a yeast expression vector that encodes for type II collagen (full length α1 (II) collagen) will be employed to produce recombinant α1 (II) collagen protein.

EXAMPLE XIV

Expression of Recombinant Type II Collagen

The Pichia Expression Kit (Invitrogen, Inc.) may be used to prepare recombinant type II collagen. This kit, based on the methylotrophic yeast, *Pichia pastoris*, allows high-level expression of recombinant protein in an easy-to-use relatively inexpensive system. In the absence of the preferred carbon source, glucose, *P. pastoris* utilizes methanol as a carbon source. The AOX1 promoter controls the gene that codes for the expression of the enzyme alcohol oxidase, which catalyzes the first step in the metabolism of methanol. This promoter, which is induced by methanol, has been characterized and incorporated into a series of Pichia expression vectors. This feature of Pichia has been exploited to express high levels of recombinant proteins often in the range of grams per liter. Because it is eukaryotic, *P. pastoris* utilizes posttranslational modification pathways that are similar to those used by mammalian cells. This implies that the recombinant type II collagen will be glycosylated and will contain disulfide bonds.

The inventors contemplate the following particular elements to be useful in the expression of recombinant type II collagen: the DNA sequence of human type II collagen (SEQ ID NO:11) (Lee et al., 1989); rat type II collagen (SEQ ID NO:13) (Michaelson, et al., 1994); and/or mouse type II collagen (SEQ ID NO:15) (Ortman, et al., 1994). As other sources of DNA sequences encoding type II collagen are available, these three are examples of many sequence elements that may be useful in the present invention.

For preparation of a recombinant type II collagen, the native type II collagen cDNA is modified by the addition of a commercially available epitope tag (the HA epitope, Pharmacia, LKB Biotechnology, Inc.). Such fragments may be readily prepared by, for example, directly synthesizing the fragment by chemical means, by application of nucleic acid reproduction technology, such as the PCR technology of U.S. Pat. No. 4,603,102 (herein incorporated by reference) or by introducing selected sequences into recombinant vectors for recombinant production. (PCR™ is a registered trademark of Hoffmann-LaRoche, Inc.). This is followed by cloning into the Pichia expression vector. The resulting plasmid is characterized by DNA sequence analysis, linearized by digestion with NotI, and spheroplasts will be prepared and transformed with the linearized construct according to the manufacturer's recommendations.

Transformation facilitates a recombination event in vivo between the 5' and 3' AOX1 sequences in the Pichia vector and those in the Pichia genome. The result is the replacement of AOX1 with the gene of interest.

Transformants are then plated on histidine-deficient media, which will select for successfully transformed cells. Transformants are further selected against slow growth on growth media containing methanol. Positive transformants are grown for 2 days in liquid culture and then for 2–6 days in broth that uses methanol as the sole carbon source. Protein expression is evaluated by sodium dodecyl sulfate-polyacrylamide gel electrophoresis (SDS-PAGE) and Western hybridization using a commercially available polyclonal antisera to the HA epitope (Pharmacia).

Recombinant type II collagen protein can be purified according to the manufacturer's recommendations, dialyzed against double distilled, deionized water and lyophilized in 10 mg aliquots. The aliquots are sterilized and used as implant material for the osteoconductive matrices.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the composition, methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

References

The following literature citations as well as those cited above are incorporated in pertinent part by reference herein for the reasons cited in the above text.

Abou-Samra, A. B., Juppner, H., Force, T., Freeman, M. W., Kong, X. F., Schipani, E., Urena, P., Richards, J., Bonventre, J. v., Potts, J. T., Kronenberg, H. M., Segre, G. V. (1992) Expression cloning of a common receptor for parathyroid hormone and parathyroid hormone-related peptide from rat osteoblast-like cells: a single receptor stimulates intracellular accumulation of both cAMP and inositol triphosphates and increases intracellular free Calcium. *Proc. Natl. Acad. Sci. U.S.A.* 89:2732–2736.

Agarwala, N., and Gay, C. V. (1992) *J. Bone Min. Res.* 7:531.

Alper, J. (1994) Boning up: newly isolated proteins heal bad breaks. *Science* 263:324–325.

Antonelli-Olridge, A., Saunders, K. B., Smith, S. R., and D'Amore, P. A. (1989) *Proc. Natl. Acad. Sci. U.S.A.* 86:4544–4548.

Benezra, M., Vlodavsky, I., Ishai-Michaeli, R., Neufeld, G., and Bar-Shavit, R. (1993) *Blood* 81:3324–3331.

Bandara, G., Robbins, P. D., Georgescu, H. I., Mueller, G. M., Glorioso, J. C., and Evans, C. H. (1992) Gene Transfer to Synoviocytes: Prospects for Gene Treatment of Arthritis. *DNA Cell Biol.* 11:(3):227–231.

Badylak et al., *J. Surg. Res.* 47:74–80 (1989).

Barr, P. J. (1991) *Cell* 66:1–3.

Beck, L. S., Deguzman L., Lee W. P. Xu Y., McFatridge L. A., Gillett N. A., Amento E. P. (1991) TGF-beta 1 induces bone closure of skull defects. *J. Bone Miner. Res.* 11:1257–65.

Benvenisty, N., Resf, L (1986). *Proc. Natl. Acad. Sci. U.S.A.* 83:9551.

Boden, S. D., Joyce, M. E., Oliver, B., and Bolander, M. E. (1989) Estrogen receptor mRNA expression in callus during fracture healing in the rat. *Calcif. Tissue Int.* 45:34–325.

Bonadio, J. and Goldstein, S. A. (1993) Our understanding of inherited skeletal fragility and what this has taught us about bone structure and function, in *Molecular and Cellular Biology of Bone*, Noda, M., ed., Academic Press, Inc., San Diego, Calif. pp. 169–189.

Bonadio, J., Jepsen, K., Mansoura, M. K., Kuhn, J. L., Goldstein, S. A., Jaenisch, R. (1993) An adaptive response by murine skeletal tissues that significantly increases the mechanical properties of cortical bone: implications for the treatment of skeletal fragility, *J. Clin. Invest.* 92:1697–1705.

Bonadio, J., Saunders, T. L., Tsai, E., Goldstein, S. A., Morris-Wiman, J., Brinkley, L., Dolan, D. F., Altschuler, R. A., Hawkins, J. E., Bateman, J. F., Mascara, T. and Jaenisch, R. (1990) Transgenic mouse model of the mild dominant form of osteogenesis imperfecta. *Proc. Natl. Acad. Sci. U.S.A.* 87:7145–7149.

Bonnarens, F., and Einhorn, T. A. (1984) Production of a standard closed fracture in laboratory animal bone. *J. Orthop. Res.* 2:97–101.

Burch, W. M., and Lebovitz, H. E. (1983) Parathyroid hormone stimulates growth of embryonic chick pelvic cartilage in vitro. *Calcif. Tissue Int.* 35:526–532.

Byers, P. H., and Steiner, R. D. (1992) Osteogenesis imperfecta. *Annu. Rev. Med.* 43:269–289.

Canalis, E., Centrella, M., Burch, W., et al. (1989) Insulin-like growth factor-1 mediates selective anabolic effects of parathyroid hormone in bone culture. *J. Clin. Invest.* 83:60–65.

Carrington, J. L., Roberts, A. B., Flanders, K. C., Roche, N. S., and Reddi, A. H. (1988) Accumulation, localization, and compartmentation of transforming growth factor b during endochondral bone development. *J. Cell Biol.* 107:1969–1975.

Centrella, M., McCarthy, T. L., and Canclis, E. (1988) Skeletal tissue and transforming growth factor-b. *FASEB J.* 22:23066–3073.

Cheifetz, S., Weatherbee, J. A., Tsang, M. L-S., Anderson, J. K., Mole, J.E., Lucas, R., and Massague, J. (1987) *Cell* 48:409–415.

Chen, T. L., Bates, R. L., Dudley, A., Hammonds, R. G., and Amento, E. P. (1991) Bone morphogenetic protein-2b stimulation of growth and osteogenic phenotypes in rat osteoblast-like cells: comparison with TGF-beta 1. *J. Bone Miner. Res.* 6:1387–93.

Chen, Y., Faraco, J., Yin, W., Germiller, J., Francke, U., and Bonadio, J. (1993) Structure, chromosomal localization, and expression pattern of the murine Magp gene. *J. Biol. Chem.* 268:27381–27389.

Colosetti, P., Hellman, U., Heldin, C-H, and Miyazono, K. (1993) *FEBS Letters* 320:140–144.

Compston, J. E., Silver, A. C., Croucher, P. I., Brown, R. C., and Woodhead, J. S. (1989) Elevated serum intact parathyroid hormone levels in elderly patients with hip fracture. *Clin. Endo.* 31:667–672.

Corson, G. M., Chalberg, S. C., Dietz, H. C., Charbonneau, N. L., and Sakai, L. Y. (1993) *Genomics* 17:476–484.

Cunningham, N. S., Paralkar, V., and Reddi, A. H. (1992) Osteogenic and recombinant bone morphogenetic protein 2B are chemotactic for human monocytes and stimulate transforming growth factor b1 mRNA expression. *Proc. Natl. Acad. Sci. U.S.A.* 89:11740–11744.

Davidson, B. L., Allen, E. D., Kozarsky, K. F., Wilson, J. M., and Roessler, B. J. (1993) A model system for in vivo gene transfer into the central nervous system using an adenoviral vector. *Nature Genetics* 3:219–223.

Davis, C. G. (1990) *New Biologist* 2:410–419.

Ejersted, C., Andreassen, T. T., Oxlund, H., Jorgense, P. H., Bak, B., Haggblad, J., Torring, O., and Nilsson, M. H. L. (1993) Human parathyroid hormone (1–34) and (1–84) increase the mechanical strength and thickness of cortical bone in rats. *J. Bone Min. Res.* 8:1097–1101.

Endo, H., Kyoki, M., Kawashima, K., Naruchi, T., and Hashimoto, Y. (1980) Vitamin D3 metabolites and PTH synergistically stimulate bone formation of chick embryonic femur in vitro. *Nature* 286:262–264.

Engel, J. (1989) *FEBS Letters* 251:1–7.

Falcone, D. J., McCaffrey, T. A., Haimovitz-Friedman, A., Vergilio, J-A., and Nicholson, A. C. (1993) *J. Biol. Chem.* 268:11951–11958.

Flaumenhaft, R., Abe, M., Sato, K., Miyazono, K., Harpel, J., Heldin, C-H., and Rifkin, D. B. (1993) *J. Cell Biol.* 120:995–1002.

Gunasekaran, S., Bathhurst, I. C., Constantz, B. R., Quiaoit, J., Bar, P. J., Gospodarowicz, D. (1993). Mineralized Collagen As A Substitute for Autograft Bone That Can Deliver Bone Morphogenic Protein. The 19th Annual Meeting of the SOCIETY FOR BIOMATERIALS, April 28, p. 253.

Gunasekaran, Subramanian, Ph.D., Constantz, Brent R., Ph.D., Quiaoit, James. Norian Corporation, Mountain View, Calif.; and Ross, John, Ph.D., Department of Chemistry, Stanford University, Stanford, Calif., Abstract V7.5, p. 426.

Gunness-Hey, M., and Hock, J. M. (1989) Loss of the anabolic effect of parathyroid hormone on bone after discontinuation of hormone in rats. *Bone* 10:447–452.

Gunness-Hey, M., and Hock, J. M. (1984) Increased trabecular bone mass in rats treated with human synthetic parathyroid hormone. *Metabl. Bone Dis.* 5:177–180.

Handford, P. A., Baron, M., Mayhew, M., Willis, A., Beesley, T., Brownlee, G. G., and Campbell, I. D. (1990) *EMBO J.* 9:475–480.

Hardy, J. R. W., Conlan, D., Hay, S., and Gregg, P. J. (1993) Serum ionized calcium and its relationship to parathyroid hormone after tibial fracture. *J. Bone Jt. Surg.* 75:645–649.

Hefti, E., Trechsel, U., Bonjor, J-P., Fleisch, H., and Schenk, R. (1982) *Clin. Sci.* 62:389–396.

Heine, U. I., Munoz, E. F., Flanders, K. C., Ellingsworth, L. R., Lam, H-Y. P., Thompson, N. L., Roberts, A. B., and Sporn, M. B. (1987) *J. Cell Biol.* 105:2861–2876.

Hendy, G. H., Kronenberg, H. M., Potts, J. T., and Rich, A. (1981) Nucleotide sequence of cloned cDNAs encoding human preproparathyroid hormone. *Proc. Natl. Acad. Sci. U.S.A.* 78:7365–7369.

Herrmann-Erlee, M. P. M., Heersche, J. N. M., Hekkelman, J. W., Gaillard, P. J., Tregear, G. W., Parsons, J. A., and Potts, J. T. (1976) Effects on bone in vitro of bovine parathyroid hormone and synthetic fragments representing residues 1–34, 2–34 and 3–34. *Endocrine Research Communications* 3:21–35.

Hock, J. M., and Gera, I. (1992) Effects of continuous and intermittent administration and inhibition of resorption on the anabolic response of bone to parathyroid hormone. *J. Bone and Min. Res.* 7:65–72.

Hock, J. M., and Fonseca, J. (1990) Anabolic effect of human synthetic parathyroid hormone (1–34) depends on growth hormone. Endocrinology 127:1804.

Hock, J. M., Gera, I., Fonseca, J., and Raisz, L. J. (1988) Human parathyroid hormone- (1–34) increases bone mass in ovariectomized and orchidectomized rats. *Endocrinology* 122:2899–2904.

Hori, M., Uzawa, T., Morita, K., Noda, T., Takahashi, H., and Inoue, J. (1988) Effect of human parathyroid hormone [PTH (1–34)] on experimental osteopenia of rats induced by ovariectomy. *J. Bone Min. Res.* 3:193–199.

Horowitz, M. C., Einhorn, T. A., Philbrick, W., et al. (1989) Functional and molecular changes in colony stimulating factor secretion by osteoblasts. *Connective Tissue Res.* 20:159–168.

Huggins, C. B., McCarroll, H. R., and Blocksom, B. H. (1936) Experiments on the theory of osteogenesis. The influence of local calcium deposits on ossification; the osteogenic stimulus of epithelium. *Arch. Surg.* 32:915.

Ichijo, H., Ronnstrand, L., Miyagawa, K., Ohashi, H., Heldin, C-H., and Miyazono, K. (1991) *J. Biol. Chem.* 266:22459–22464.

Izumi, T., Scully, S. P., Heydemann, A., and Bolander, M. E. (1992) Transforming growth factor b1 stimulates type II collagen expression in cultured periosteal-derived cells. *J. Bone Min. Res.* 7:115–11.

Jepsen, K. J. (1994) Characterization of the hierarchical composite properties of cortical bone: a transgenic approach. Ph.D. Thesis (Bioengineering), University of Michigan.

Jepse, K. J., Kuhn, J. L., Mansoura, M. K., Goldstein, S. A., Wu, H., Jaenisch, R., and Bonadio, J. Expression of a single functioning COL1A1 transgene rescues the skeletal phenotype of Mov13 transgenic mice. Submitted for publication.

Jingushi, S., Joyce, M. E., and Bolander, M. E. (1992) Genetic expression of extracellular matrix proteins correlates with histologic changes during fracture repair. *J. Bone Min. Res.* 7:1045–1055.

Jingushi, S., Heydemann, A., Kana, S. K., Macey, L. R. and Bolander, M. E. Acidic fibroblast growth factor injection stimulates cartilage enlargement and inhibits cartilage gene expression in rat fracture healing. (1990) *J. Orthop. Res.* 8:364–371.

Johnston, C. C., Norton, J., Khairi, M. R. A., Kernek, C., Edouard, C., Arlot, M., and Meunier, P. J. (1985) Heterogeneity of fracture syndromes in postmenopausal women. *J. Clin. Endo. Metab.* 61:551–556.

Joyce, M. E., Roberts, A. B., Sporn, M. B., and Bolander, M. E. (1990) Transforming growth factor-b and the initiation of chondrogenesis and osteogenesis in the rat femur. *J. Cell Biol.* 110:195–2007.

Juppner, H., Abou-Samra, A. B., Freeman, M., Kong, X. F., Schipani, E., Richards, J., Kolakowski, L. F., Hock, J., Potts, J. T., Kronenberg, H. M., Segre, G. V. (1991) A G-protein-linked receptor for parathyroid hormone and parathyroid hormone-related peptide. *Science* 254:1024–1026.

Kanzaki, T., Olofsson, A., Moren, A., Wernstedt, C., Hellman, U., Miyazono, K., Claesson-Welsh, L., and Heldin, C-H. (1990) *Cell* 61:1051–1061.

Kawashima, K. (1980) Growth stimulative effect of parathyroid hormone, calcitonin and $N^6$, $02'$-dibutyryl adenosine $3'$, $5'$-cyclic monophosphoric acid on chick embryonic cartilage cultivated in a chemically defined medium. *Endocrinol. Jpn.* 27:349–356.

Klein-Nulend, J., Fall, P. M., and Raisz, L. G. (1990) Comparison of the effects of synthetic human parathyroid hormonerelated peptide of malignancy and bovine PTH- (1–34) on bone formation and resorption in organ culture. *Endocrinology* 126:223–227.

Kovacina, K. S., Steele-Perkins, G., Purchio, A. F., Lioubin, M., Miyazono, K., Heldin, C-H., and Roth, R. A. (1989) *Biochem. Biophys. Res. Commun.* 160:393–403.

Kozak, M. (1991) *J. Biol. Chem.* 266:19867–19870.

Kream, B. E., LaFrancis, D., Petersen, D. N., Woody, C., Clark, S., Rowe, D. W., and Lichtler, A. Parathyroid hormone represses a1 (I) collagen promoter activity in cultured calvariae from neonatal transgenic mice. (1993) *Mol. Endocrinology* 7:399–408.

Kyte & Doolittle (1982) *J. Mol. Biol.* 157:105–132.

Lee K., Deeds, J. D., Chiba, S., Un-no, M., Bond, A. T., and segre, G. V. Parathyroid hormone induces sequential c-fos expression in bone cells in vivo: in situ localization of its receptor and c-fos mRNAs. *Endocrinology*.

Lewinson, D., and Silbermann, M. (1986) Parathyroid hormone stimulates proliferation of chondroprogenitor cells in vitro. *Calcif. Tissue Int.* 38:155–162.

Ledley, J. (1987). *J. Pediatrics* 110:1.

Lee, B., Vissing, H., Ramirez, F., Rogers, D., and Riomoin, D. (1989) Identification of the molecular defect in a family with spondyloepiphyseal dysplasia. *Science* 244:978–980.

Lehnert, S. A., and Akhurst, R. J. (1988) *Development* 104:263–273.

Linkhart, T. A., and Mohan, S. (1989) Parathyroid hormone stimulates release of insulin-like growth factor-1 (IGF-1) and IGF-II from neonatal mouse calvaria in organ culture. *Endocrinology* 125:1484–1491.

Liu, C. C., Kalu, D. N., Salerno, E., Echon, R., Hollis, B. W., and Ray, M. (1991) Preexisting bone loss associated with ovariectomy in rats is reversed by parathyroid hormone. *J. Bone and Mins. Res.* 6:1071–1080.

Liu, C. C. and Kalu, D. N. (1990) Human parathyroid hormone (1–34) prevents bone loss and augments bone formation in sexually mature ovariectomized rats. *J. Bone Min. Res.* 5:973–982.

Luyten, F. P., Cunningham, N. S., Ma, S., Muthukumaran, N., Hammonds, R. G., Nevins, W. B., Wood, W. I., and Reddi, A. H. (1989) Purification and partial amino acid sequence of osteogenic, a protein initiating bone differentiation. *J. Biol. Chem.* 264:13377–13380.

Lyons, R. M., and Moses, H. L. (1990) *Eur. J. Biochem.* 187:467–473.

Lyons, R. M., Keski-Oja, J., and Moses, H. L. (1988) *J. Cell Biol.* 106:1549–1665.

MacArthur, M. W., and Thronton, J. M. (1991) *J. Mol. Biol.* 218:397–412 Lyons et al., *Proc. Natl. Acad. Sci. USA*, 86:4554–4558, 1989.

Majmudar, G., Bole, D., Goldstein, S. A., Bonadio, J. (1991) Bone cell culture in a three-dimensional polymer bead stabilizes the differentiated phenotype and provides evidence that osteoblastic cells synthesize type III collagen and fibronectin. *J. Bone and Min. Res.* 6:869–881.

Malluche, H. H., Matthews, C., Faugere, M-C., Fanti, P., Endres, D. B., and Friedler, R. M. (1986) 1,25-dihydroxyvitamin D maintains bone cell activity, and parathyroid hormone modulates bone cell number in dogs. *Endocrinology* 119:1298–1304.

Massague, J. (1990) *Annu. Rev. Cell Biol.* 6:597–641.

Meller, Y., Kestenbaum, R. S., Mozes, M., Mozes, G., Yagil, R., and Shany, S. (1984) Mineral and endocrine metabolism during fracture healing in dogs. *Clin. Orthop. Rel. Res.* 187:289–295.

Michaelson, E., Malmstrom, V., Reis, S., Engstrom, A., Burkhardt, H., and Holmdahl, R. (1994) T-cell recognition of carbohydrates on type II collagen. *J. Exp. Med.* 180:745–749.

Millan, F. A., Denhez, F., Kondaiah, P., and Akhurst, R. J. (1991) *Development* 111:131–144.

Mitalk, B. H., Williams, D. C., Bryant, H. U., Paul, D. C., and Neer, R. M. (1992) Intermittent administration of bovine PTH-(1–34) increases serum 1,25-dihydroxyvitamin D concentrations and spinal bone density in senile (23 month) rats. *J. Bone Min. Res.* 7:479–484.

Miyazono, K., Hellman, U., Wernstedt, C., and Heldin, C-H. (1988) *J. Biol. Chem.* 263:6407–6415.

Miyazono, K., Olofsson, A., Colosetti, P., and Heldin, C-H. (1991) *EMBO J.* 10:1091–1101.

Miyazono, K., Thyberg, J., and Heldin, C-H. (1992) *J. Biol. Chem.* 267:5668–5675.

Nicolau, C., et al. (1983). *Proc Natl. Acad. Sci. U.S.A.* 80:1068.

O'Malley Jr., B. W. and Ledley, F. D., (1993) Somatic Gene Therapy in Otolaryngology-Head and Neck Surgery. *Arch Otolaryngol Head Neck Surg.* 119:1191–1197.

Ogawa, Y., Schmidt, D. K., Dasch, J. R., Chang, R-J., Glaser, C. B. (1992) *J. Biol. Chem.* 267:2325–2328.

Ohlin, A-K., Linse, S., and Stenflo, J. (1988) *J. Biol. Chem.* 263:7411–7417.

Olofsson, A., Miyazono, K., Kanzaki, T., Colosetti, P., Engstrom, U., and Heldin, C-H. (1992) *J. Biol. Chem.* 267:19482–19488.

Ortman, R. A., Holderbaum, D., Qu, X. M., Banerjee, S., and Haqqi, T. M. (1994) BUB/BnJ (H-2q) is a TCR deletion mutant mouse strain (TCR V beta a KJ16-) that is susceptible to type II collagen-induced arthritis. *J. Immunol.* 152:4175–4182.

Ozkaynak, E., Rueger, D. C., Drier, E. A., Corbett, C., Ridge, R. J., Sampath, T. K., and Oppermann, H. (1990) OP-1 CDNA encodes an osteogenic protein in the TGF-b family. *EMBO J.* 9:2085–2093.

Paralkar, V. M., Hammonds, R. G., and Reddi, A. H. Identification and characterization of cellular binding proteins (receptors) for recombinant human bone morphogenetic protein 2B, an initiator of bone differentiation cascade. (1991) *Proc. Natl. Acad. Sci. U.S.A.* 88:3397–3401.

Parsons, J. A. and Reit, B. (1974) Chronic response of dogs to parathyroid hormone infusion. *Nature* 250:254–257.

Pelton, R. M., Dickinson, M. E., Moses, H. L., and Hogan, B. L. M. (1990b) *Development* 110:609–620.

Pelton, R. M., Hogan, B. L. M., Miller, D. A., and Moses, H. L. (1990a) *Dev. Biol.* 141:456–460.

Pelton, R. W., Nomura, S., Moses, H. L., and Hogan, B. L. M. (1989) *Development* 106:759–767.

Pereira, L., D'Alessio, M., Ramierz, F., Lynch, J. R., Sykes, B., Pangilinan, T., and Bonadio, *J. Human Mol. Genet.* 2:961–968.

Persson, E., Selander, M., Linse, S., Drakenberg, T., Ohlin, A-K., and Stenflo, J. (1989) *J. Biol. Chem.* 264:16897–16904.

Pircher, R., Jullien, P., and Lawrence, D. A. (1986) *Biochem. Biophys. Res. Commun.* 136:30–37.

Pircher, R., Lawrence, D. A., and Jullien, P. (1984) *Cancer Res.* 44:5538–5543.

Podbesek, R., Edouard, C., Meunier, P. J., Parsons, J. A., Reeve, J., Stevenson, R. W., and Zanelli, J. M. (1983) Effects of two treatment regimes with synthetic human parathyroid hormone fragment on bone formation and the tissue balance of trabecular bone in greyhounds. *Endocrinology* 112:1000–1006.

Prockop, D. J. (1990) Mutations that alter the primary structure of type I collagen. The perils of a system for generating large structures by the principle of nucleated growth. *J. Biol. Chem.* 265:15349–15352.

Raisz, L. G., and Kream, B. E. (1983) Regulation of bone formation. *N. Engl. J. Med.* 309:29–35.

Reeve, J., Meunier, P. J., Parsons J. A., Bernat, M., Bijvoet, O. L., Courpron, P., Edouard, C., Klenerman, L., Neer, R. M., Renier, J. C., Slovik, D., Vismans, F. J. F. E., and Potts, J. T. (Jun. 7, 1980) Anabolic effect of human parathyroid hormone fragment on trabecular bone in involutional osteoporosis: a multicentre trial. *Br. Med. J.* 1340–1344.

Reeve, J., Hesp, R., Williams, et al. (May 15, 1976) Anabolic effect of low doses of a fragment of human parathyroid hormone ont he skeleton in postmenopausal osteoporosis. *Lancet* 1035–1038.

Riond, J-L. (1993) Modulation of the anabolic effect of synthetic human parathyroid hormone fragment (1–34) in the bone of growing rats by variations in dosage regimen. *Clin. Sci.* 85:223–228.

Rizzoli, R. E., Somerman, M., Murray, T. M., and Aurbach, G. D. (1983) Binding of radioiodinated parathyroid hormone to cloned bone cells. *Endocrinology* 113:1832.

Roberts, A. B. and Sporn, M. B. The transforming growth factorbetas. In Handbook of Experimental Pharmacology: Peptide Growth Factors and Their Receptors. Vol. 95, M. B. Sporn and A. B. Roberts, eds., Springer-Verlag, Heidelberg, 1989.

Rosen, V., Wozney, J. M., Wang, E. A., Cordes, P., Celeste, A., McQuaid D., and Kurtzberg, L. Purification and molecular cloning of a novel group of EMPs and localization of BMP mRNA in developing bone. (1989) *Connect. Tissue Res.* 20:313–319.

Roessler, B. J., Allen, E. D., Wilson, J. M., Hartman, J. W., and Davidson, B. L., Adenoviral-mediated Gene Transfer to Rabbit Synovium In Vivo. (1993) *J. Clin. Invest.* 92:1085–1092.

Sambrook, J., Fritsch, E. F., and Maniatis, T. *Molecular Cloning, A Laboratory Manual.* Cold Spring Harbor Laboratory Press, 1989, pp. 18.60.

Sampath, T. K., Nathanson, M. A., and Reddi, A. H. (1984) In vitro transformation of mesenchymal cells derived from embryonic muscle into cartilage in response to extracellular matrix components of bone. *Proc. Natl. Acad. Sci. U.S.A.* 81:3419–3423.

Sampath, T. K. and Reddi, A. H. (1981). Dissociative extraction and reconstitution of extracellular matrix components involved in local bone differentiation. *Proc. Natl. Acad. Sci. U.S.A.* 78:7599–7603.

Sandusky, G. E., Jr., Badylak, S. F., Morff, R. J., Johnson W. D., Lantz, G. (1992) *Am. J. Path.*, 140(2):317.

Sato, Y., Okada, F., Abe, M., Sguchi, T., Kuwano, M., Sato, S., Furuya, A., Hanai, N., and Tamaoki, T. (1993) *J. Cell Biol.* 123:1249–1254.

Schluter, K-D., Hellstern, H., Wingender, E., and Mayer, H. (1989) The central part of parathyroid hormone stimulates thymidine incorporation of chondrocytes. *J. Biol. Chem.* 264:11087–11092.

Schnieke, A., Harbers, K., and Jaenisch, R. (1983) Embryonic lethal mutation in mice induced by retrovirus insertion into the a1 (I) collagen gene. *Nature* 304:315–320.

Seeger, C., Ganem, D., Varmus, H. E. (1984). *Proc. Natl. Acad. Sci. U.S.A.* 81:5849.

Seitz, P. A., Zhu, B-T., and Cooper, C. W. (1992) Effect of transforming growth factor b on parathyroid hormone receptor binding and cAMP formation in rat osteosarcoma cells. *J. Bone Min. Res.* 7:541–546.

Selander-Sunnerhagen, M., Ullner, M., Persson, E., Teleman, O., Stenflo, J., and Drakenberg, T. (1992) *J. Biol. Chem.* 267:19642–19649.

Selye, H. (1932) Endocrinology 16:547

Shimahama, S., Rosenberg, M. A., Fagan, A.M., Wolff, J. A., Short, M. P., Breakefield, X. O., Friedmann, T., and Gage, F. H. (1989) Grafting genetically modified cells into the rat brain: characteristics of E. coli b-galactosidase as a reporter gene. *Molecular Brain Research* 5:271–278.

Shimell, M. J., Ferguson, E. L., Childs, S. R., and O'Connor, M. B. (1991) The Drosophila dorsal-ventral patterning gene tolloid is related to human bone morphogenetic protein 1. *Cell* 67:469–481.

Silve, C. M., Hradek, G. T., and Arnaud, C. D. (1982) Parathyroid hormone receptor in intact embryonic chicken bone: characterization and cellular localization. *J. Cell. Biol.* 94:379.

Slovik, D. M., Rosenthal, D. I., Doppelt, S. H., Potts, J. T., Daly, M. A., Campbell, J. A., Neer, R. M. (1986) Restoration of spinal bone in osteoporotic men by treatment with human parathyroid hormone (1–34) and 1,25-dihydroxyvitamin D. *J. Bone Min. Res.* 1:377–381.

Somjen, D., Schluuter, K-D., Wingener, E., Mayer, H., and Kaye, A. M. (1990) Stimulation of cell proliferation in skeletal tissues of the rat by defined parathyroid hormone fragments. *Biochem J.* 272:781–785.

Spencer, E. M., Si, E. C. C., Liu, C. C., and Howard, G. A. (1989) Parathyroid hormone potentiates the effect of insulin-like growth factor-I on bone formation. *Acta Endocrinological (Copenh)* 121:435–442.

Steiner, D. F., Smeekens, S. P., Ohagi, S., and Chan S. J. (1992) *J. Biol. Chem.* 267:23435–23438.

Steiner, D. F., Smeekens, S. P., Ohagi, S., and Chan, S. J. (1992) *J. Biol. Chem.* 257:23435–23438.

Stenman, G., Sahlin, P., Olofsson, A., Geurts van Kessel, A., and Miyazono, K. (1994) *Cytogenet. Cell Genet.* 66:117–119.

Stevenson, R. W., and Parsons, J. A. (1983) Effects of parathyroid hormone and the synthetic 1–34 amino-terminal fragment in rats and dogs. *J. Endocr.* 97:21–30.

Stratford-Perricaudet, L. D., Makeh, I., Perricaudet, M., and Birand, P. (1992) Widespread long-term gene transfer to mouse skeletal muscles and heart. *J. Clin. Invest.* 90:626–630.

Streuli, C. H., Schmidhauser, C., Kobrin, M., Bissell, M. J., and Derynck, R. (1993) *J. Cell Biol.* 120:253–260.

Tada, K., Yamamuro, T., Okumura, H., Kasai, R., and Takahashi, H. (1988) *Bone* 11:163–169.

Taipale, J., Miyazono, K., Heldin, C-H., and Keski-Oja, J. (1994) *J. Cell Biol.* 124:171–181.

Tam, C. S., Heersche, J. N. M., Murray, T. M., and Parsons, J. A. (1982) Parathyroid hormone stimulates the bone apposition rate independently of its resorptive action: differential effects of intermittent and continuous administration. *Endocrinology* 110:506–512.

Toriumi, D. M., Kotler, H. S., Luxenberg, D. P., Holtrop, M. E., and Wang, E. A. Mandibular reconstruction with a recombinant bone-inducing factor. (1991) *Arch. Otolaryngol. Head Neck Surg.* 117:1101–1112.

Tregear, G. W., Van Rietschoten, J., Greene, E., Ketmann, H. T., Niall, H. D., Reit, B., Parsons, J. A., and Potts, J. T. (1973) Bovine parathyroid hormone: minimum chain length of *Endocrinology* 93:1349–1353.

Tsuji, T., Okada, F., Yamaguchi, K., and Nakamura, T. (1990) *Proc. Natl. Acad. Sci. U.S.A.* 87:8835–8839.

Ulmer, J. B., Donnelly, J. J., Parker, S. E., et al. (1993) Heterologous protection against influenza by injectio of DNA encoding a viral protein. *Science* 259:1745–1749.

Urist, M. R., DeLange, R. J., and Finerman, G. A. M. Bone cell differentiation and growth factors. *Science* 220:680–686 (1983).

Urist, M. R. Bone formation by autoinduction. *Science* 150:893–899 (1965).

van der Plas, A. (1985) Direct effect of parathyroid hormone on the proliferation of osteoblast-like cells; a possible involvement of cyclic AMP. *Biochem. Biophys. Res. Comm.* 129:918–925.

Vukicevic, S., Luyten, F. P., and Reddi, A. H. (1989) Stimulation of the expression of osteogenic and chondrogenic phenotypes in vitro by osteogenic. *Proc. Natl. Acad. Sci. U.S.A.* 86:8793–8797.

Wang, E. A., Rosen, V., D'Alessandro, J. S., Bauduy, M., Cordes, P., Harada, T., Israel, D., Hewick, R. M., Kerns, K. M., LaPan, P., Luxenberg, D. P., McQuaid, D., Moutsatsos, I. K., Nove, J., and Wozney, J. M. (1990) Recombinant human bone morphogenetic protein induces bone formation. *Proc. Natl. Acad. Sci. U.S.A.* 87:2220–2224.

Wilson, J. M., Grossman, M., Thompson, A. R. et al. (1992) Somatic gene transfer in the development of an animal model for primary hyperparathyroidism. *Endocrinology* 130:2947–2954.

Wolff, J. A., Malone, R. W., Williams, P., Chong, W., Acsadi, G., Jani, A., and Felgner, P. L. (1990) Direct gene transfer into mouse muscle in vivo. *Science* 247:1465–1468.

Wozney, J. M., Rosen, V., Celeste, A. J., Mitsock, L. M., Whitters, M. J., Kriz, R. W., Hewick, R. M., and Wang, E. A. (1988) Novel regulators of bone formation: molecular clones and activities. *Science* 242:1528–1534.

Yasko, A. W., Lane, J. M., Fellinger, E. J., Rosen, V., Wozney, J. M., and Wang, E. A. (1992) The healing of segmental bone defects, induced bu recombinant human bone morphogenetic protein (rhBMP-2). A radiographic, histological, and biomechanical study in rats. *J. Bone Joint Surg.* 5:659–70.

Yasuda, T., Banville, Rabbani, S. A. Hendy, G. N. Goltzman. (1989) Rat parathyroid hormonelike peptide: Comparison with the human homologue and expression malignant and normal tissue. *Mol. Endocrinol.* 3:518–525.

Yin, W., Germiller, J., Sanguineti, C., Smiley, E., Pangilinan, T., Pereira, L., Ramierz, F., and Bonadio, J. Submitted for publication.

Zhang, H., Apfelroth, S. D., Davis, E. C., Sanguineti, C., Ronadio, J., Mecham, R. P., and Ramirez, F. (1994) *J. Cell Biol.* 124:855–863.

What is claimed is:

1. A method for transferring nucleic acid segments into bone progenitor cells located within a bone progenitor tissue site of an animal, comprising contacting said tissue site with a composition comprising two or more nucleic acid segments and a structural bone-compatible matrix, so as to transfer said two or more nucleic acid segments into said cells, wherein said cells express transcriptional or translational products encoded by said nucleic acid segments.

2. The method of claim 1, comprising contacting bone progenitor cells with a composition comprising two nucleic acid segments and a structural bone-compatible matrix.

3. The method of claim 1, comprising contacting bone progenitor cells with a composition comprising three nucleic acid segments and a structural bone-compatible matrix.

4. The method of claim 1, wherein the contacting process comprises bringing said two or more nucleic acid segments into contact with said structural bone-compatible matrix to form a matrix-nucleic acid segments composition and bringing said matrix-nucleic acid segments composition into contact with said tissue site.

5. The method of claim 4, wherein said nucleic acid segments are absorbed in said structural bone-compatible matrix.

6. The method of claim 4, wherein said nucleic acid segments are adsorbed to said structural bone-compatible matrix.

7. The method of claim 4, wherein said nucleic acid segments are impregnated within said structural bone-compatible matrix.

8. The method of claim 1, wherein said bone progenitor cells are stem cells, macrophages, fibroblasts, vascular cells, osteoblasts, chondroblasts or osteoclasts.

9. The method of claim 8, wherein said bone progenitor cells are fibroblasts.

10. The method of claim 1, wherein at least one of said two or more nucleic acid segments is a DNA molecule.

11. The method of claim 1, wherein at least one of said two or more nucleic acid segments is an antisense nucleic acid molecule.

12. The method of claim 1, wherein at least one of said two or more nucleic acid segments is a linear nucleic acid molecule, a plasmid or a recombinant insert within the genome of a recombinant virus.

13. The method of claim 1, wherein at least one of said two or more nucleic acid segments encodes a polypeptide or protein that stimulates bone progenitor cells when expressed by said cells.

14. The method of claim 1, wherein said structural bone-compatible matrix is a collagenous, metal, hydroxylapatite, bioglass, aluminate, bioceramic, acrylic ester polymer, lactic acid polymer, glycolic acid polymer or lactic acid/glycolic acid polymer matrix.

15. The method of claim 14, wherein said structural bone-compatible matrix is a titanium matrix.

16. The method of claim 15, wherein said structural bone-compatible matrix is a titanium matrix coated with hydroxylapatite.

17. The method of claim 14, wherein said structural bone-compatible matrix is a collagen preparation.

18. The method of claim 17, wherein said structural bone-compatible matrix is a type II collagen preparation.

19. The method of claim 18, wherein said structural bone-compatible matrix is a recombinant type II collagen preparation.

20. The method of claim 18, wherein said structural bone-compatible matrix is a type II collagen preparation further supplemented with minerals.

21. The method of claim 14, wherein said structural bone-compatible matrix is a lactic acid polymer, glycolic acid polymer or lactic acid/glycolic acid polymer matrix.

22. The method of claim 1, wherein at least one of said two or more nucleic acid segments is an RNA molecule.

23. A method of stimulating bone progenitor cells located within a bone progenitor tissue site of an animal, comprising contacting said tissue site with a composition comprising two or more osteotropic genes and a structural bone-compatible matrix so as to promote expression of said genes by said cells.

24. The method of claim 23, comprising contacting said tissue site with a composition comprising two osteotropic genes and a structural bone-compatible matrix.

25. The method of claim 23, comprising contacting said tissue site with a composition comprising three osteotropic genes and a structural bone-compatible matrix.

26. The method of claim 23, wherein expression of said osteotropic genes by said cells stimulates said cells to promote bone tissue growth.

27. The method of claim 23, wherein the contacting process comprises bringing said osteotropic genes into contact with said structural bone-compatible matrix to form a matrix-genes composition and bringing said matrix-genes composition into contact with said tissue site.

28. The method of claim 23, wherein said osteotropic genes are absorbed in said structural bone-compatible matrix.

29. The method of claim 23, wherein said osteotropic genes are adsorbed in said structural bone-compatible matrix.

30. The method of claim 23, wherein said osteotropic genes are impregnated within said structural bone-compatible matrix.

31. The method of claim 23, wherein said bone progenitor cells are stem cells, macrophages, fibroblasts, vascular cells, osteoblasts, chondroblasts or osteoclasts.

32. The method of claim 31, wherein said bone progenitor cells are fibroblasts.

33. The method of claim 23, wherein at least one of said two or more osteotropic genes is in the form of plasmid DNA, a DNA insert within the genome of a recombinant adenovirus, a DNA insert within the genome of a recombinant adeno-associated virus (AAV) or a DNA insert within the genome of a recombinant retrovirus.

34. The method of claim 23, wherein at least one of said two osteotropic genes is a parathyroid hormone (PTH) gene, a bone morphogenetic protein (BMP) gene, a growth factor gene, a growth factor receptor gene, a cytokine gene or a chemotactic factor gene.

35. The method of claim 34, wherein at least one of said two osteotropic genes is a PTH gene.

36. The method of claim 34, wherein at least one of said two osteotropic genes is a BMP-2A, BMP-2B, BMP-3, BMP-4, BMP-5, BMP-6, BMP-7 or BMP-8 gene.

37. The method of claim 34, wherein at least one of said two osteotropic genes is a PTH1-34 gene, a BMP-2 gene or a BMP-4 gene.

38. The method of claim 34, wherein said composition comprises a PTH gene and a BMP gene.

39. The method of claim 38, wherein said composition comprises a PTH1-34 gene and a BMP-4 gene.

40. The method of claim 34, wherein at least one of said two osteotropic genes is a transforming growth factor (TGF) gene, a fibroblast growth factor (FGF) gene, a granulocyte/macrophage colony stimulating factor (GMCSF) gene, an epidermal growth factor (EGF) gene, a platelet derived growth factor (PDGF) gene, an insulin-like growth factor (IGF) gene, a latent TGF-β binding protein (LTBP) gene or a leukemia inhibitory factor (LIF) gene.

41. The method of claim 40, wherein at least one of said two or more osteotropic genes is a TGF-α, TGF-β1 or TGF-β2 gene.

42. The method of claim 40, wherein at least one of said two or more osteotropic genes is an LTBP gene.

43. The method of claim 22, wherein said structural bone-compatible matrix is a collagenous, metal, hydroxylapatite, bioglass, aluminate, bioceramic, acrylic ester polymer, lactic acid polymer, glycolic acid polymer or lactic acid/glycolic acid polymer matrix.

44. The method of claim 43, wherein said structural bone-compatible matrix is a titanium matrix.

45. The method of claim 44, wherein said structural bone-compatible matrix is a titanium matrix coated with hydroxylapatite.

46. The method of claim 43, wherein said structural bone-compatible matrix is a collagen preparation.

47. The method of claim 46, wherein said structural bone-compatible matrix is a type II collagen preparation.

48. The method of claim 47, wherein said structural bone-compatible matrix is a recombinant type II collagen preparation.

49. The method of claim 47, wherein said structural bone-compatible matrix is a mineralized type II collagen preparation.

50. The method of claim 43, wherein said structural bone-compatible matrix is a lactic acid polymer, glycolic acid polymer or lactic acid/glycolic acid polymer matrix.

51. The method of claim 23, wherein said composition is applied to a bone fracture site in said animal.

52. The method of claim 23, wherein said composition is implanted within a bone cavity site in said animal.

53. The method of claim 52, wherein said bone cavity site is the result of dental or periodontal surgery or the removal of an osteosarcoma.

54. A method of delivering two or more nucleic acid segments to a fibroblast cell located within a repair tissue site of an animal, comprising contacting said tissue site with a composition comprising two or more nucleic acid segments and a structural bone-compatible matrix to effect uptake of the nucleic acid segments into the fibroblast cell and to promote expression of transcriptional or translational products by said fibroblast cell.

55. A method of delivering two or more selected nucleic acid segments to a fibroblast cell located within a repair tissue site of an animal, comprising the steps of:
(a) preparing a matrix-nucleic acid composition comprising two or more nucleic acid segments and a structural bone-compatible matrix; and
(b) contacting said repair tissue site with the structural matrix-nucleic acid composition to effect uptake of the nucleic acid segments by the fibroblast cell, wherein said fibroblast cell expresses transcriptional or translational products encoded by said nucleic acid segments.

56. The method of claim 55, wherein step (a) comprises preparing a matrix-nucleic acid composition comprising two nucleic acid segments and a structural bone-compatible matrix.

57. The method of claim 55, wherein step (a) comprises preparing a matrix-nucleic acid composition comprising three nucleic acid segments and a structural bone-compatible matrix.

58. The method of claim 55, wherein said nucleic acid segments are absorbed in or adsorbed to said structural bone-compatible matrix.

59. The method of claim 55, wherein said nucleic acid segments are impregnated within said structural bone-compatible matrix.

60. The method of claim 55, wherein at least one of said two or more nucleic acid segments is a DNA molecule.

61. The method of claim 55, wherein at least one of said two or more nucleic acid segments is an RNA molecule.

62. The method of claim 55, wherein at least one of said two or more nucleic acid segments is an antisense nucleic acid molecule.

63. The method of claim 55, wherein at least one of said two or more nucleic acid segments is a linear nucleic acid molecule, a plasmid or a recombinant insert within the genome of a recombinant virus.

64. The method of claim 55, wherein at least one of said two or more nucleic acid segments is an osteotropic gene.

65. The method of claim 64, wherein at least one said osteotropic genes is a parathyroid hormone (PTH) gene, bone morphogenetic protein (BMP) gene, a growth factor gene, a growth factor receptor gene, a cytokine gene or a chemotactic factor gene.

66. The method of claim 65, wherein at least one of said osteotropic genes is a transforming growth factor (TGF) gene, a fibroblast growth factor (FGF) gene, a granulocyte/macrophage colony stimulating factor (GMCSF) gene, an epidermal growth factor (EGF) gene, a platelet derived growth factor (PDGF) gene, an insulin-like growth factor (IGF) gene, a latent TGF-β binding protein (LTBP) gene or a leukemia inhibitory factor (LIF) gene.

67. The method of claim 66, wherein at least one of said osteotropic genes is a TGF-α, TGF-β1 or TGF-β2 gene.

68. The method of claim 65, wherein at least one of said osteotropic genes is a PTH gene.

69. The method of claim 68, wherein at least one of said osteotropic genes is a PTH1-34 gene.

70. The method of claim 65, wherein at least one of said osteotropic genes is a BMP-2A, BMP-2B, BMP-3, BMP-4, BMP-5, BMP-6, BMP-7 or BMP-8 gene.

71. The method of claim 70, wherein at least one of said osteotropic genes is a BMP-2 or BMP-4 gene.

72. The method of claim 65, wherein said matrix-nucleic acid composition comprises a PTH gene and a BMP gene.

73. The method of claim 72, wherein said matrix-nucleic acid composition comprises a PTH1-34 gene and a BMP-4 gene.

74. The method of claim 66, wherein at least one of said osteotropic genes is an LTBP gene.

75. The method of claim 55, wherein said structural bone-compatible matrix is a collagenous, metal, hydroxylapatite, hydroxylapatite-coated metal, bioglass, aluminate, bioceramic, acrylic ester polymer, lactic acid polymer, glycolic acid polymer or lactic acid/glycolic acid polymer matrix.

76. The method of claim 75, wherein said structural bone-compatible matrix is a titanium matrix.

77. The method of claim 76, wherein said structural bone-compatible matrix is a titanium matrix coated with hydroxylapatite.

78. The method of claim 75, wherein said structural bone-compatible matrix is a collagen preparation.

79. The method of claim 78, wherein said structural bone-compatible matrix is a type II collagen preparation.

80. The method of claim 79, wherein said structural bone-compatible matrix is a recombinant type II collagen preparation.

81. The method of claim 79, wherein said structural bone-compatible matrix is a type II collagen preparation further supplemented with minerals.

82. The method of claim 55, wherein said structural bone-compatible matrix is a lactic acid polymer, glycolic acid polymer or lactic acid/glycolic acid polymer matrix.

83. A composition comprising two or more nucleic acid segments in association with a structural bone-compatible matrix.

84. The composition of claim 83, wherein said composition comprises two nucleic acid segments in association with said structural bone-compatible matrix.

85. The composition of claim 83, wherein said composition comprises three nucleic acid segments in association with said structural bone-compatible matrix.

86. The composition of claim 83, wherein said nucleic acid segments are absorbed in or adsorbed to said structural bone-compatible matrix.

87. The composition of claim 83, wherein said nucleic acid segments are impregnated within said structural bone-compatible matrix.

88. The composition of claim 83, wherein at least one of said two or more nucleic acid segments is a DNA molecule.

89. The composition of claim 83, wherein at least one of said two or more nucleic acid segments is an RNA molecule.

90. The composition of claim 83, wherein at least one of said two or more nucleic acid segments is an antisense nucleic acid molecule.

91. The composition of claim 83, wherein at least one of said two or more nucleic acid segments is a linear nucleic acid molecule, a plasmid or a recombinant insert within the genome of a recombinant virus.

92. The composition of claim 83, wherein at least one of said two or more nucleic acid segments encodes a polypeptide or protein that stimulates bone progenitor cells when expressed by said cells.

93. The composition of claim 83, wherein said structural bone-compatible matrix is a collagenous, titanium, hydroxylapatite, hydroxylapatite-coated titanium, bioglass, aluminate, bioceramic, acrylic ester polymer, lactic acid polymer, glycolic acid polymer or lactic acid/glycolic acid polymer matrix.

94. The composition of claim 93, wherein said structural bone-compatible matrix is a collagen preparation.

95. The composition of claim 93, wherein said structural bone-compatible matrix is a type II collagen preparation.

96. The composition of claim 95, wherein said structural bone-compatible matrix is a recombinant type II collagen preparation.

97. The composition of claim 95, wherein said structural bone-compatible matrix is a type II collagen preparation further supplemented with minerals.

98. The composition of claim 97, wherein said structural bone-compatible matrix is a type II collagen preparation further supplemented with calcium.

99. The composition of claim 93, wherein said structural bone-compatible matrix is a lactic acid polymer, glycolic acid polymer or lactic acid/glycolic acid polymer matrix.

100. A composition comprising two or more osteotropic genes in association with a structural bone-compatible matrix, said composition being capable of stimulating bone growth when administered to a bone progenitor tissue site of an animal.

101. The composition of claim 100, wherein said composition comprises two osteotropic genes in association with said structural bone-compatible matrix.

102. The composition of claim 100, wherein said composition comprises three osteotropic genes in association with said structural bone-compatible matrix.

103. The composition of claim 100, wherein said osteotropic genes are absorbed in or adsorbed to said structural bone-compatible matrix.

104. The composition of claim 100, wherein said osteotropic genes are impregnated within said structural bone-compatible matrix.

105. The composition of claim 100, wherein at least one of said two or more osteotropic genes is in the form of plasmid DNA, a DNA insert within the genome of a recombinant adenovirus, a DNA insert within the geno of a recombinant adeno-associated virus (AAV) or a DNA insert within the genome of a recombinant retrovirus.

106. The composition of claim 100, wherein at least one of said two or more osteotropic genes is a PTH, BMP-2A, BMP-2B, BMP-3, BMP-4, BMP-5, BMP-6, BMP-7, BMP-8, TGF-α, TGF-β1, TGF-β2, FGF, GMCSF, EGF, PDGF, IGF, LTBP or a LIF gene.

107. The composition of claim 106, wherein at least one of said osteotropic genes is a TGF-α, TGF-β1, TGF-β2, PTH, LTBP, BMP-2 or BMP-4 gene.

108. The composition of claim 106, wherein at least one of said osteotropic genes is a PTH gene.

109. The composition of claim 108, wherein at least one of said osteotropic genes is a PTH1-34 gene.

110. The composition of claim 106, wherein at least one of said osteotropic genes is a BMP-2 or BMP-4 gene.

111. The composition of claim 106, wherein said composition comprises a PTH gene and a BMP gene.

112. The composition of claim 111, wherein said composition comprises a PTH1-34 gene and a BMP-4 gene.

113. The composition of claim 100, wherein said structural bone-compatible matrix is a collagenous, metal, hydroxyapatite, bioglass, aluminate, bioceramic, acrylic ester polymer, lactic acid polymer, glycolic acid polymer or lactic acid/glycolic acid polymer matrix.

114. The composition of claim 113, wherein said structural bone-compatible matrix is a titanium matrix.

115. The composition of claim 114, wherein said structural bone-compatible matrix is a titanium matrix coated with hydroxylapatite.

116. The composition of claim 113, wherein said structural bone-compatible matrix is a collagen preparation.

117. The composition of claim 116, wherein said structural bone-compatible matrix is a type II collagen preparation.

118. The composition of claim 117, wherein said structural bone-compatible matrix is a recombinant type II collagen preparation.

119. The composition of claim 117, wherein said structural bone-compatible matrix is a type II collagen preparation further supplemented with minerals.

120. The composition of claim 119, wherein said structural bone-compatible matrix is a type II collagen preparation further supplemented with calcium.

121. The composition of claim 113, wherein said structural bone-compatible matrix is a lactic acid polymer, glycolic acid polymer or lactic acid/glycolic acid polymer matrix.

122. An osteotropic device, comprising two or more osteotropic genes capable of expression by bone progenitor cells, the genes associated with an amount of a structural bone-compatible matrix effective to absorb or adsorb said genes, wherein said device is capable of stimulating bone formation when implanted within a bone progenitor tissue site of an animal.

123. The device of claim 122, wherein said device comprises three or more osteotropic genes.

124. The device of claim 122, wherein said device is a titanium or a hydroxylapatite-coated titanium device.

125. The device of claim 122, wherein said device is shaped to join a bone fracture site in said animal.

126. The device of claim 122, wherein said device is shaped to fill a bone cavity site in said animal.

127. The device of claim 122, wherein said device is an artificial joint.

128. The device of claim 122, wherein said device comprises a PTH, BMP-2A, BMP-2B, BMP-3, BMP-4, BMP-5, BMP-6, BMP-7, BMP-8, TGF-α, TGF-β1, TGF-β2, FGF, GMCSF, EGF, PDGF, IGF, LTBP or a LIF gene.

129. The device of claim 128, wherein said device comprises a TGF-α, TGF-β1, TGF-β2, PTH1-34, LTBP, BMP-2 or BMP-4 gene.

130. The device of claim 128, wherein said device comprises a PTH gene and a BMP gene.

* * * * *

UNITED STATES PATENT AND TRADEMARK OFFICE
CERTIFICATE OF CORRECTION

PATENT NO. : 5,942,496

DATED : August 24, 1999

INVENTOR(S) : Bonadio et al.

It is certified that error appears in the above-identified patent and that said Letters Patent is hereby corrected as shown below:

On title page, section [75], delete "Harbor" and insert --Arbor-- therefor.

In column 101, claim 43, line 1, delete "22" and insert --23-- therefor.
In column 102, claim 65, line 2, after "gene," insert --a--.
In column 103, claim 82, line 1, delete "55" and insert --75-- therefor.
In column 104, claim 105, line 4, delete "geno" and insert "genome" therefor.

Signed and Sealed this

Ninth Day of May, 2000

Attest:

Attesting Officer

Q. TODD DICKINSON

Director of Patents and Trademarks